US011059879B2

(12) United States Patent
Thokala et al.

(10) Patent No.: US 11,059,879 B2
(45) Date of Patent: Jul. 13, 2021

(54) CHIMERIC ANTIGEN RECEPTOR MOLECULES AND USES THEREOF

(71) Applicant: BOARD OF REGENTS, THE UNIVERSITY OF TEXAS SYSTEM, Austin, TX (US)

(72) Inventors: Radhika Thokala, Houston, TX (US); Laurence J.N. Cooper, Houston, TX (US); Simon Olivares, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 275 days.

(21) Appl. No.: 15/771,128

(22) PCT Filed: Oct. 27, 2016

(86) PCT No.: PCT/US2016/059010
§ 371 (c)(1),
(2) Date: Apr. 26, 2018

(87) PCT Pub. No.: WO2017/075147
PCT Pub. Date: May 4, 2017

(65) Prior Publication Data

US 2019/0055299 A1 Feb. 21, 2019

Related U.S. Application Data

(60) Provisional application No. 62/246,931, filed on Oct. 27, 2015.

(51) Int. Cl.

| | |
|---|---|
| ***C07K 14/705*** | (2006.01) |
| ***A61K 39/44*** | (2006.01) |
| ***A61K 39/00*** | (2006.01) |
| ***A61K 39/395*** | (2006.01) |
| ***A61P 35/02*** | (2006.01) |
| ***A61P 35/00*** | (2006.01) |
| ***C07K 14/725*** | (2006.01) |
| ***C07K 16/28*** | (2006.01) |
| ***A61K 38/00*** | (2006.01) |

(52) U.S. Cl.
CPC ........ *C07K 14/70517* (2013.01); *A61K 39/00* (2013.01); *A61K 39/39558* (2013.01); *A61K 39/44* (2013.01); *A61P 35/00* (2018.01); *A61P 35/02* (2018.01); *C07K 14/7051* (2013.01); *C07K 14/70521* (2013.01); *C07K 16/2866* (2013.01); *A61K 38/00* (2013.01); *A61K 2039/507* (2013.01); *A61K 2039/5158* (2013.01); *C07K 2317/56* (2013.01); *C07K 2317/565* (2013.01); *C07K 2319/02* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 9,629,877 | B2 * | 4/2017 | Cooper | C07K 14/70521 |
| 9,657,105 | B2 | 5/2017 | Forman et al. | |
| 9,701,758 | B2 | 7/2017 | Cooper et al. | |
| 10,391,126 | B2 * | 8/2019 | Cooper | A61K 35/17 |
| 2014/0322212 | A1 * | 10/2014 | Brogdon | C07K 14/70517 424/134.1 |
| 2014/0349402 | A1 | 11/2014 | Cooper et al. | |
| 2016/0096902 | A1 | 4/2016 | Cooper et al. | |
| 2016/0158285 | A1 | 6/2016 | Cooper et al. | |
| 2016/0256487 | A1 | 9/2016 | Cooper et al. | |
| 2016/0333108 | A1 | 11/2016 | Forman et al. | |
| 2017/0044500 | A1 | 2/2017 | Cooper et al. | |
| 2017/0158749 | A1 | 6/2017 | Cooper et al. | |
| 2017/0183407 | A1 | 6/2017 | Cooper et al. | |
| 2017/0333480 | A1 | 11/2017 | Cooper et al. | |
| 2017/0334968 | A1 | 11/2017 | Cooper et al. | |
| 2018/0051265 | A1 | 2/2018 | Cooper et al. | |
| 2018/0298349 | A1 | 10/2018 | Rushworth et al. | |
| 2018/0353544 | A1 * | 12/2018 | Rezvani | C07K 14/4748 |

FOREIGN PATENT DOCUMENTS

| | | | |
|---|---|---|---|
| WO | WO 2013/074916 | 5/2013 | |
| WO | WO 2014/186469 | 11/2014 | |
| WO | WO 2014/190273 | 11/2014 | |
| WO | WO 2015/061694 | 4/2015 | |
| WO | WO-2015105522 A1 * | 7/2015 | C07K 14/70517 |
| WO | WO 2015/123642 | 8/2015 | |

(Continued)

OTHER PUBLICATIONS

Almagro & Fransson, Frontiers in Bioscience 2008; 13:1619-33 (Year: 2008).*

(Continued)

*Primary Examiner* — Peter J Reddig
(74) *Attorney, Agent, or Firm* — Parker Highlander PLLC

(57) ABSTRACT

Chimeric antigen receptor (CAR) polypeptides are provided comprising an antigen binding domain; a hinge domain; a transmembrane domain and an intracellular signaling domain, wherein the CAR polypeptide binds to a target antigen and wherein the antigen binding domain comprises HCDR sequences from a first antibody that binds to the target antigen and LCDR sequences from a second antibody that binds to the target antigen. In certain aspects, the target antigen is CD123.

16 Claims, 29 Drawing Sheets

Specification includes a Sequence Listing.

(56) References Cited

FOREIGN PATENT DOCUMENTS

| | | |
|---|---|---|
| WO | WO 2015/142675 | 9/2015 |
| WO | WO 2015/164594 | 10/2015 |
| WO | WO 2015/164740 | 10/2015 |
| WO | WO 2016/073629 | 5/2016 |
| WO | WO 2016/073755 | 5/2016 |
| WO | WO 2016/138091 | 9/2016 |
| WO | WO 2016/145146 | 9/2016 |
| WO | WO 2017/048902 | 3/2017 |

OTHER PUBLICATIONS

Deniger, Drew C., et al. "Sleeping beauty transposition of chimeric antigen receptors targeting receptor tyrosine kinase-like orphan receptor-1 (ROR1) into diverse memory T-cell populations." *PloS one* 10.6 (2015): e0128151.

Office Communication issued in corresponding European Application No. 16 794 836.3, dated Feb. 8, 2019.

PCT International Preliminary Report on Patentability issued in International Application No. PCT/US2016/059010, dated May 11, 2018.

PCT International Search Report and Written Opinion issued in International Application No. PCT/US2016/059010, dated Feb. 8, 2017.

Thokala, Radhika, et al. "Redirecting specificity of T cells using the sleeping beauty system to express chimeric antigen receptors by mix-and-matching of VL and VH domains targeting CD123+ tumors." *PLoS One* 11.8 (2016): e0159477.

Thokala, Radhika, et al. "Re-Directing T cells with chimeric antigen receptors to target CD123+ Leukemia." *Molecular Therapy*, vol. 21, No. Suppl. 1, May 2013, S247-S248.

* cited by examiner

ISOTYPE
K562-PARENTAL
K562-CLONE1

| | | | | | | |
|---|---|---|---|---|---|---|
| CAR-1 | $V_L$-26292 | $V_H$-26292 | CD8a | CD8TM | CD28 | CD3ζ |
| CAR-2 | $V_L$-32701 | $V_H$32701 | CD8a | CD8TM | CD28 | CD3ζ |
| CAR-3 | $V_L$-32703 | $V_H$32703 | CD8a | CD8TM | CD28 | CD3ζ |
| CAR-4 | $V_L$-32716 | $V_H$32716 | CD8a | CD8TM | CD28 | CD3ζ |
| | | | | | | |
|---|---|---|---|---|---|---|
| CAR-5 | $V_L$-26292 | $V_H$32701 | CD8a | CD8TM | CD28 | CD3 |
| CAR-6 | $V_L$-26292 | $V_H$-32703 | CD8a | CD8TM | CD28 | CD3 |
| CAR-7 | $V_L$-26292 | $V_H$32716 | CD8a | CD8TM | CD28 | CD3 |
| CAR-8 | $V_L$-32701 | $V_H$32716 | CD8a | CD8TM | CD28 | CD3 |
| CAR-9 | $V_L$-32703 | $V_H$26292 | CD8a | CD8TM | CD28 | CD3 |
| CAR-10 | $V_L$-26292 | $V_H$32703 | IgG4 | CD28TM | CD28 | CD3 |
FIG. 3A
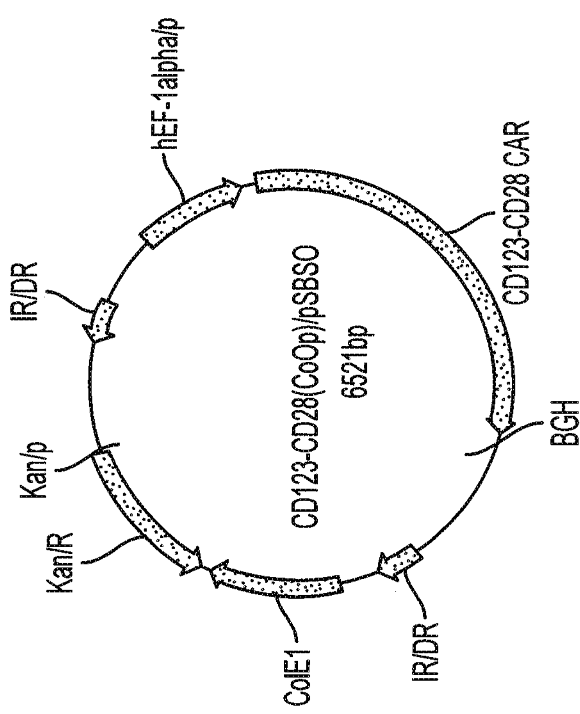
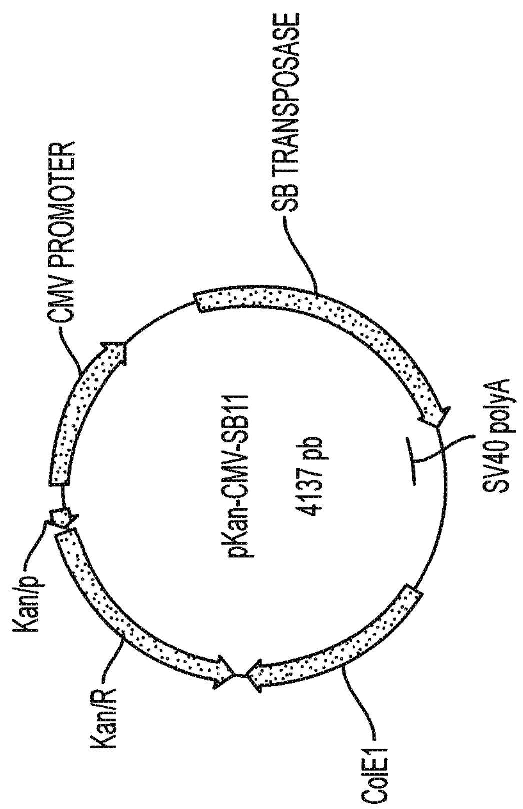
FIG. 3B

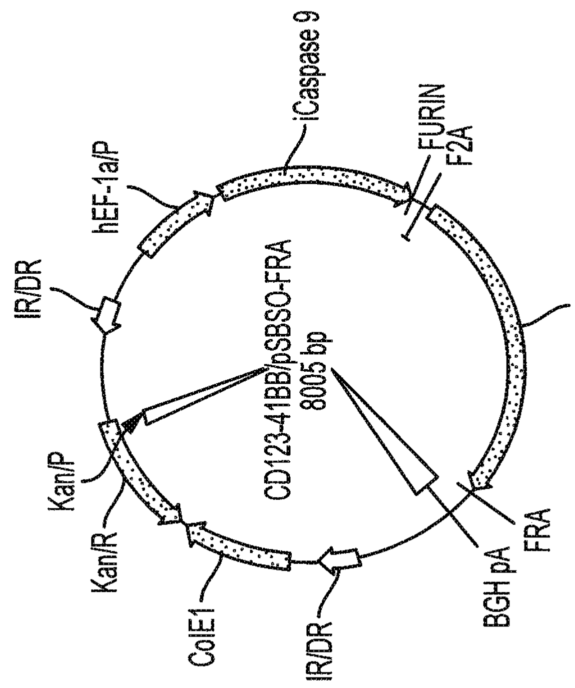
FIG. 11B
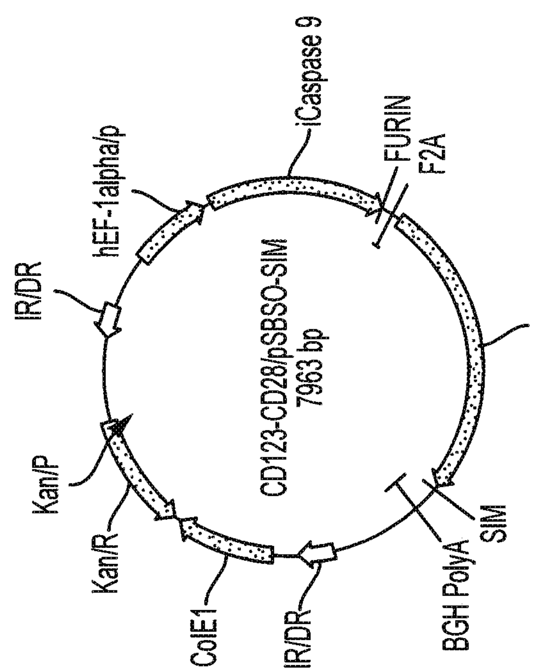
FIG. 11A
CD123-CD28 CAR: iCaspase 9 | $V_L$-26292 | $V_H$-32703 | IgG4 | CD28TM | CD28 | CD3ζ
CD123-CD137 CAR: iCaspase 9 | $V_L$-26292 | $V_H$-32703 | IgG4 | CD28TM | CD137 | CD3ζ
FIG. 11C

CHIMERIC ANTIGEN RECEPTOR MOLECULES AND USES THEREOF

This application is a national phase application under 35 U.S.C. § 371 of International Application No. PCT/US2016/059010, filed Oct. 27, 2016, which claims the benefit of U.S. Provisional Patent Application No. 62/246,931, filed Oct. 27, 2015, the entirety of each of which is incorporated herein by reference.

INCORPORATION OF SEQUENCE LISTING

The sequence listing that is contained in the file named "UTFCP1286WO_ST25.txt", which is 64 KB (as measured in Microsoft Windows®) and was created on Oct. 26, 2016, is filed herewith by electronic submission and is incorporated by reference herein.

BACKGROUND OF THE INVENTION

1. Field of the Invention

The present invention relates generally to the field of molecular biology and immunology. More particularly, it concerns chimeric-antigen receptor (CAR)-targeting molecules and methods of using the same.

2. Description of Related Art

Immunotherapy holds great promise for improving outcomes for some of the worst cancers, including acute myelogenous leukemia (AML). Tremendous advances have been seen in recent years from several applications of immune-based treatment (193, 194, 195), especially those that exploit the precise antigen recognition of monoclonal antibodies (mAbs). An especially promising development has been the creation of chimeric antigen receptors (CAR) for T cells (196), utilizing single chain polypeptides encoding the $V_H$ and $V_L$ domains (scFv) of a mAb, coupled with a transmembrane domain and the CD3ζ chain. Second generation CARs include the signaling domain of either CD28 (197, 119) or CD137 (118, 198, 199) to provide "signal 2," which is essential for improved activation and function, as well as for prolonged T cell survival. The use of $CAR_+$ T cells whose antigen recognition has been redirected to specific tumor associated antigens (TAA) for adoptive immunotherapy has already provided remarkable success in early phase clinical trials (200, 7, 201), though several important questions remain regarding optimal CAR design and choice of TAA for an increasing range of malignancies. Some of these key questions include how to tune the sensitivity of CAR T cells to recognize the increased levels of TAA on tumor cells while avoiding the toxicities that arise from recognition of normal cells (202), and which costimulatory signal provides the best phenotype and persistence for $CAR_+$ T cells.

SUMMARY OF THE INVENTION

In a first embodiment there is provided a chimeric antigen receptor (CAR) polypeptide comprising, from N- to C-terminus or from C- to N-terminus, an antigen binding domain; a hinge domain; a transmembrane domain and an intracellular signaling domain, wherein the CAR polypeptide binds to a target antigen and wherein the antigen binding domain comprises HCDR sequences from a first antibody that binds to the target antigen and LCDR sequences from a second antibody that binds to the target antigen. In some aspects, the target antigen is CD123.

In further aspects, the antigen binding domain comprises: (i) LCDR1-3 sequences from the 26292 antibody and HCDR1-3 sequences from the 26292 antibody; (ii) LCDR1-3 sequences from the 32701 antibody and HCDR1-3 sequences from the 32701 antibody; (iii) LCDR1-3 sequences from the 32703 antibody and HCDR1-3 sequences from the 32703 antibody; (iv) LCDR1-3 sequences from the 32716 antibody and HCDR1-3 sequences from the 32716 antibody; (v) LCDR1-3 sequences from the 26292 antibody and HCDR1-3 sequences from the 32701 antibody; (vi) LCDR1-3 sequences from the 26292 antibody and HCDR1-3 sequences from the 32703 antibody; (vii) LCDR1-3 sequences from the 26292 antibody and HCDR1-3 sequences from the 32716 antibody; (viii) LCDR1-3 sequences from the 32701 antibody and HCDR1-3 sequences from the 32716 antibody; or (ix) LCDR1-3 sequences from the 32703 antibody and HCDR1-3 sequences from the 26292 antibody.

In certain aspects, the LCDR1-3 sequences may comprise a sequence at least about 85%, 86%, 87%, 88%, 89%, 90%, 91%, 92%, 93%, 94%, 95%, 96%, 97%, 98% or 99% identical to the CDR1-3 sequences of SEQ ID NOs: 2, 4, 6, or 8. In a further aspect, a CAR polypeptide of the embodiments comprises a sequence at least about 85%, 86%, 87%, 88%, 89%, 90%, 91%, 92%, 93%, 94%, 95%, 96%, 97%, 98% or 99% identical to SEQ ID NOs: 2, 4, 6, or 8. In other aspects, the HCDR1-3 sequences may comprise a sequence at least about 85%, 86%, 87%, 88%, 89%, 90%, 91%, 92%, 93%, 94%, 95%, 96%, 97%, 98% or 99% identical to the CDR1-3 sequences of SEQ ID NOs: 1, 3, 5, or 7. In still a further aspect, a CAR polypeptide of the embodiments comprises a sequence at least about 85%, 86%, 87%, 88%, 89%, 90%, 91%, 92%, 93%, 94%, 95%, 96%, 97%, 98% or 99% identical to SEQ ID NOs: 1, 3, 5, or 7.

In still further aspects, the HCDR sequences from the first antibody are selected from the group consisting of the HCDR1-3 sequences from antibodies 26292, 32701, 32703; and 32716. In other aspects, the LCDR sequences from the second antibody are selected from the group consisting of the LCDR1-3 sequences from antibodies 26292, 32701, 32703; and 32716.

In some aspects, the hinge domain may comprise a sequence at least about 85%, 86%, 87%, 88%, 89%, 90%, 91%, 92%, 93%, 94%, 95%, 96%, 97%, 98% or 99% identical to a CD8a hinge (KPTTTPAPRPPTPAPTIASQPLSLRPEACRPAAGGAVHTRGLD (SEQ ID NO: 12)) or an IgG4 hinge (ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKM (SEQ ID NO: 13)). In particular aspects, the hinge domain is a CD8a hinge (SEQ ID NO: 12) or an IgG4 hinge (SEQ ID NO: 13).

In additional aspects, the transmembrane domain may comprise a sequence at least about 85%, 86%, 87%, 88%, 89%, 90%, 91%, 92%, 93%, 94%, 95%, 96%, 97%, 98% or 99% identical to a CD8a transmembrane domain (FACDIYIWAPLAGTCGVLLLSLVITLYCNHRN (SEQ ID NO: 14)) or a CD28 transmembrane domain (FWVLVVVGGVLACYSLLVTVAFIIFWV (SEQ ID NO: 15). In specific aspects, the transmembrane domain is a CD8a transmembrane domain (SEQ ID NO: 14) or a CD28 transmembrane domain (SEQ ID NO: 15).

In yet still further aspects, the intracellular signaling domain may comprise a sequence at least about 85%, 86%, 87%, 88%, 89%, 90%, 91%, 92%, 93%, 94%, 95%, 96%, 97%, 98% or 99% identical to a CD3z intracellular signaling domain (RVKFSRSADAPAYQQGQNQLYNELNLGR-REEYDVLDKRRGRDPEMGGKPRRKNP QEGLY-NELQKDKMAEAYSEIGMKGERRRGKGHDGLYQGL-STATKDTYDALHMQA LPPR (SEQ ID NO: 16)). In a certain particular aspect, the intracellular signaling domain is a CD3z intracellular signaling domain (SEQ ID NO: 16).

In still a further aspect, a CD123 CAR of the embodiments comprises a sequence at least about 85%, 86%, 87%, 88%, 89%, 90%, 91%, 92%, 93%, 94%, 95%, 96%, 97%, 98% or 99% identical to SEQ ID NO: 17, 18, 19, 20, 48, 49, 50, 51, 52 or 53.

In a further embodiment there are provided nucleic acid molecules encoding a CAR polypeptide in accordance with the embodiments above. In some aspects, the sequence encoding the CAR is flanked by transposon repeats (IR/DR). In further aspects, the sequence encoding the CAR is operatively linked to expression control sequences.

In yet a further embodiment there is provided an isolated immune effector cell comprising a CAR polypeptide or nucleic acid in accordance with the embodiments herein. In some aspects the cell is a T-cell, a NK cell, a NK T cell or a progenitor of one of these cell types. In further aspects, the cell is a human cell. A further embodiment provides a pharmaceutical composition comprising a population of cells in accordance with the embodiments in a pharmaceutically acceptable carrier.

In certain aspects, engineered immune effector cells of the embodiments can be used in methods to treat cancer. For example, the cancer can be a CD123 positive cancer. In some aspects the cancer is a leukemia. For example, the leukemia can be an acute myeloid leukemia (AML), a chronic myeloid leukemia (CML), an acute lymphocytic leukemia (ALL) or a chronic lymphocytic leukemia (CLL).

In yet a further embodiment, there is provided a method comprising obtaining a sample of cells comprising T-cells or T-cell progenitors or other immune effector cells such as NK or NKT cells, transfecting the cells with a DNA encoding a CAR polypeptide in accordance with the embodiments, to provide a population of engineered CAR-expressing T-cells, and culturing the population of engineered CAR cells ex vivo in a medium that selectively enhances proliferation of CAR-expressing T-cells (e.g., co-culture with an irradiated feeder cell based system). In certain aspects, the method further comprises transfecting the cells with a transposon-flanked CAR and a transposase effective to integrate the DNA encoding the CAR into the genome of the cells. In further aspects, a method comprises purifying or enriching immune effector cells (e.g., T-cells) in the sample prior to transfection. In certain cases, the immune effector cells, such as T-cells or T-cell progenitors, are derived from induced pluripotent stem cells or embryonic stem cells. In further aspects, enriching T-cells in the sample comprises collecting a mononuclear cell fraction. The sample of cells may be from umbilical cord blood, a lymphoid organ or a peripheral blood sample from the subject in some cases. The sample of cells may be obtained by apheresis or venipuncture in some cases. In still further aspects, the sample of cells is a subpopulation of T-cells. The engineered CAR cells are inactivated for expression of an endogenous T-cell receptor and/or endogenous HLA in some aspects. Obtaining the sample of cells comprises obtaining the cells from a 3rd party in some further aspects.

In some aspects, the transfection comprises electroporating DNA encoding a CAR into the T cell. The transfection may not involve infecting or transducing the cells with virus in some aspects. In still further aspects, the cells are additionally transfected with a nucleic acid encoding a membrane-bound Cγ cytokine. The membrane-bound Cγ cytokine may be a membrane bound IL-7, IL-15 or IL-21 in some instances. In a specific aspect, the membrane-bound Cγ cytokine is IL-15-IL-15Rα fusion protein.

In still further aspects, the DNA encoding the CAR is a plasmid. The transposase may be provided as a DNA expression vector, an mRNA, a polypeptide, or an expressible RNA in some aspects. In a specific aspect, the transposase is salmonid-type Tcl-like transposase (SB). In a further specific aspect, the transposase is the SB11 or SB100x transposase.

In a further embodiment, there is provided a CAR T-cell population made by a method of any one of the embodiments detailed herein.

Embodiments discussed in the context of methods and/or compositions of the embodiments may be employed with respect to any other method or composition described herein. Thus, an embodiment pertaining to one method or composition may be applied to other methods and compositions of the embodiments as well.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-3B. CD123-specific CARs with chimeric scFvs: (A) Left. Regular CARs (CARs 1 to 4; SEQ ID NOs: 17, 18, 19, and 20) derived by fusing $V_H$ and $V_L$ chains of mAbs specific to CD123. Right. Chimeric CARs (CARs 5 to 10; SEQ ID NOs: 48, 49, 50, 51, 52, and 53) derived from chimeric scFvs of mAbs by mix and matching $V_H$ and $V_L$ chains. (B) Left. Typical representation of Sleeping Beauty transposon plasmid containing CD123-specific CAR with CD28 co-stimulatory domain. IR/DR: Sleeping Beauty Inverted Repeat/Direct repeats, ColE1: A minimal *E. coli* origin of replication, Kanamycin (Kan/R): Bacterial selection gene encoding Kanamycin resistance, Kanamycin promoter (Kan/p); Prokaryotic promoter. hEF-1alpha/p: human Elongation Factor-1 alpha region hybrid promoter; CD123-CD28 CAR: Human codon optimized CD123-specific CAR with CD28 co-stimulatory domain; BGH polyA; Bovine growth hormone poly adenylation sequence, (right) SB11 transposase; CMV promoter (Cytomegalovirus promoter) SV40 PolyA (Simian Virus 40 PolyA).

FIGS. 11A-11C. CD123-specific CAR plasmids. DNA plasmid vector maps for (A) CD123-CD28 CAR and (B) CD123-CD137 CAR. Abbreviations are as follows, IR/DR: Sleeping Beauty Direct repeats/Inverted Repeat, ColE1: A minimal *E. coli* origin of replication, Kanamycin (Kan/R): Bacterial selection gene encoding Kanamycin resistance, Kanamycin promoter (Kan/p); prokaryotic promoter. hEF-1alpha/p: human elongation factor-1 alpha region hybrid promoter iCaspase 9; induced caspase 9 suicide gene. CD123-CD28 CAR: human codon optimized CD123-specific scFv fused to Fc, CD28 endo-domain and CD3 zeta chimeric antigen receptor, CD123-CD137 CAR: human codon optimized CD123-specific scFv fused to Fc, CD137 endo-domain and CD3 zeta chimeric antigen receptor SIM: "SIM" PCR tracking oligonucleotides, FRA: "FRA" PCR tracking oligonucleotides, BGH polyA; B ovine growth hormone poly adenylation sequence.

CAR$^+$ T cells (Black bars) and CD123-CD137 CAR$^+$ T cells (Grey bars) (n=3). Statistical analysis by Student's t test or nonparametric Mann-whitney method.

Figure 15B:
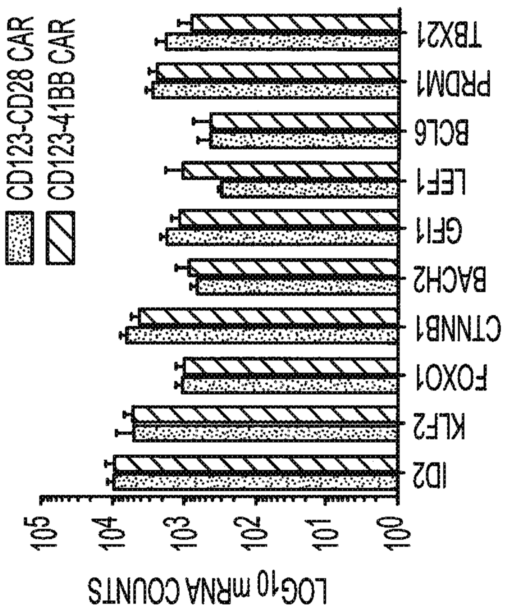
Figure 15C:
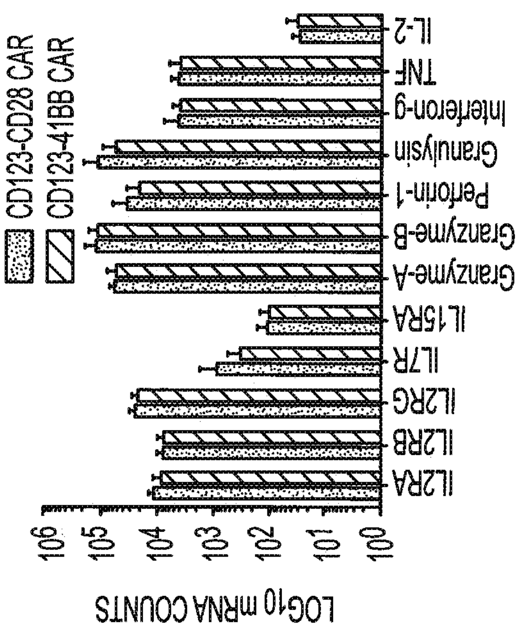
Figure 15A:
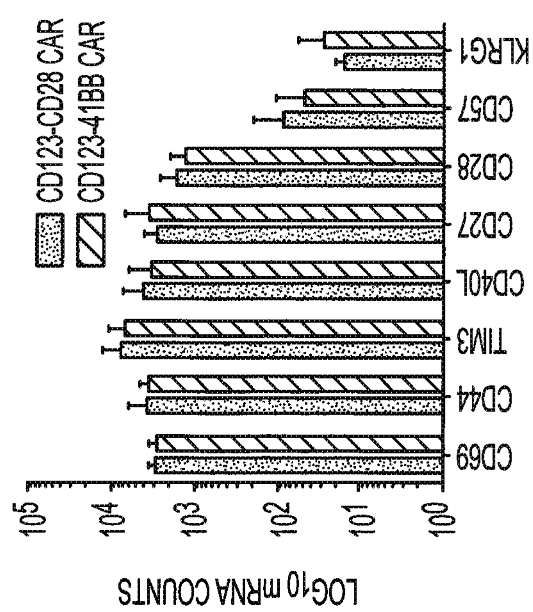

FIGS. 15A-15C. Transcriptional profile of iCaspase 9$^+$CD123-specific CARs. mRNA transcripts of lymphocyte genes expressed on CAR T cells analyzed by non-enzymatic digital multiplex array of (A) transcriptional profile of activation, co-stimulation and exhaustion, (B) transcription factors associated with less differentiated phenotype and late memory stages, and (C) cytokine receptors for survival and markers associated with effector function.

Figures 16A, 16B:
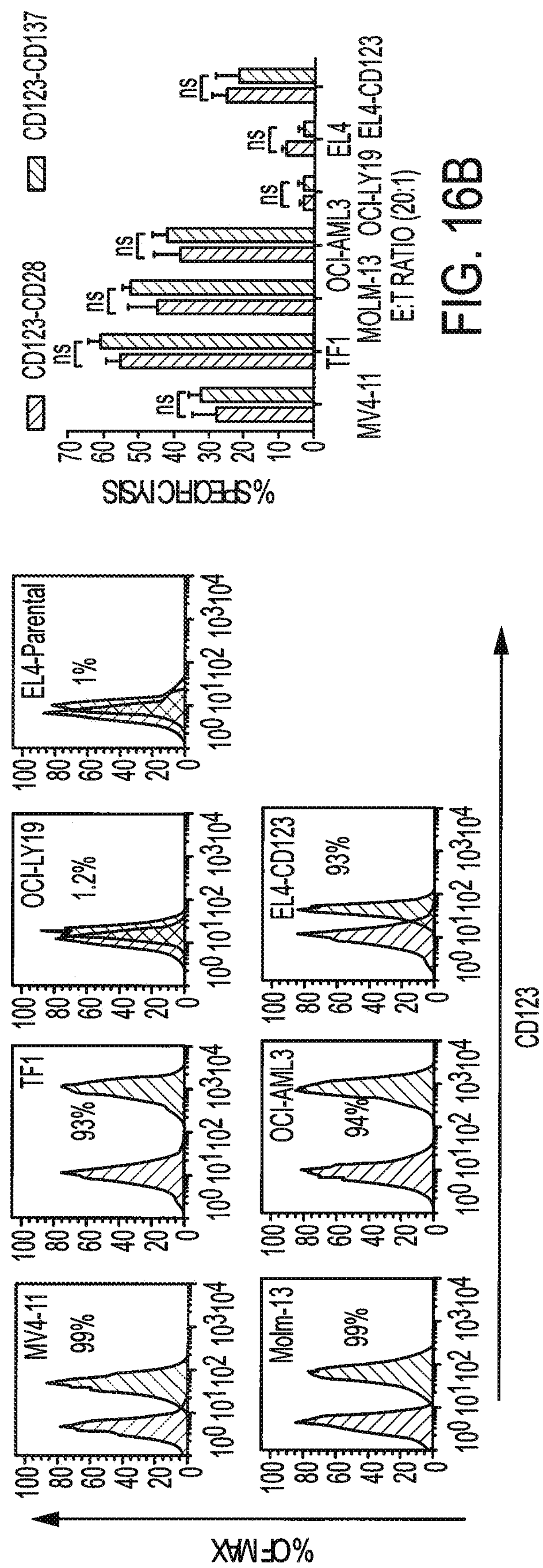

FIGS. 16A-16B. In vitro lysis of iCaspase$^+$ CD123-specific CARs in AML. (A) Flow cytometric analysis of CD123 expression on AML cell lines MV4-11, Molm-13, TF1, OCI-AML3, EL4-Parental and EL4-Parental cells transfected with CD123. Percentage of CD123 positive cells (grey filled) over isotype controls (not filled) are indicated in each histogram. (B) Specific lysis of CD123- CD28 and CD123-CD137 CAR$^+$ T cells against AML cell lines MV4-11, Molm-13, TF1,OCI-AML3, CD123$^{neg}$ OCI-Ly19, EL4 and EL4 transfected with CD123 in a 4 hour chromium release assay, Data are mean±SD n=3.

Figure 17A:
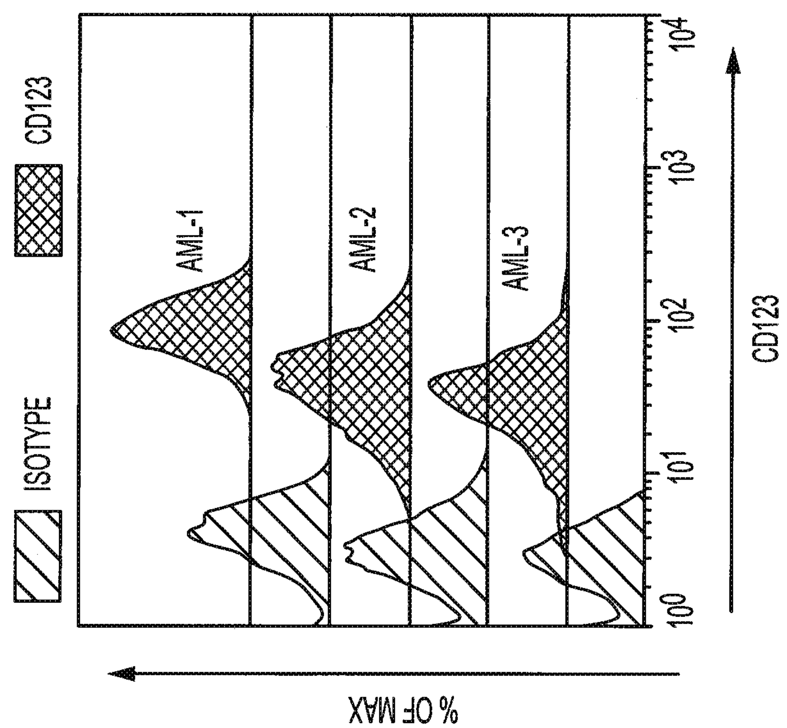
Figure 17B:
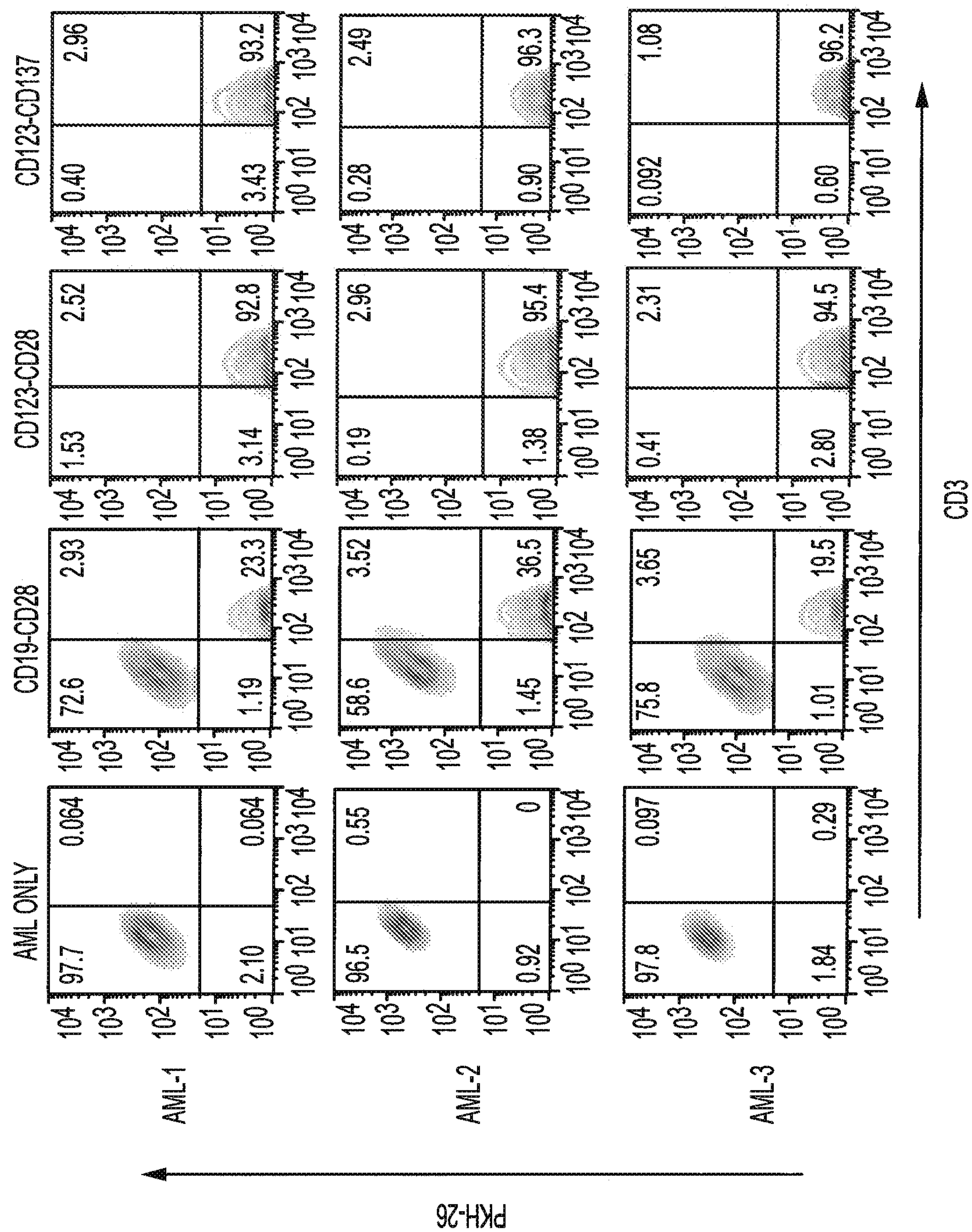

FIGS. 17A-17B. In vitro lysis of iCaspase+CD123-specific cells in AML primary samples. (A) Flow cytometric analysis of CD123 expression on primary AML samples used in co-culture assay. (B) PKH-26 labeled Primary AML primary cells were co-cultured with CD123-CD28 and CD123-CD137 CAR T cells at 1:1 ratio for 72 hours. CD19-CD28 was used as negative control. At the end of the culture, cells were stained using anti-CD3 to distinguish between T cells and PKH-26 labeled tumor cells.

Figures 18A, 18B:
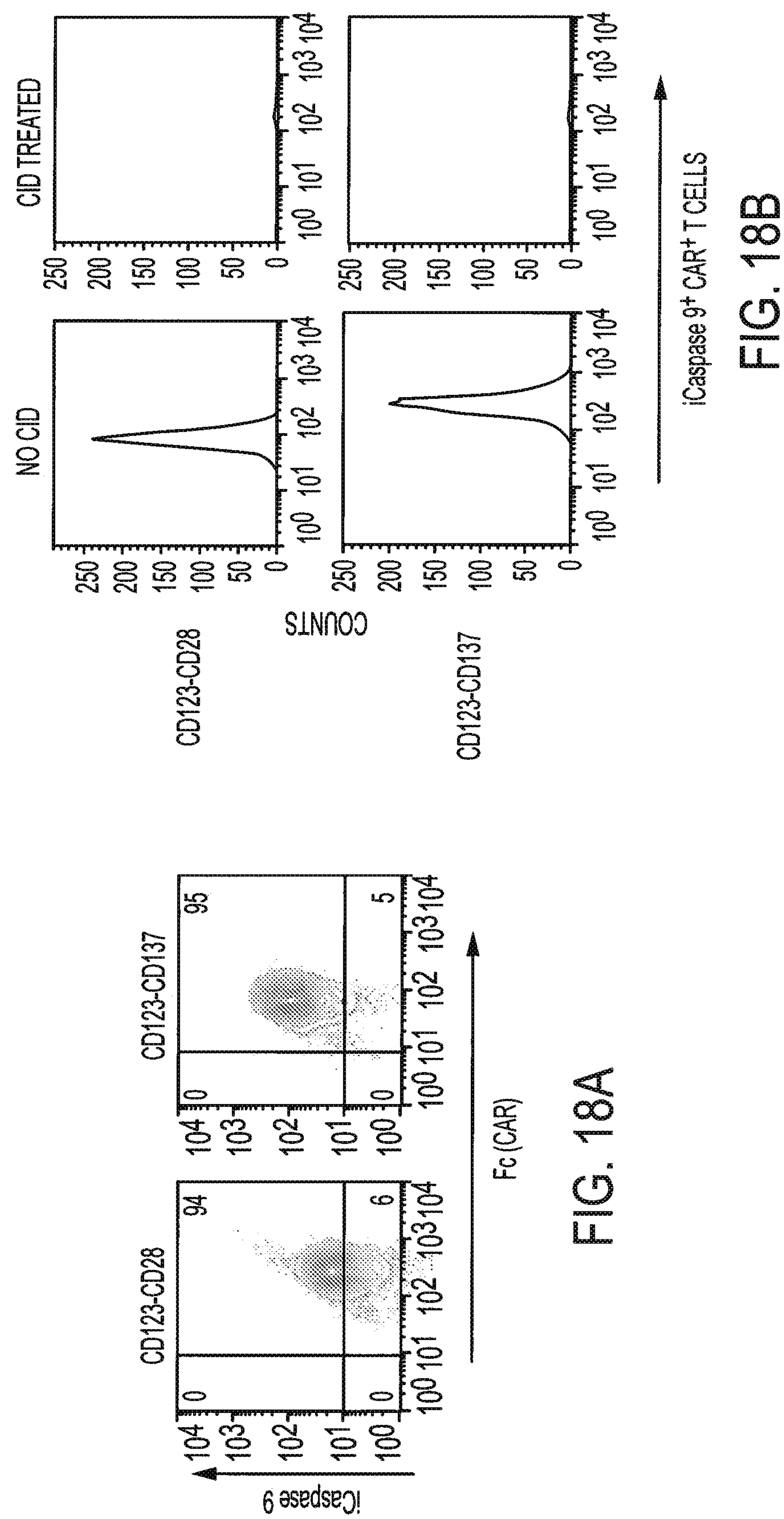

FIGS. 18A-18B. In vitro functionality of iCaspase 9 in iCaspase 9-CD123-specific CARs. (A) iCaspase 9 expression on CAR T cells, assessed by flow cytometry. (B) In vitro functionality of iCasp9 was assessed by treating CAR T cells with 100 nM chemical inducer of dimerization (CID) a synthetic homodimerizer AP20187 for 24 hours which rapidly eliminated T cells in CID treated group.

FIGS. 19A-19F. In vivo efficacy of iCaspase 9$^+$ CD123-specific CAR T cells in NSGS mice. (A) AML cell line TF1 was genetically modified with lentivirus particles to express mKate red fluorescent protein and enhanced firefly luciferase (effluc). Flux intensity in TF1 cell line compared to non-transduced TF1 cells, measured by firefly luciferase assay (**$p<0.0001$) (B) Schematic of TF1 xenograft model. 2.5×10e6 TF1-effLuc-mKate cells were intravenously injected into NSGS mice on day 0. On Day 5 tumor engraftment was quantified using Non-invasive bioluminescence imaging (BLI) and mice randomly divided into 3 groups and treated with 3 infusions of CD123-28 or CD123-CD137 CAR T cells and untreated group received no T cells followed by IL-2 treatment and BLI on day 5, 11 and 20 (C) BLI images of mice showing tumor reduction in CD123-CD28 and CD123-CD137 CAR treated group compared to untreated group ($p<0.01$ (D) Flux activity measured by BLI in CD123-CD28 or CD123- CD137 treated group in comparison to untreated group. Statistical analysis by two way ANOVA ($p<0.01$) (E) Survival of mice treated with CD123-CD28 CAR T cells compared to mice treated with CD123-CD137 CAR T cells. Log-rank (Mantel-Cox) test was used for statistical analysis. $p>0.05$ ns (not significant). (F) Histograms represent the luciferase activity measured by BLI for each group ($p<0.01$).

Figure 20B:
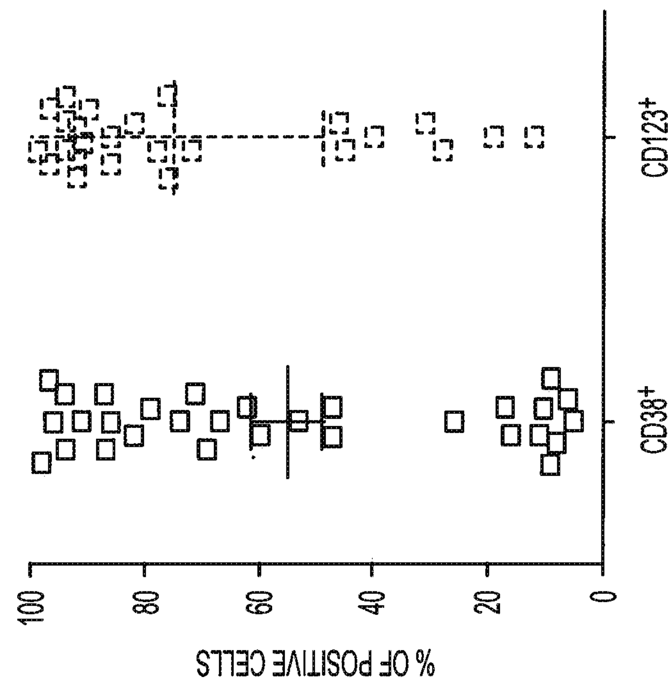
Figure 20A:
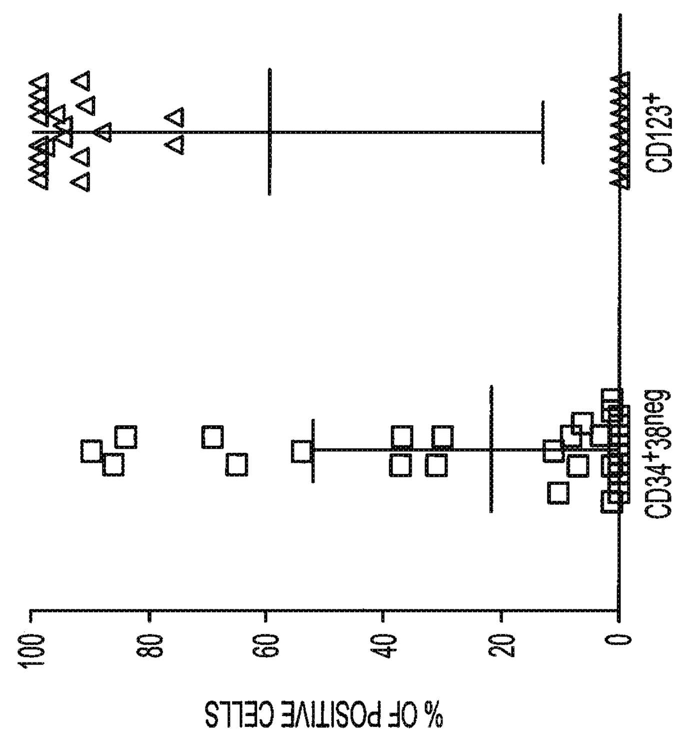

FIGS. 20A-20B. CD123 expression analysis on LSCs in AML. Mononuclear cells were isolated from peripheral blood from primary AML patients and stained with antibodies specific to CD123 CD34 and CD38. CD123 expression assessed on phenotypically defined (A, CD34$^+$ and CD38$^{neg}$) and blasts (B, CD38$^+$) fractions. Mean+SD N=30.

Figure 21:
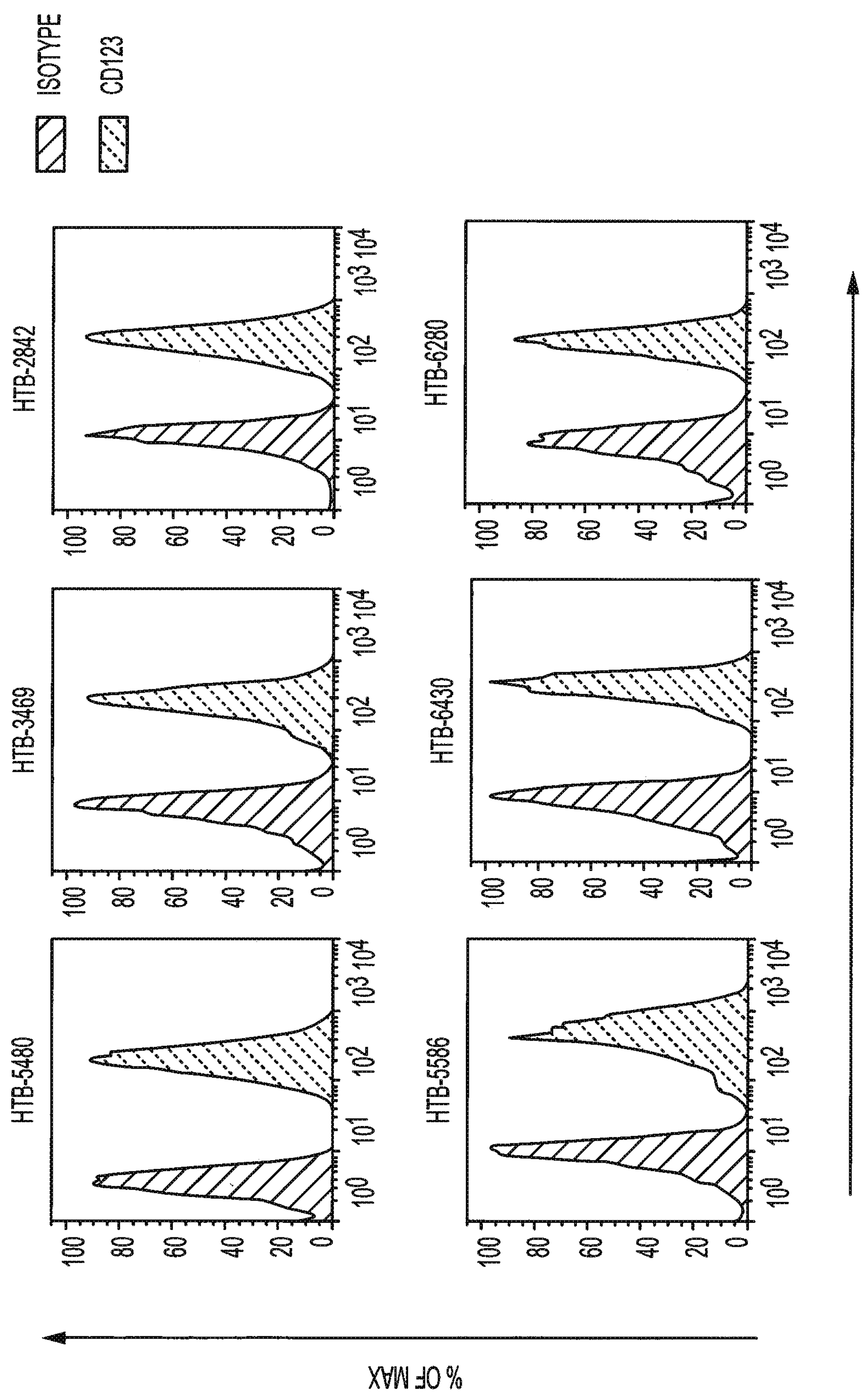

FIG. 21. CD123 expression on AML isolated leukemic stem cells. Lin$^{neg}$ cells from MNCs of patient samples were isolated with CD34 diamond isolation kit (Miltenyi), and FACS sorted into CD34$^+$CD38$^{neg}$ population and stained with CD123 antibody with appropriate isotype controls.

Figure 22A:
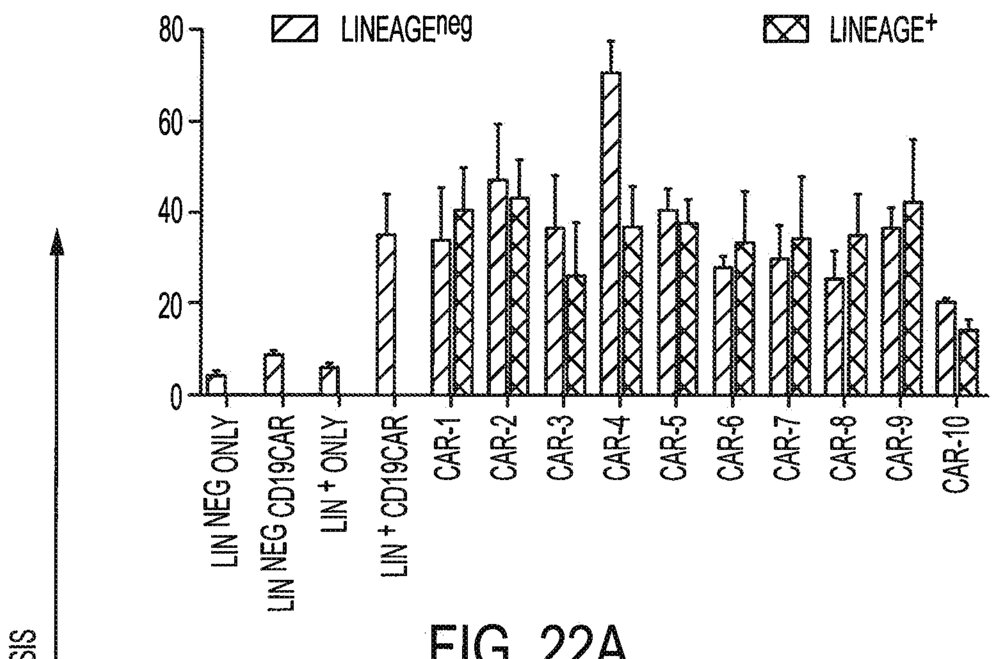
Figure 22B:
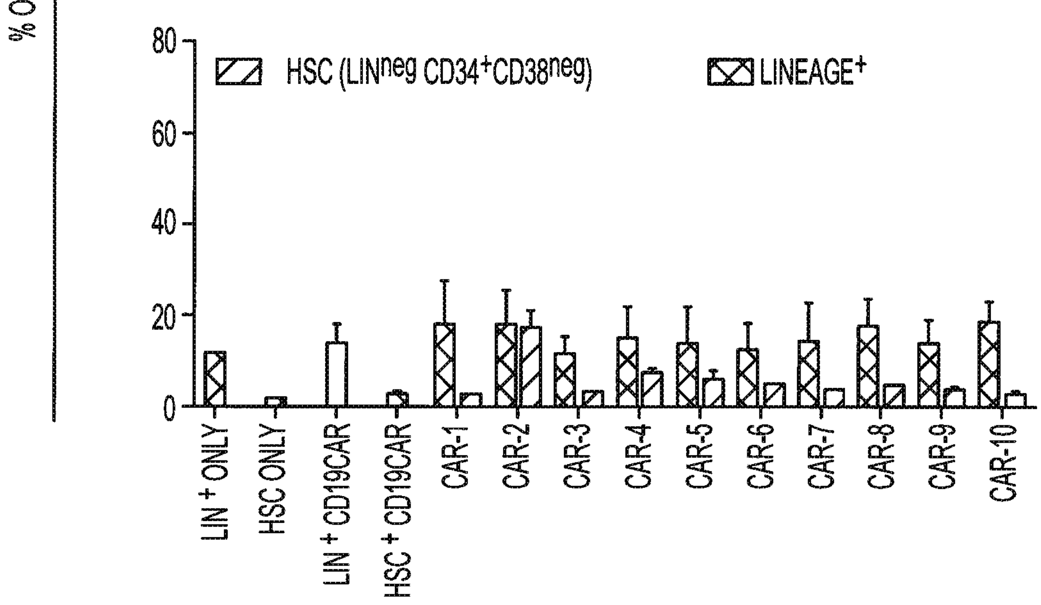

FIG. 22A-22B. In vitro lysis of normal hematopoietic cells by chimeric CARs. isolated lineage positive and negative cells from normal BM samples, Lineage$^+$ and HSCs (lin$^{neg}$ CD34$^+$CD38$^{neg}$) from cord blood MNCs, labeled with PKH-26 and co-cultured with chimeric CAR T cells in E:T ratio 1:1 for 48 hours.

Figure 23:
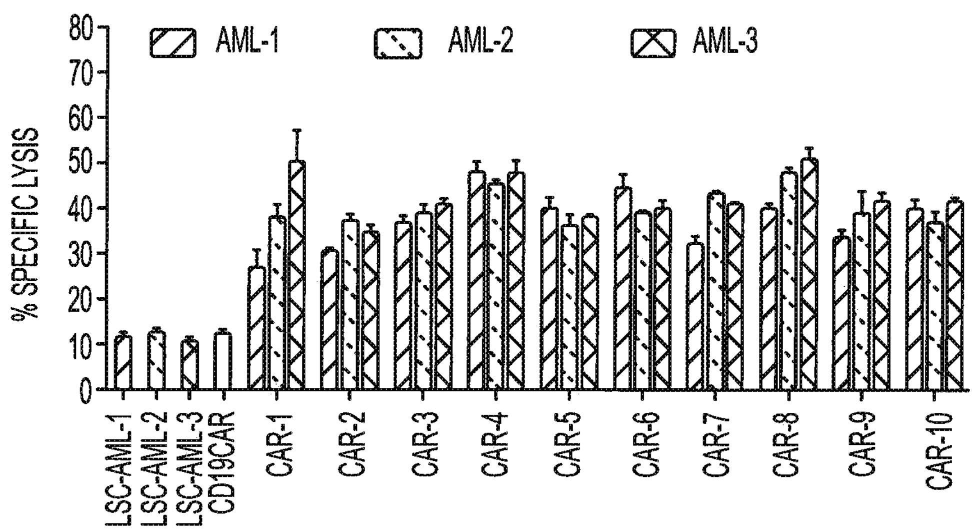

FIG. 23. Lin$^{neg}$ CD34$^+$CD38$^{neg}$ from three AML patient samples labeled with PKH-26 and co-cultured with chimeric CAR T cells in E:T ratio 1:1 for 48 hours. CD19 CAR T cells used as negative control. Cells were stained with 7-AAD to distinguish dead and live cells to assess killing.

Figure 24:
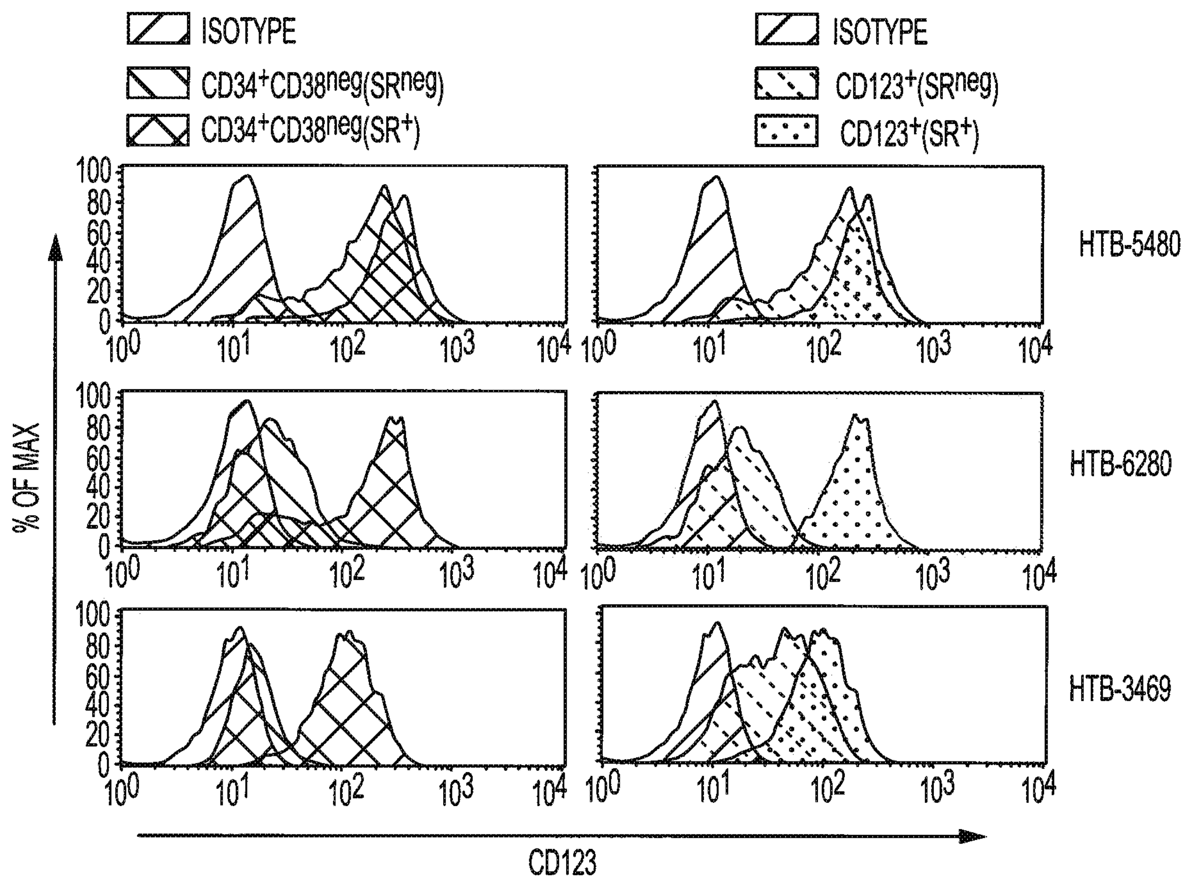

FIG. 24. Expansion of AML-LSCs under hypoxic conditions. lin$^{neg}$ CD34$^+$CD38$^{neg}$ fraction was isolated from relapsed AML patients HTB-5480, HTB-3469, HTB-6280 and cultured at 1% oxygen and 5% $CO_2$. Cells were cultured in serum free stemspanII media (stem cell technologies) in presence SR1 1 μM/ml supplemented by cytokines stem cell factor (SCF), human FLT3 ligand, interleukin-3 for 7 days. SR1 non treated cells used as control.

Figure 25:
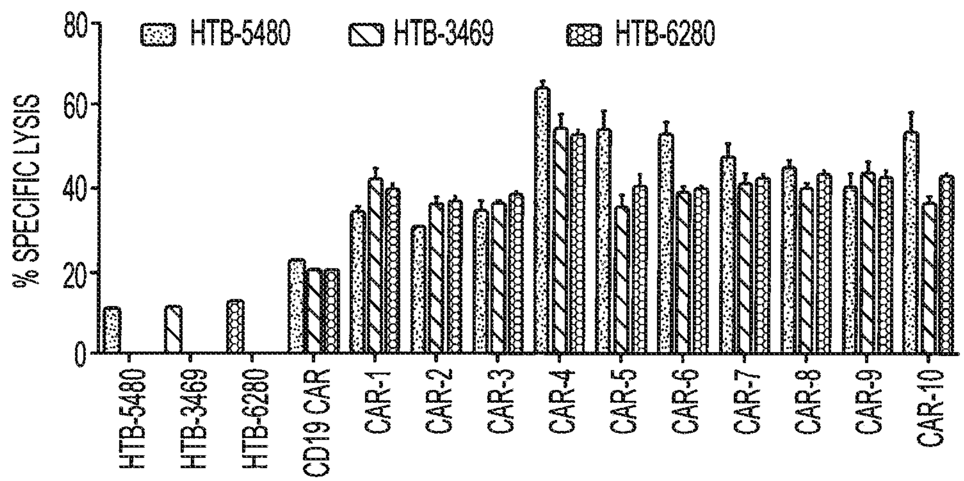

FIG. 25. In vitro lysis of LSCs by chimeric CAR T cells under hypoxia. lin$^{neg}$ CD34$^+$CD38$^{neg}$ fraction was isolated from relapsed AML patients cultured at 1% oxygen and 5% $CO_2$ in presence SR1 supplemented by cytokines stem cell factor (SCF), human FLT3 ligand, interleukin-3 for 7 days. SR1 non treated cells used as control. On day 7, LSCs were labeled with PKH26 and co-cultured with CD123-specific chimeric CAR T cells in 1:1 ratio for 48 hours under hypoxic conditions. CD19 CAR T cells used as negative control.

Figure 26A:
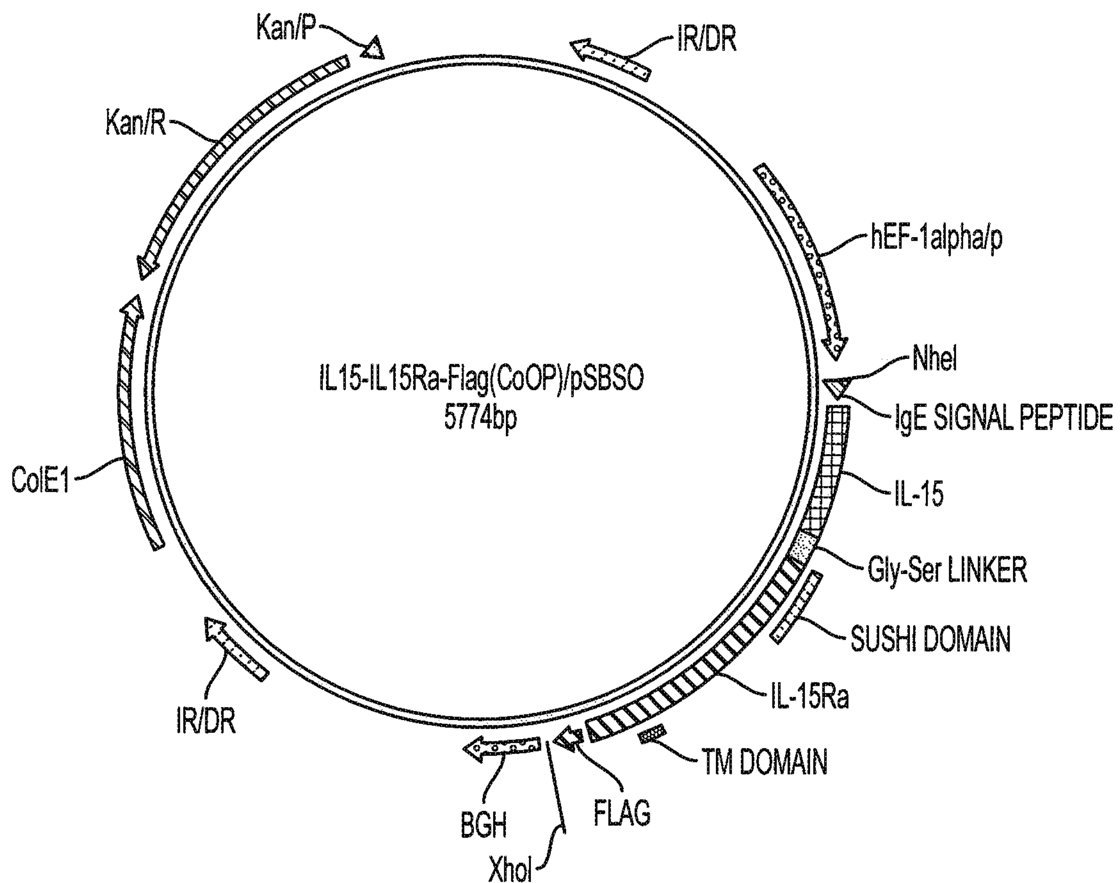
Figure 26B:
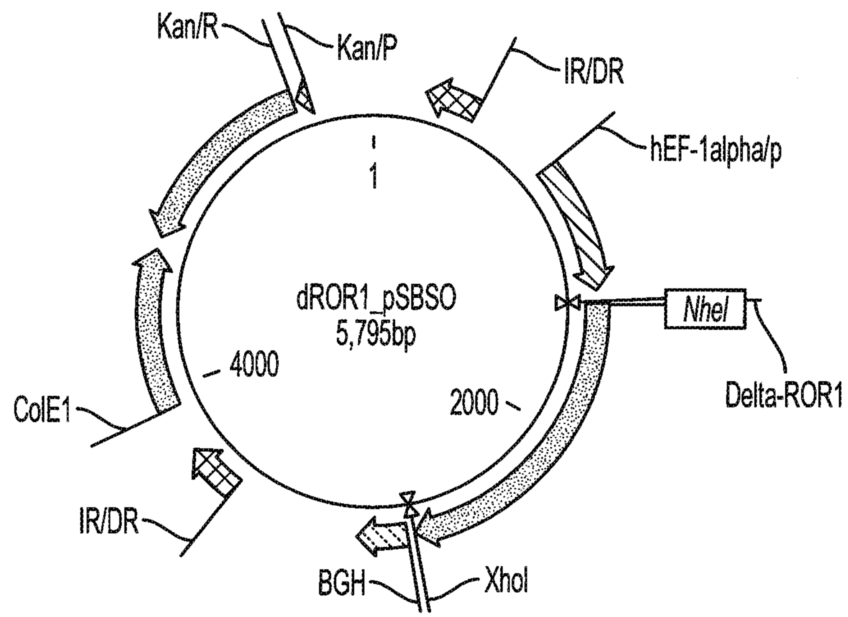
Figure 26C:
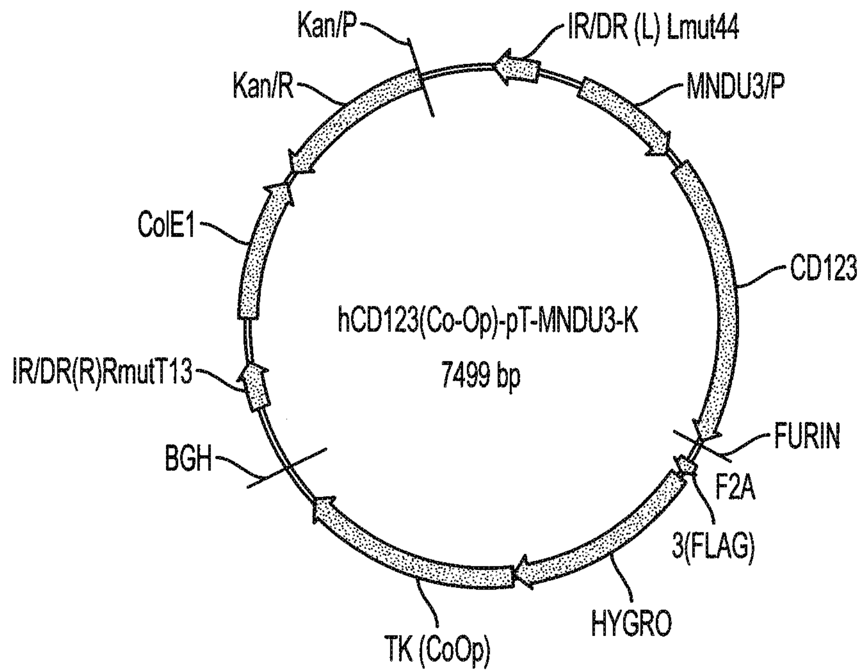

FIGS. 26A-C. Schematics of miL15 and exemplar plasmid vector maps of the embodiments. (A) Sleeping Beauty DNA transposon map for miL15 [IL15-IL15Ra-Flag (CoOp)/pSBSO]. IL-15 is fused with full-length IL-15Rα. hEF-1alpha/p: human elongation factor-1 alpha promoter, TM: transmembrane domain, BGH: polyadenylation signal from bovine growth hormone, IR/DR: Sleeping beauty Inverted Repeats/Direct Repeats, ColE1: *E. coli* origin of replication, Kan/R: gene encoding kanamycin resistance for bacterial selection, Kan/p: prokaryotic promoter. (B) DNA plasmid vector map of Sleeping Beauty transposon expressing the ROR1 antigen. IR/DR: Sleeping beauty Inverted Repeats/Direct Repeats, BGH polyA: Bovine growth hormone polyadenylation sequence, ColE1: A minimal *E. coli* origin of replication, Kan/R: Bacterial selection gene encoding kanamycin resistance, Kan/p: Prokaryotic promoter. (C) DNA plasmid vector map of Sleeping Beauty transposon expressing the CD123 antigen. IR/DR: Sleeping beauty Inverted Repeats/Direct Repeats, MNDU3/P: modified myeloproliferative sarcoma virus long terminal repeat enhancer-promoter, CD123: Human codon-optimized CD123 antigen fused to a hygromycin resistance gene through FLAG and a furin/F2A peptide linker. TK: codon-optimized thymidine kinase gene, BGH polyA: Bovine growth hormone polyadenylation sequence, ColE1: A minimal *E. coli* origin of replication, Kan/R: Bacterial selection gene encoding kanamycin resistance, Kan/p: Prokaryotic promoter.

DESCRIPTION OF ILLUSTRATIVE EMBODIMENTS

Therapeutics that employ CAR-expressing cells for targeting or specific antigens (e.g., tumor-associated antigens)

are currently being investigated for the treatment of a variety of disease from cancers to infectious disease.

I. Definitions

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used herein, the term "antigen" is a molecule capable of being bound by an antibody or T-cell receptor. An antigen is additionally capable of inducing a humoral immune response and/or cellular immune response leading to the production of B and/or T lymphocytes.

As used herein the term "engineered" refers to a composition that has been modified from its naturally occurring form. The modification can be a genetic or a chemical modification. For example, an engineered nucleic acid sequence can comprise at least one amino acid deletion, insertion or substitution relative to naturally occurring molecules or may be linked to heterologous nucleic acid sequence.

As used herein, the term "engineered cell" or "genetically engineered cell" is used to indicate a cell that comprises at least a first nucleic acid molecule that is not found in a corresponding wild type cell or that is inserted in the genome at position that is not found in a wild type cell. For example, an engineered cell may comprise nucleic acid expression vector that is integrated into the genome of cells or present as an extrachromosomal genetic element.

As used herein the term "CD123" refers to the interleukin 3 receptor, alpha (IL3RA; HomoloGene reference number 48088) a membrane receptor polypeptide that is preferentially expressed on certain types of pluripotent stem cells and cancer cells, such as leukemia cancer cells (e.g., acute myeloid leukemia cells).

As used herein the term "anti-tumor effective amount" refers to an effective amount of CAR-expressing immune effector cells to reduce cancer cell or tumor growth or to decrease tumor volume or number of tumor cells in a subject. "An anti-tumor effective amount" can also refer to an effective amount of CAR-expressing immune effector cells to increase life expectancy or to alleviate physiological effects associated with the tumor or cancer.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

II. Chimeric Antigen Receptors and Components

Chimeric antigen receptor molecules are recombinant fusion protein and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv) afford the additional advantage of being "universal" in that they bind native antigen on the target cell surface in an HLA-independent fashion.

A chimeric antigen receptor according to the embodiments can be produced by any means known in the art, though preferably it is produced using recombinant DNA techniques. A nucleic acid sequence encoding the several regions of the chimeric antigen receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic or autologous immune effector cells.

Embodiments of the CARs described herein include nucleic acids encoding an antigen-specific chimeric antigen receptor (CAR) polypeptide, including a comprising an intracellular signaling domain, a transmembrane domain, and an extracellular domain comprising one or more signaling motifs. In certain embodiments, the CAR may recognize an epitope comprised of the shared space between one or more antigens. In some embodiments, the chimeric antigen receptor comprises: a) an intracellular signaling domain, b) a transmembrane domain, and c) an extracellular domain comprising an antigen binding domain. Optionally, a CAR can comprise a hinge domain positioned between the transmembrane domain and the antigen binding domain. In certain aspects, a CAR of the embodiments further comprises a signal peptide that directs expression of the CAR to the cell surface. For example, in some aspects, a CAR can comprise a signal peptide from GM-CSF.

In certain embodiments, the CAR can also be co-expressed with a membrane-bound cytokine to improve persistence when there is a low amount of tumor-associated antigen. For example, CAR can be co-expressed with membrane-bound IL-15.

Depending on the arrangement of the domains of the CAR and the specific sequences used in the domains, immune effector cells expressing the CAR may have different levels activity against target cells. In some aspects, different CAR sequences may be introduced into immune effector cells to generate engineered cells, the engineered cells selected for elevated SRC and the selected cells tested for activity to identify the CAR constructs predicted to have the greatest therapeutic efficacy.

A. Antigen Binding Domain

In certain embodiments, an antigen binding domain can comprise complementary determining regions of a monoclonal antibody, variable regions of a monoclonal antibody, and/or antigen binding fragments thereof. In another embodiment, that specificity is derived from a peptide (e.g., cytokine) that binds to a receptor. A "complementarity determining region (CDR)" is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs.

Because most sequence variation associated with immunoglobulins and T-cell receptors are found in the CDRs, these regions are sometimes referred to as hypervariable domains. Among these, CDR3 shows the greatest variability as it is encoded by a recombination of the VJ (VDJ in the case of heavy chain and TCR αβ chain) regions.

It is contemplated that the CAR nucleic acids, in particular the scFv sequences are human genes to enhance cellular immunotherapy for human patients. In a specific embodiment, there is provided a full length CAR cDNA or coding region. The antigen binding regions or domains can comprise a fragment of the VH and VL chains of a single-chain variable fragment (scFv) derived from a particular mouse, or human or humanized monoclonal antibody. The fragment can also be any number of different antigen binding domains of an antigen-specific antibody. In a more specific embodiment, the fragment is an antigen-specific scFv encoded by a sequence that is optimized for human codon usage for expression in human cells. In certain aspects, VH and VL domains of a CAR are separated by a linker sequence, such as a Whitlow linker. CAR constructs that may be modified or used according to the embodiments are also provided in International (PCT) Patent Publication No. WO/2015/123642, incorporated herein by reference. In several aspects, the VH domain of the CAR may comprise SEQ ID NOs: 1, 3, 5, or 7, or a sequence 85%, 90%, or 95% identical to SEQ ID NOs: 1, 3, 5, or 7. In other aspects, the VL domain of the CAR may comprise SEQ ID NO: 2, 4, 6, or 8, or a sequence 85%, 90%, or 95% identical to SEQ ID NOs: 2, 4, 6, or 8.

As previously described, the prototypical CAR encodes a scFv comprising VH and VL domains derived from one monoclonal antibody (mAb), coupled to a transmembrane domain and one or more cytoplasmic signaling domains (e.g. costimulatory domains and signaling domains). Thus, a CAR may comprise the LCDR1-3 sequences and the HCDR1-3 sequences of an antibody that binds to an antigen of interest, such as tumor associated antigen. In further aspects, however, two of more antibodies that bind to an antigen of interest are identified and a CAR is constructed that comprises: (1) the HCDR1-3 sequences of a first antibody that binds to the antigen; and (2) the LCDR1-3 sequences of a second antibody that binds to the antigen. Such a CAR that comprises HCDR and LCDR sequences from two different antigen binding antibodies may have the advantage of preferential binding to particular conformations of an antigen (e.g., conformations preferentially associated with cancer cells versus normal tissue).

In some specific examples the antigen binding domain of a CAR comprises the LCDR1-3 and HCDR1-3 or VH and VL sequences from the 26292 antibody, the 32701 antibody, the 32703 antibody, or the 32716 antibody.

Alternatively, it is shown that a CAR may be engineered using VH and VL chains derived from different mAbs to generate a panel of CAR+ T cells. The antigen binding domain of a CAR can contain any combination of the LCDR1-3 sequences of a first antibody and the HCDR1-3 sequences of a second antibody. For example, a CAR may comprise the LCDR1-3 sequences from the 26292 antibody and HCDR1-3 sequences from the 32701 antibody or the LCDR1-3 sequences from the 32701 antibody and HCDR1-3 sequences from the 32716 antibody. For example, the antigen binding domain may be comprised according to the combinations listed in Table A below.

Table A. Possible sequence combinations of the antigen binding domain.

26292 VH domain (SEQ ID NO: 1)+26292 VL domain (SEQ ID NO: 2)

26292 VH domain (SEQ ID NO: 1)+32703 VL domain (SEQ ID NO: 4)

26292 VH domain (SEQ ID NO: 1)+32701 VL domain (SEQ ID NO: 6)

26292 VH domain (SEQ ID NO: 1)+32716 VL domain (SEQ ID NO: 8)

32703 VH domain (SEQ ID NO: 3)+26292 VL domain (SEQ ID NO: 2)

32703 VH domain (SEQ ID NO: 3)+32703 VL domain (SEQ ID NO: 4)

32703 VH domain (SEQ ID NO: 3)+32701 VL domain (SEQ ID NO: 6)

32703 VH domain (SEQ ID NO: 3)+32716 VL domain (SEQ ID NO: 8)

32701 VH domain (SEQ ID NO: 5)+26292 VL domain (SEQ ID NO: 2)

32701 VH domain (SEQ ID NO: 5)+32703 VL domain (SEQ ID NO: 4)

32701 VH domain (SEQ ID NO: 5)+32701 VL domain (SEQ ID NO: 6)

32701 VH domain (SEQ ID NO: 5)+32716 VL domain (SEQ ID NO: 8)

32716 VH domain (SEQ ID NO: 7)+26292 VL domain (SEQ ID NO: 2)

32716 VH domain (SEQ ID NO: 7)+32703 VL domain (SEQ ID NO: 4)

32716 VH domain (SEQ ID NO: 7)+32701 VL domain (SEQ ID NO: 6)

32716 VH domain (SEQ ID NO: 7)+32716 VL domain (SEQ ID NO: 8)

In some specific examples, a CD123 CAR may comprise the HCDR1-3 sequences of the 26292 antibody (SEQ ID NOs: 21, 22 and 23) and the LCDR1-3 sequences of: the 32703 antibody (SEQ ID NOs: 30, 31 and 32); the 32701 antibody (SEQ ID NOs: 36, 37 and 38); or the 32716 antibody (SEQ ID NOs: 42, 43 and 44). In a further aspect, a CD123 CAR comprises the HCDR1-3 sequences of the 32703 antibody (SEQ ID NOs: 27, 28 and 29) and the LCDR1-3 sequences of: the 26292 antibody (SEQ ID NOs: 24, 25 and 26); the 32701 antibody (SEQ ID NOs: 36, 37 and 38); or the 32716 antibody (SEQ ID NOs: 42, 43 and 44). In a further aspect, a CD123 CAR comprises the HCDR1-3 sequences of the 32701 antibody (SEQ ID NOs: 33, 34 and 35) and the LCDR1-3 sequences of: the 26292 antibody (SEQ ID NOs: 24, 25 and 26); the 32703 antibody (SEQ ID NOs: 30, 31 and 32); or the 32716 antibody (SEQ ID NOs: 42, 43 and 44). In yet a further aspect, a CD123 CAR may comprise the HCDR1-3 sequences of the 32716 antibody (SEQ ID NOs: 39, 40 and 41) and the LCDR1-3 sequences of: the 26292 antibody (SEQ ID NOs: 24, 25 and 26); the 32703 antibody (SEQ ID NOs: 30, 31 and 32); or the 32701 antibody (SEQ ID NOs: 36, 37 and 38).

B. Hinge Domain

In certain aspects, a CAR polypeptide of the embodiments can include a hinge domain positioned between the antigen binding domain and the transmembrane domain. In some cases, a hinge domain may be included in CAR polypeptides to provide adequate distance between the antigen binding domain and the cell surface or to alleviate possible steric hindrance that could adversely affect antigen binding or effector function of CAR-gene modified T cells. In some aspects, the hinge domain comprises a sequence that binds to an Fc receptor, such as FcγR2a or FcγR1a. For example, the hinge sequence may comprise an Fc domain from a human immunoglobulin (e.g., IgG1, IgG2, IgG3, IgG4, IgA1, IgA2, IgM, IgD or IgE) that binds to an Fc receptor.

In certain aspects, the hinge domain (and/or the CAR) does not comprise a wild type human IgG4 CH2 and CH3 sequence.

In some cases the CAR hinge domain could be derived from human immunoglobulin (Ig) constant region or a portion thereof including the Ig hinge, or from human CD8α transmembrane domain and CD8a-hinge region. In one aspect, the CAR hinge domain can comprise a hinge-$CH_2$—$CH_3$ region of antibody isotype $IgG_4$. In some aspects, point mutations could be introduced in antibody heavy chain $CH_2$ domain to reduce glycosylation and non-specific Fc gamma receptor binding of CAR-T cells or any other CAR-modified cells.

In certain aspects, a CAR hinge domain of the embodiments comprises an Ig Fc domain that comprises at least one mutation relative to wild type Ig Fc domain that reduces Fc-receptor binding. For example, the CAR hinge domain can comprise an IgG4-Fc domain that comprises at least one mutation relative to wild type IgG4-Fc domain that reduces Fc-receptor binding. In some aspects, a CAR hinge domain comprises an IgG4-Fc domain having a mutation (such as an amino acid deletion or substitution) at a position corresponding to L235 and/or N297 relative to the wild type IgG4-Fc sequence. For example, a CAR hinge domain can comprise an IgG4-Fc domain having a L235E and/or a N297Q mutation relative to the wild type IgG4-Fc sequence. In further aspects, a CAR hinge domain can comprise an IgG4-Fc domain having an amino acid substitution at position L235 for an amino acid that is hydrophilic, such as R, H, K, D, E, S, T, N or Q or that has similar properties to an "E" such as D. In certain aspects, a CAR hinge domain can comprise an IgG4-Fc domain having an amino acid substitution at position N297 for an amino acid that has similar properties to a "Q" such as S or T.

In certain specific aspects, the hinge domain comprises a sequence that is about 85%, 90%, 91%, 92%, 93%, 94%, 95%, 96%, 97%, 98%, 99% or 100% identical to an IgG4 hinge domain of SEQ ID NO: 13, a CD8a hinge domain of SEQ ID NO: 12, a CD28 hinge domain or an engineered hinge domain such as SEQ ID NO: 45 (ESKYGPPCPPCP).

C. Transmembrane Domain

The antigen-specific extracellular domain and the intracellular signaling-domain may be linked by a transmembrane domain. Polypeptide sequences that can be used as part of transmembrane domain include, without limitation, the human CD4 transmembrane domain, the human CD28 transmembrane domain, the transmembrane human CD3ζ domain, or a cysteine mutated human CD3ζ domain, or other transmembrane domains from other human transmembrane signaling proteins, such as CD16 and CD8 and erythropoietin receptor. In some aspects, for example, the transmembrane domain comprises a sequence at least 85%, 90%, 91%, 92%, 93%, 94%, 95%, 96%, 97%, 98%, 99% or 100% identical to one of those provided in U.S. Patent Publication No. 2014/0274909 (e.g. a CD8 and/or a CD28 transmembrane domain) or U.S. Pat. No. 8,906,682 (e.g. a CD8a transmembrane domain), both incorporated herein by reference. Transmembrane regions of particular use in this invention may be derived from (i.e. comprise at least the transmembrane region(s) of) the alpha, beta or zeta chain of the T-cell receptor, CD3 epsilon, CD45, CD4, CD5, CD8, CD9, CD16, CD22, CD33, CD37, CD64, CD80, CD86, CD134, CD137, CD154. In certain specific aspects, the transmembrane domain can be 85%, 90%, 91%, 92%, 93%, 94%, 95%, 96%, 97%, 98%, 99% or 100% identical to a CD8a transmembrane domain of SEQ ID NO: 14 or a CD28 transmembrane domain of SEQ ID NO: 15.

D. Intracellular Signaling Domain

The intracellular signaling domain of the chimeric antigen receptor of the embodiments is responsible for activation of at least one of the normal effector functions of the immune cell engineered to express a chimeric antigen receptor. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus the term "intracellular signaling domain" refers to the portion of a protein that transduces the effector function signal and directs the cell to perform a specialized function. In some aspects, the intracellular signaling domain is derived from the intracellular signaling domain of a native receptor. Examples of such native receptors include the zeta chain of the T-cell receptor or any of its homologs (e.g., eta, delta, gamma, or epsilon), MB 1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins can be used, such as FcγRIII and FcεRI. See Gross et al. (1992), Stancovski et al. (1993), Moritz et al. (1994), Hwu et al. (1995), Weijtens et al. (1996), and Hekele et al. (1996) for disclosures of T-cell receptors using these alternative transmembrane and intracellular domains. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term "intracellular signaling domain" is thus meant to include a truncated portion of the intracellular signaling domain sufficient to transduce the effector function signal, upon CAR binding to a target. In a preferred embodiment, the human CD3ζ intracellular domain is used as the intracellular signaling domain for a CAR of the embodiments.

In specific embodiments, intracellular receptor signaling domains in the CAR include those of the T cell antigen receptor complex, such as the ζ chain of CD3, also Fcγ RIII costimulatory signaling domains, CD28, CD27, DAP10, CD137, OX40, CD2, alone or in a series with CD3ζ, for example. In specific embodiments, the intracellular domain (which may be referred to as the cytoplasmic domain) comprises part or all of one or more of TCRζ chain, CD28, CD27, OX40/CD134, 4-1BB/CD137, FcεRIγ, ICOS/CD278, IL-2Rβ/CD122, IL-2Rα/CD132, DAP10, DAP12, and CD40. In some embodiments, one employs any part of the endogenous T cell receptor complex in the intracellular domain. One or multiple cytoplasmic domains may be employed, as so-called third generation CARs have at least two or three signaling domains fused together for additive or synergistic effect, for example the CD28 and 4-1BB can be combined in a CAR construct.

In some embodiments, the CAR comprises additional other costimulatory domains. Other costimulatory domains can include, but are not limited to one or more of CD28, CD27, OX-40 (CD134), DAP10, and 4-1BB (CD137). In addition to a primary signal initiated by CD3ζ, an additional signal provided by a human costimulatory receptor inserted in a human CAR is important for full activation of T cells and could help improve in vivo persistence and the therapeutic success of the adoptive immunotherapy.

In certain specific aspects, the intracellular signaling domain comprises a sequence 85%, 90%, 91%, 92%, 93%, 94%, 95%, 96%, 97%, 98%, 99% or 100% identical to a CD3ζ intracellular domain of SEQ ID NO: 16, a CD28 intracellular domain of SEQ ID NO: 46, a CD137 intracellular domain of SEQ ID NO: 47 or a domain comprising a CD28 intracellular domain fused to the 4-1BB intracellular domain.

III. Vectors and Cell Engineering

In particular embodiments, isolated nucleic acid segments and expression cassettes incorporating DNA sequences that encode polypeptide coding sequence or an open reading frame (ORF) are provided. For example, the ORF can encode a CAR polypeptide. In further aspects, an ORF encodes a target antigen (or an epitope thereof) and/or a HLA polypeptide. In further aspects, an ORF encodes mitochondrial reporter gene, such a reporter polypeptide (e.g., a fluorescent reporter) comprising a mitochondria localization signal.

As will be appreciated by one of skill in the art that, in some instances, the coding sequence for a few amino acids at the ends of an encoded ORF may be deleted. For example, in the case of an ORF encoding a CAR, the coding sequence for a few amino acids of the antigen binding domain in the CAR can be deleted without affecting either specificity or effector binding affinity of the molecules, usually not more than 10, more usually not more than 5 residues, for example. Also, it may be desirable to introduce a small number of amino acids encoded at the borders of a polypeptide coding sequence, usually not more than 10, more usually not more than 5 residues. The deletion or insertion of amino acids may be as a result of the needs of the construction, providing for convenient restriction sites, ease of manipulation, improvement in levels of expression, or the like. In addition, the substitute of one or more amino acids with a different amino acid can occur for similar reasons, usually not substituting more than about 5 amino acids in a polypeptide coding sequence (e.g., in any domain of a CAR).

The engineered constructs according to the embodiments can be prepared in conventional ways. Native sequences may be employed and the native genes may be isolated and manipulated, as appropriate, so as to allow for the proper joining of the various components to arrive at a chimeric construct. For example, in the case of a CAR, the nucleic acid sequences encoding for the N-terminal and C-terminal protein components of the chimeric antigen receptor can be isolated by employing the polymerase chain reaction (PCR), using appropriate primers that result in deletion of the undesired portions of the gene. Alternatively, restriction digests of cloned genes can be used to generate the chimeric construct. In either case, the sequences can be selected to provide for restriction sites that are blunt-ended, or have complementary overlaps.

The various manipulations for preparing the engineered construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to ensure that the sequence encodes the desired polypeptide (e.g., a chimeric antigen receptor) and expression control sequences. The sequence can be screened by restriction analysis, sequencing, or the like.

Vectors of the embodiments designed, primarily, to deliver desired genes to immune cells, preferably immune effector cells (e.g., T cells) or APCs, under the control of regulated eukaryotic promoters. Promoters that can be used according to the embodiments include, for example, MNDU3 promoter, CMV promoter, EF1α promoter, or Ubiquitin promoter. Also, the vectors may contain a selectable marker, to facilitate their manipulation in vitro. In other embodiments, the gene of interest (e.g., a CAR) can be expressed from mRNA in vitro transcribed from a DNA template.

In an exemplary nucleic acid construct (polynucleotide) employed according to the embodiments, the promoter is operably linked to the nucleic acid sequence encoding a gene (e.g., a CAR) of the embodiments, i.e., they are positioned so as to promote transcription of the messenger RNA from the DNA encoding the gene. The promoter can be of genomic origin or synthetically generated. A variety of promoters for use in T cells are well-known in the art (e.g., the CD4 promoter disclosed by Marodon et al. (2003)). The promoter can be constitutive or inducible, where induction is associated with the specific cell type or a specific level of maturation, for example. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the gene can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld, 2003). Also, it may be further advantageous to use endogenous or exogenous non-coding regions to stabilize the mRNA.

For expression of a gene of the embodiments, the naturally occurring or endogenous transcriptional initiation region of the nucleic acid sequence encoding gene can be used to generate the chimeric antigen receptor in the target host. Alternatively, an exogenous transcriptional initiation region can be used that allows for constitutive or inducible expression (e.g., a tet-on or tet-off promoter system), wherein expression can be controlled depending upon the target host, the level of expression desired, the nature of the target host, and the like.

Likewise, in some cases, a signal sequence directing the polypeptide encoded by the gene to the cell surface may be used. In some cases, the signal sequence is the signal sequence present in the native version of a gene. Optionally, in some instances, it may be desirable to exchange this sequence for a different signal sequence. However, the signal sequence selected should be compatible with the secretory pathway of the cell used for expression of the gene (e.g., in T cells) so that the polypeptide is presented on the surface of the cell.

Similarly, a termination region may be provided by the naturally occurring or endogenous transcriptional termination region for the native version of the gene. Alternatively, the termination region may be derived from a different source. For the most part, the source of the termination region is generally not considered to be critical to the expression of a recombinant protein and a wide variety of termination regions can be employed without adversely affecting expression.

It is contemplated that genetic constructs, such as CAR expression constructs, can be introduced into the subject's own cells, i.e. autologous cells (or into cells from a different donor subject; i.e. allogenic cells) as naked DNA or in a suitable vector. Methods of stably transfecting cells, such as T cells, by electroporation using naked DNA are known in the art. See, for example, U.S. Pat. No. 6,410,319, incorporated herein by reference. Naked DNA generally refers to the DNA encoding a gene (e.g., chimeric antigen receptor) of the present embodiments contained in a plasmid expression vector in proper orientation for expression. Advantageously, the use of naked DNA can reduce the time required to produce cells expressing the gene of the embodiments.

In further aspects, genetic constructs can be introduced into cells using a transposon-based system to mediate integration of the gene (e.g., encoding a CAR) construct into genomic DNA of the cells. Generally, such methods will involve introducing into cells (i) a first vector encoding the transposase (or a transposase polypeptide) and (ii) a second vector encoding a desired gene expression element that is flanked by transposon repeats. Transposons or transposable elements include a (short) nucleic acid sequence with terminal repeat sequences upstream and downstream thereof and encode enzymes that facilitate the excision and insertion of the nucleic acid into target DNA sequences. Several transposon/transposase systems have been adapted for genetic insertions of heterologous DNA sequences, including Sleeping Beauty (SB), a Tc1/mariner-like element from fish that exhibits transpositional activity in a variety of vertebrate cultured cell lines, embryonic stem cells and in vivo (Ivics et al., 1997). In some aspects, the transposase is provided as DNA expression vector. In certain aspects, the transposase is provided as an expressible RNA or a protein such that long-term expression of the transposase does not occur in the engineered cells. For example, in some aspects, the transposase is provided as encoded by an mRNA (e.g., an mRNA comprising a cap and poly-A tail). Additional transposases and transposon systems are provided in U.S. Pat. Nos. 6,489,458; 7,148,203; 8,227,432; U.S. Patent Publn. No. 2011/0117072; Mates et al., 2009 and in Ivics et al., 1997, each of which are incorporated herein by reference in their entirety.

Alternatively, a viral vector (e.g., a retroviral vector, adenoviral vector, adeno-associated viral vector, or lentiviral vector) can be used to introduce the genes into cells. Suitable vectors for use in accordance with the method of the embodiments are non-replicating in the subject's cells. A large number of vectors are known that are based on viruses, where the copy number of the virus maintained in the cell is low enough to maintain the viability of the cell. Illustrative vectors include the pFB-neo vectors (STRATAGENE®) disclosed herein as well as vectors based on HIV, SV40, EBV, HSV, or BPV.

IV. Immune Effector Cells

In certain aspects, the embodiments described herein include methods of making and/or expanding the antigen-specific redirected immune effector cells (e.g., T-cells, NK-cell or NK T-cells) that comprises transfecting the cells with an expression vector containing a DNA (or mRNA) construct encoding the CAR, then, optionally, stimulating the cells with feeder cells, recombinant antigen, or an antibody to the receptor to cause the cells to proliferate. In certain aspects, the cell (or cell population) engineered to express a CAR is a stem cell, iPS cell, immune cell or a precursor of these cells. Methods described below address the specific example of T-cells (or other immune cell) engineering for CAR expression.

Sources of immune effector cells include both allogeneic and autologous sources. In some cases, immune effector cells may be differentiated from stem cells or induced pluripotent stem cells (iPSCs). Thus, cell(s) for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells, such as T cells derived from human peripheral blood mononuclear cells (PBMC), PBMC collected after stimulation with G-CSF, bone marrow, or umbilical cord blood. Following transfection or transduction (e.g., with a CAR expression construct), the cells may be immediately infused or may be stored. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be deleted on artificial antigen presenting cell or with an antibody, such as Campath, which binds CD52 on the T cell surface. In a further aspect, the genetically modified cells may be cryopreserved.

In further aspects, immune effector cells of the embodiment have been selected for high mitochondrial spare respiratory capacity (SRC). As used herein an "immune effector cell having high mitochondrial SRC" refers to an immune effector cell (e.g., a T-cell) having higher mitochondria activity or mitochondria number than a corresponding average immune effector cell (e.g., a T-cell). Thus, in some aspects, a cell composition of the embodiments comprises a population of immune effector cells having high mitochondrial SRC, for example a population of CAR-expressing T-cell having high mitochondrial SRC.

Immune effector cells, such as $CD8^+$ T cells, with high mitochondrial SRC may exhibit enhanced survival relative to cells with lower SRC during stress conditions, such as high tumor burden, hypoxia, lack of nutrients for glycolysis, or a suppressive cytokine milieu. Moreover, immune effector cells selected for high mitochondrial SRC may retain cytotoxic activity, even under stress conditions. Accordingly, by selecting immune effector cells with high mitochondrial SRC improved cell composition for both therapy and for testing of CAR constructs can be produced.

In one aspect, engineered immune effector cells are provided that comprise a reporter that can be used to determine the mitochondrial SRC of the engineered effector cells. For example, engineered cells may comprise a reporter polypeptide that is linked to a mitochondria localization signal. For example, the reporter can be a fluorescent polypeptide such an enhanced Yellow Fluorescence Protein (YFP) or an enhanced Green Fluorescence Protein (EGFP) and the mitochondria localization signal can be from glutaredoxin (Grx2). In this context the fluorescence reporter identifies CAR+ T cells with high mitochondrial SRC. For example, the engineered cells expressing the reporter can be sorted based on intensity fluorescence and infused for tumor killing in vivo. Likewise, the engineered cells could be tested for ex vivo killing of target cells to determine, for example, the therapeutic effectiveness of a candidate CAR polypeptide.

In some aspects, the mitochondrial reporter gene for use according to the embodiments may be an endogenous gene. In further aspects, the mitochondrial reporter gene may be an exogenous gene, such as a gene encoding a fluorescent reporter protein. In some aspects, the fluorescent reporter protein may comprise a mitochondrial localization sequence. In certain aspects, a method for selecting immune effector cells having high SRC may comprise flow cytometry or FACS.

In certain aspects, expression of the reporter gene for identifying immune effector cells with SRC may be under the control of a nuclear promoter (e.g., hEFla). In certain aspects, expression of the reporter gene may be under the control of a mitochondrial promoter. In certain aspects, the expressed reporter protein may comprise a mitochondrial localization sequence. In certain aspects, the expressed reporter protein may be directed to the cell surface. In certain aspects, expression of the reporter gene may be under the control of a mitochondrial promoter and the expressed reporter protein may be directed to the cell surface. In some aspects, an exogenous reporter gene may be flanked by a transposon repeat or a viral LTR. In some aspects, an exogenous reporter gene may be comprised in an extrachromosomal nucleic acid, such as an mRNA or an episomal vector.

V. Method for Propagating Immune Effector Cells

In some cases, immune effector cells of the embodiments (e.g., T-cells) are co-cultured with activating and propagating cells (AaPCs), to aid in cell expansion. For example, antigen presenting cells (APCs) are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated by reference.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in International (PCT) Patent Pub. no. WO/2014/190273, which is incorporated herein by reference. In addition to peptide-MHC molecules or antigens of interest, the AaPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2 (see Kim et al., 2004). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs may be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs may be frozen and stored for an extended period of time prior to thawing. Frozen AaPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, may be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain cases, CAR modified cells can be sorted based on their mitochondrial strength (or total mitochondria content of the cells) by employing a fluorescent reporter protein using FACS prior to use as a therapeutic.

VI. Engineered Antigen Presenting Cells

In certain embodiments there are further provided an engineered antigen presenting cell (APC). Such cells may be used, for example, as described above, to propagate immune effector cells ex vivo. In further aspects, engineered ACPs may, themselves be administered to a patient and thereby stimulate expansion of immune effector cells in vivo. Engineered APCs of the embodiments may, themselves, be used as a therapeutic agent. In some embodiments, the engineered APCs can be used as a therapeutic agent that can stimulate activation of endogenous immune effector cells specific for a target antigen and/or to increase the activity or persistence of adoptively transferred immune effector cells specific to a target antigen.

As used herein the term "engineered APC" refers to a cell(s) that comprises at least a first introduced gene encoding a human leukocyte antigen (HLA). Such engineered APCs may further comprise a second gene for expression of an antigen, such that the antigen is presented at the surface on the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as "T-APC"). Thus, in some aspects, an engineered APC of the embodiments comprises a first gene encoding a target antigen and a second gene encoding a HLA, such that the HLA is expressed on the surface of the engineered APC in complex with an epitope of the target antigen. In certain specific aspects, the HLA expressed in the engineered APC is a HLA-A, HLA-B, HLA-C or HLA-DRB 1. In further aspects, the HLA expressed in the engineered APC is HLA-A2.

In some aspects, an engineered APC of the embodiments may further comprise at least a third gene encoding co-stimulatory molecule. The co-stimulatory molecule may be a co-stimulatory cytokine that may be a membrane-bound Cy cytokine. In certain aspects, the co-stimulatory cytokine is IL-15, such as membrane-bound IL-15. In some further aspects, an engineered APC may comprise an edited (or deleted) gene. For example, an inhibitory gene, such as PD-1, LIM-3, CTLA-4 or a TCR, can be edited to reduce or eliminate expression of the gene.

An engineered APC of the embodiments may comprise a gene encoding any target antigen of interest. For example, the target antigen can be an infectious disease antigen or a tumor-associated antigen (TAA). Target antigens may be intracellular or cell surface antigens. For example, in some aspects, the target antigen is a TAA such as a TAA derived from a subcellular compartment of the tumor cell. The TAA may be membrane-bound, cytoplasmic, nuclear-localized, or even secreted by the tumor cells. In some aspects, the TAA is differentially expressed compared to the corresponding normal tissue thereby allowing for a preferential recognition of tumor cells by immune effector cells. Specific examples of target antigens include, without limitation, WT1, MUC1, LMP2, HPV E6 E7, EGFRvIII, HER-2/neu, Idiotype, MAGE A3, p53 nonmutant, NY-ESO-1, PSMA, GD2, CEA, MelanA/MART1, Ras mutant, gpl00, p53 mutant, Proteinase3 (PR1), bcr-abl, Tyrosinase, Survivin, PSA, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic acid, MCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OT-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, and Fos-related antigen 1.

In some specific aspects, an engineered APC of the embodiments is a T cell that has been engineered to function as antigen presenting cells (referred to as a "T-APC"). In particular, a T-APC of the embodiments comprises a first gene encoding a target antigen and a second gene encoding a HLA. Thus, the T-APC can present the encoded antigen, such as a TAA. For example, T-APCs exemplified herein comprise a gene encoding the NY-ES0-1 antigen and HLA-A2. Thus, these cells may be used to propagate NY-ESO-1-specific immune effector cells either ex vivo or in vivo (after being administered to a patient). Moreover, T-APCs exemplified herein were further engineered to express an additional of co-stimulatory molecule, specifically membrane-bound IL-15 (miL-15). The additional co-stimulatory molecule further improves the generation of target antigen specific immune effector cells and increases the persistence of these cells.

VII. Therapeutic Application

In some aspects, the chimeric antigen receptor constructs and cells of the embodiments find application in subjects having or suspected of having cancer by reducing the size of a tumor or preventing the growth or re-growth of a tumor in these subjects. Accordingly, embodiments provided herein further relate to a method for reducing growth or preventing tumor formation in a subject by introducing a chimeric antigen receptor construct of the present embodiments into an isolated immune effector cell, such as an NK cell or T cell of the subject and reintroducing into the subject the transformed T cell, thereby effecting anti-tumor responses to reduce or eliminate tumors in the subject. Suitable T cells that can be used include cytotoxic lymphocytes (CTL) or any cell having a T cell receptor in need of disruption. As is well-known to one of skill in the art, various methods are readily available for isolating these cells from a subject. For example, using cell surface marker expression or using commercially available kits (e.g., ISOCELL™ from Pierce, Rockford, Ill.).

Once it is established that the transfected or transduced immune effector cell (e.g., T cell) is capable of expressing the chimeric antigen receptor as a surface membrane protein with the desired regulation and at a desired level, it can be determined whether the chimeric antigen receptor is functional in the host cell to provide for the desired signal induction. Subsequently, the transduced immune effector cells are reintroduced or administered to the subject to activate anti-tumor responses in the subject. To facilitate administration, the transduced T cells according to the embodiments can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not ineffectuate the cells expressing the chimeric antigen receptor. Thus, desirably the transduced T cells can be made into a pharmaceutical composition containing a balanced salt solution, preferably Hanks' balanced salt solution, or normal saline.

In certain embodiments, CAR-expressing cells of the embodiments are delivered to an individual in need thereof, such as an individual that has cancer or an infection. The cells then enhance the individual's immune system to attack the respective cancer or pathogen-infected cells. In some cases, the individual is provided with one or more doses of the antigen-specific CAR cells. In cases where the individual is provided with two or more doses of the antigen-specific CAR cells, the duration between the administrations should be sufficient to allow time for propagation in the individual, and in specific embodiments the duration between doses is 1, 2, 3, 4, 5, 6, 7, or more days. Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

A pharmaceutical composition of the embodiments (e.g., comprising CAR-expressing T-cells) can be used alone or in combination with other well-established agents useful for treating cancer. Whether delivered alone or in combination with other agents, the pharmaceutical composition of the embodiments can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be used for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

A composition of the embodiments can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the embodiments, alone or in combination with other active agents, calculated in an amount sufficient to produce the desired effect, in association with a pharmaceutically acceptable diluent, carrier, or vehicle, where appropriate. The specifications for the novel unit dosage forms of the embodiments depend on the particular pharmacodynamics associated with the pharmaceutical composition in the particular subject.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes a 10%, 20%, 30%, 40%, 50%, 60%, 70%, 80%, 90%, 95%, 98%, or 100% decrease in tumor size when compared to otherwise same conditions wherein the transduced T cells are not present. As used herein the term "anti-tumor effective amount" refers to an effective amount of CAR-expressing immune effector cells to reduce cancer cell or tumor growth in a subject.

Accordingly, the amount of transduced immune effector cells (e.g., T cells) administered should take into account the route of administration and should be such that a sufficient number of the transduced immune effector cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of transduced T cells to be utilized by the practitioner upon optimizing the method of the embodiments. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

VII. Kits of the Embodiments

Any of the compositions described herein may be comprised in a kit. In some embodiments, allogeneic CAR T-cells are provided in the kit, which also may include reagents suitable for expanding the cells, such as media, APCs, engineered APCs, growth factors, antibodies (e.g., for sorting or characterizing CAR T-cells) and/or plasmids encoding genes, such as a target antigen, HLA, mitochondrial reporter, CAR or transposase.

In a non-limiting example, a chimeric antigen receptor expression construct, one or more reagents to generate a chimeric antigen receptor expression construct, cells for transfection of the expression construct, and/or one or more instruments to obtain allogeneic cells for transfection of the expression construct (such an instrument may be a syringe, pipette, forceps, and/or any such medically approved apparatus).

In some embodiments, an expression construct for eliminating endogenous TCR $\alpha/\beta$ expression, one or more reagents to generate the construct, and/or CAR+ T cells are provided in the kit. In some embodiments, there includes expression constructs that encode zinc finger nuclease(s).

In some aspects, the kit comprises reagents or apparatuses for electroporation of cells.

The kits may comprise one or more suitably aliquoted compositions of the embodiments or reagents to generate compositions of the embodiments. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the embodiments also will typically include a means for containing the chimeric antigen receptor construct and any other reagent containers in close confinement for commercial sale. Such containers may include injection or blow molded plastic containers into which the desired vials are retained, for example.

VIII. EXAMPLES

The following examples are included to demonstrate preferred embodiments of the invention. However, those of skill in the art should, in light of the present disclosure, appreciate that many changes can be made in the specific embodiments which are disclosed and still obtain a like or similar result without departing from the spirit and scope of the invention.

Example 1—Redirecting Specificity of T Cells to Target CD123$^+$ B-ALL Tumors Adoptive immunotherapy infusing T cells with engineered specificity for CD19 expressed on B-cell malignancies has been successful and the extension of this approach to other hematological malignancies, such as acute myelogenous leukemia (AML), is explored herein. CD123, or interleukin 3 receptor alpha, is overexpressed on most AML and some lymphoid malignancies, such as acute lymphocytic leukemia (ALL), and has been an effective target for T cells expressing CARs.

CARs can empower T cells with an antibody-like specificity and are able to transmit signals leading to T cell activation, proliferation and effector functions upon binding to its specific antigen. The binding chemistry of CAR's scFv with its cognate antigen is not well studied at present. Gross et al. demonstrated that the antigen binding site and idiotope for anti-2, 4, 6-trinitrophenyl (TNP) antibody (SP6) reside exclusively in VH region (86). In general, T cells expressing chimeric antigen receptors (CARs) are generated by combining the variable light (VL) and heavy (VH) chains of scFv derive d from single mAbs specific to targeted antigen (86). Examination of the contribution of VH and VL chains of scFvs specific to targeted antigen may help to better understand the functionality of CARs and to derive CARs with different affinities to targeted antigen. One of the limiting factors in CAR T cell therapy is that TAAs are not tumor "specific" but also expressed at low levels on normal cells and often associated with off tumor toxicities. Recent preclinical studies targeting EGFR and erbB2 with affinity lowered CAR T cells have demonstrated potent antitumor effect on tumors with high antigen density while sparing normal cells (87, 88). The present example describes a new approach for generating CD123-specific CARs derived from a chimeric scFv that is made up of the VL and VH harvested from two mAbs that are each specific for CD123. It was hypothesized that T cells containing chimeric scFvs by mix and matching VH and VL chains of two mAbs would effectively redirect T-cell specificity against CD123-expressing tumor cells. To test this hypothesis, six CARs with chimeric scFvs were generated by mix and matching VH and VL of four mAbs specific to CD123. CARs derived from VH and VL of original mAbs without mix and matching were used as controls. The CARs with the least killing and effector functions in normal hematopietic cells carried forward to target B-ALL (described in present example) and AML (described in Example 2) were selected for further analysis.

Figure 1:
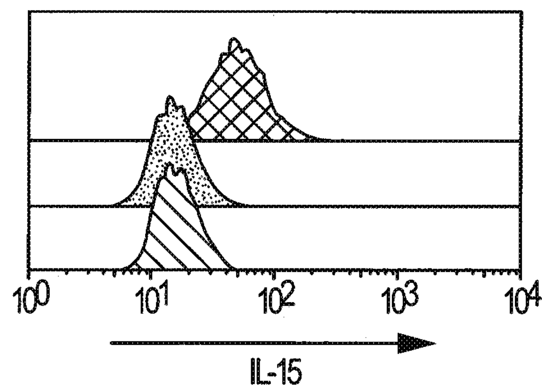
FIG. 1. Surface phenotype of AaPC-Clone 1. Surface expression of IL-15, CD64, CD86, CD137L, CD19 and ROR1 were analyzed by flow cytometry on parental K562 (deep grey histogram) and Clone1 (black histograms) and appropriate isotypes (light grey).
Figure 1:
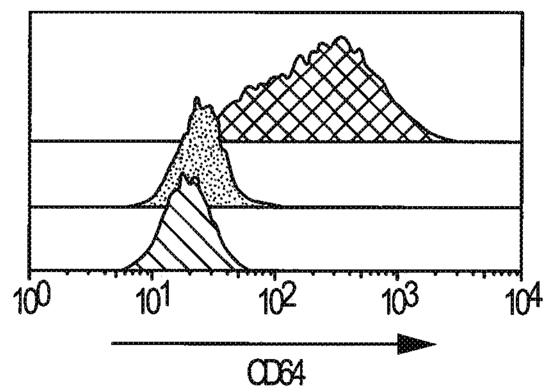
Figure 1:
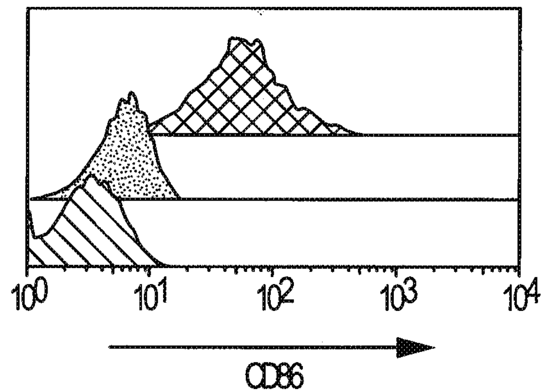
Figure 1:
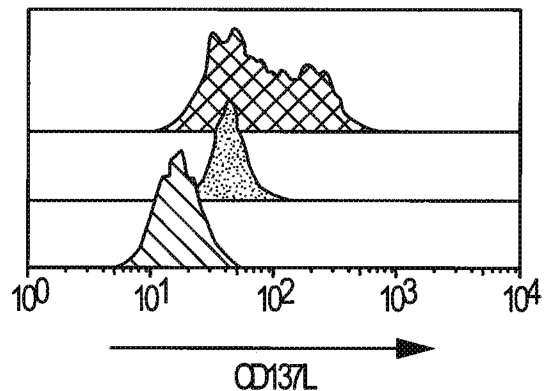
Figure 1:
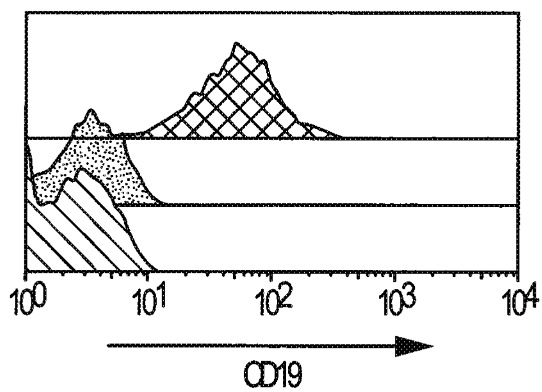
Figure 1:
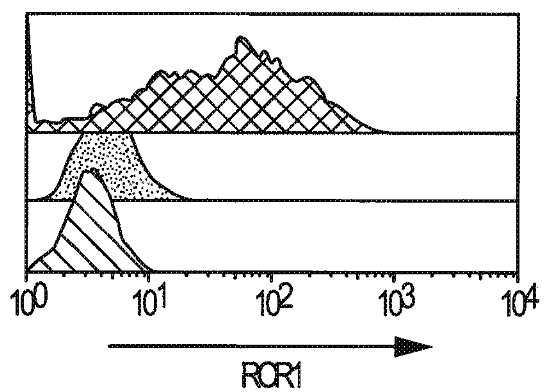
Figure 2B:
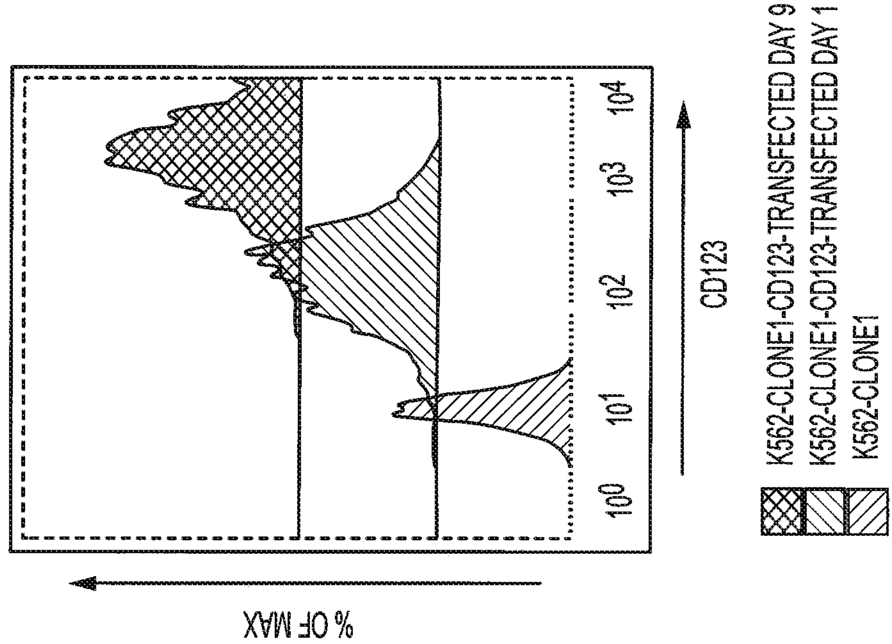
FIGS. 2A-2B. Generation of Clone 1-CD123. (A) Sleeping Beauty transposons expressing CD123 antigen. DNA plasmid vector maps for CD123 antigen IR/DR: Sleeping beauty Inverted Repeats/Direct Repeats, MNDU3/P: modified myeloproliferative sarcoma virus long terminal repeat enhancer-promoter (MNDU3) CD123: Human codon optimized CD123 antigen fused to hygromycin resistance gene through flag and F2A peptide. TK-codon optimized thimidine kinase gene BGH polyA; Bovine growth hormone polyadenylation sequence, ColE1: A minimal *E. coli* origin of replication, Kanamycin (Kan/R): Bacterial selection gene encoding Kanamycin resistance, Kanamycin promoter (Kan/p); Prokaryotic promoter (B) Histograms showing CD123 expression after electroporation of CD123 transposon and SB11 transposase into AaPC-Clone1 transfected with nucleofector solution without plasmids (blue) with plasmids on day1 (green) with plasmids day 9 (pink).
Figure 2A:
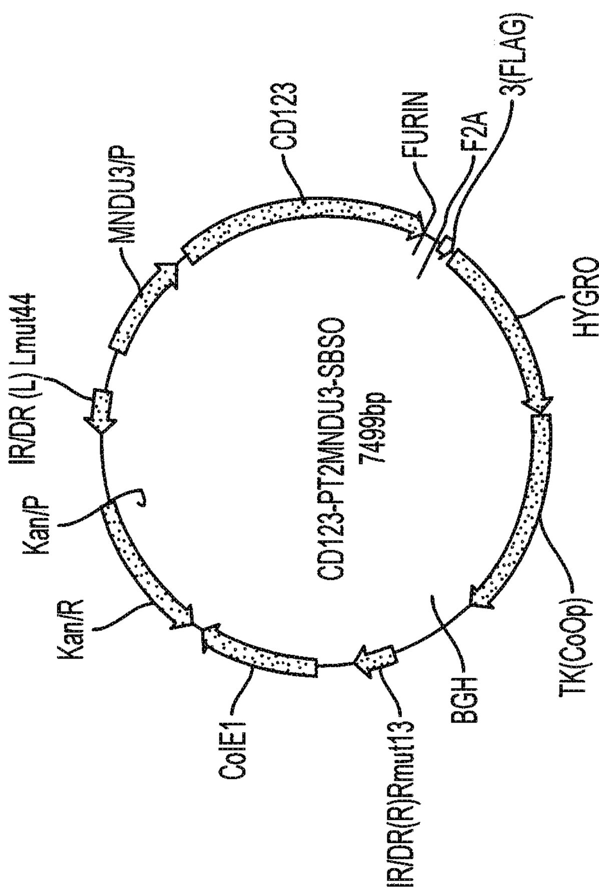

Generation of CD123$^+$ Activating and Propagating Cells (AaPC). Activating and Propagating cells (AaPC) has been successfully shown to expand antigen specific CAR T cells ex vivo (45-49). Binding of T cells to its cognate antigen on APC cell surface results in CAR$^+$ T cell clustering, phosphorylation ofimmune-receptor tyrosine-based activation motifs (ITAMs) there by activating T cells (89). K562 based AaPC-Clone 1 was previously made to expand CAR T cells co-express TAAs (CD19 and ROR1) co-stimulatory molecules (CD86 and CD137L), Fc receptors (endogenous CD32 and transfected CD64) for loading of agonistic anti-CD3 antibody OKT3 and IL-15 fusion protein (IL-15 fused to IL-15R$\alpha$) (FIG. 1). However AaPC-Clone 1 do not express CD123. Therefore a new AaPC has been derived to expand CD123-specific CAR T cells by enforced expression of CD123 on AaPC-Clone 1 (designated as Clone1-CD123). The CD123 DNA sequence was synthesized and codon optimized by Gene Art (Regensburg, Germany) fused to hygromycin resistance gene through F2A peptide and sub cloned into a SB transposon plasmid (FIG. 2A). AaPC-clone 1 cells were co-electroporated with CD123 transposon and transposase SB11 and CD123⁺ positive cells were selected by hygromycin selection. Within 9 days after electroporation, more than 98% of cells expressed CD123. (FIG. 2B).

Chimeric CARs Numerically Expand on AaPC and Stably Express CAR.

Six second generation CARs with chimeric scFvs were generated by mix and matching $V_L$ and $V_H$ chains of mAbs 26292, 32701, 32703 and 32716 specific to CD123 (CARs 5 to 10, see right side of FIG. 3A). These domains are shown below in Table 1. For simplicity these CARs are designated as "chimeric CARs" and CARs derived from regular scFvs of mAbs were used as positive control and called "Regular CARs" (CARs 1 to 4, see left side of FIG. 3A). These mAbs recognize different epitopes on CD123 with different binding affinities (96). All the scFvs except CAR-10 were fused in frame to CD3ζ and CD28 endo domains via CD8α hinge and CD8 transmembrane domain (TM) whereas IgG4 hinge and CD28 TM were used for CAR-10. CAR constructs were custom synthesized and cloned into Sleeping Beauty system.

TABLE 1

$V_L$ and $V_H$ domains of mAbs 26292, 32701, 32703 and 32716.

26292 VH domain

QVQLQQPGAELVRPGASVKLSCKASGYTFTSYWMNWVKQRPDQGLEWIGRIDPYDSETHYNQ
CDR1 CDR2
KFKDKAILTVDKSSSTAYMQLSSLTSEDSAVYYCARGNWDDYWGQGTTLTVSS
CDR3
(SEQ ID NO: 1; CDR1 = SEQ ID NO: 21, CDR2 = SEQ ID NO: 22, CDR3 = SEQ ID NO: 23)

26292 VL domain

DVQITQSPSYLAASPGETITINCRASKSISKDLAWYQEKPGKTNKLLIYSGSTLQSGIPSRF
CDR1 CDR2
SGSGSGTDFTLTISSLEPEDFAMYYCQQHNKYPYTFGGGTKLEIK
CDR3
(SEQ ID NO: 2; CDR1 = SEQ ID NO: 24, CDR2 = SEQ ID NO: 25, CDR3 = SEQ ID NO: 26)

32703 VH domain

QVQLQQPGAELVKPGAPVKLSCKASGYTFTNYWMNWIKQRPGRGLEWIGRIDPSDSESHYNQ
CDR1 CDR2
KFKDKATLTVDKSSNTAYIQLSSLTSEDSAVYYCARYDYDDTMDYWGQGTSVTVSS
CDR3
(SEQ ID NO: 3; CDR1 = SEQ ID NO: 27, CDR2 = SEQ ID NO: 28, CDR3 = SEQ ID NO: 29)

32703 VL domain

DIVMTQAAPSVPVTPGESVSISCRSNKSLLHSNGNTYLYWFLQRPGQSPQLLIYRMSNLASG
CDR1 CDR2
VPDRFSGSGSGTAFTLRISRVEAEDVGVYYCMQHLEYPYTFGGGTKLEIK
CDR3
(SEQ ID NO: 4; CDR1 = SEQ ID NO: 30, CDR2 = SEQ ID NO: 31, CDR3 = SEQ ID NO: 32)

32701 VH domain

QIQLVQSGPELKKPGETVKISCKTSGYVFTNYGMNWVKQAPGKGFKWMGWMNTNTGEPTSLE
CDR1 CDR2
DFKGRFAFSLETSASTAYLQINNLKNDDTATYFCARSGGYDPMDYWGQGTSVTVSS
CDR3
(SEQ ID NO: 5; CDR1 = SEQ ID NO: 33, CDR2 = SEQ ID NO: 34, CDR3 = SEQ ID NO: 35)

32701 VL domain

DIVLTQSPASLAVSPGQRATISCRASESVDNYGNTFMHWYQQKPGQPPKLLIYRASNLESGI
CDR1 CDR2
PARFSGSDSRTDFTLTINPVEADDVATYYCQQSKEDPPTFGGTKLELK
CDR3
(SEQ ID NO: 6; CDR1 = SEQ ID NO: 36, CDR2 = SEQ ID NO: 37, CDR3 = SEQ ID NO: 38)

32716 VH domain

QIQLVQSGPELKKPGETVKISCKASGYIFTNYGMNWVKQAPGKSFKWMGWINTYTGESTYSA
CDR1 CDR2
DFKGRFAFSLETSASTAYLHINDLKNEDTATYFCARSGGYDPMDYWGQGTSVTVSS
CDR3
(SEQ ID NO: 7; CDR1 = SEQ ID NO: 39, CDR2 = SEQ ID NO: 40, CDR3 = SEQ ID NO: 41)

TABLE 1-continued

| $V_L$ and $V_H$ domains of mAbs 26292, 32701, 32703 and 32716. |
|---|
| 32716 VL domain |
| DIVLTQSPASLAVSLGQRATISCRASESVDNYGNTFMHWYQQKPGQPPKLLIYRASNLESGI<br>CDR1 CDR2<br>PARFSGSGSRTDFTLTINPVEADDVATYYCQQSNEDPPTFGAGTKELK<br>CDR3<br>(SEQ ID NO: 8 ; CDR1 = SEQ ID NO: 42, CDR2 = SEQ ID NO: 43, CDR3 = SEQ ID NO: 44) |

Figure 4A:
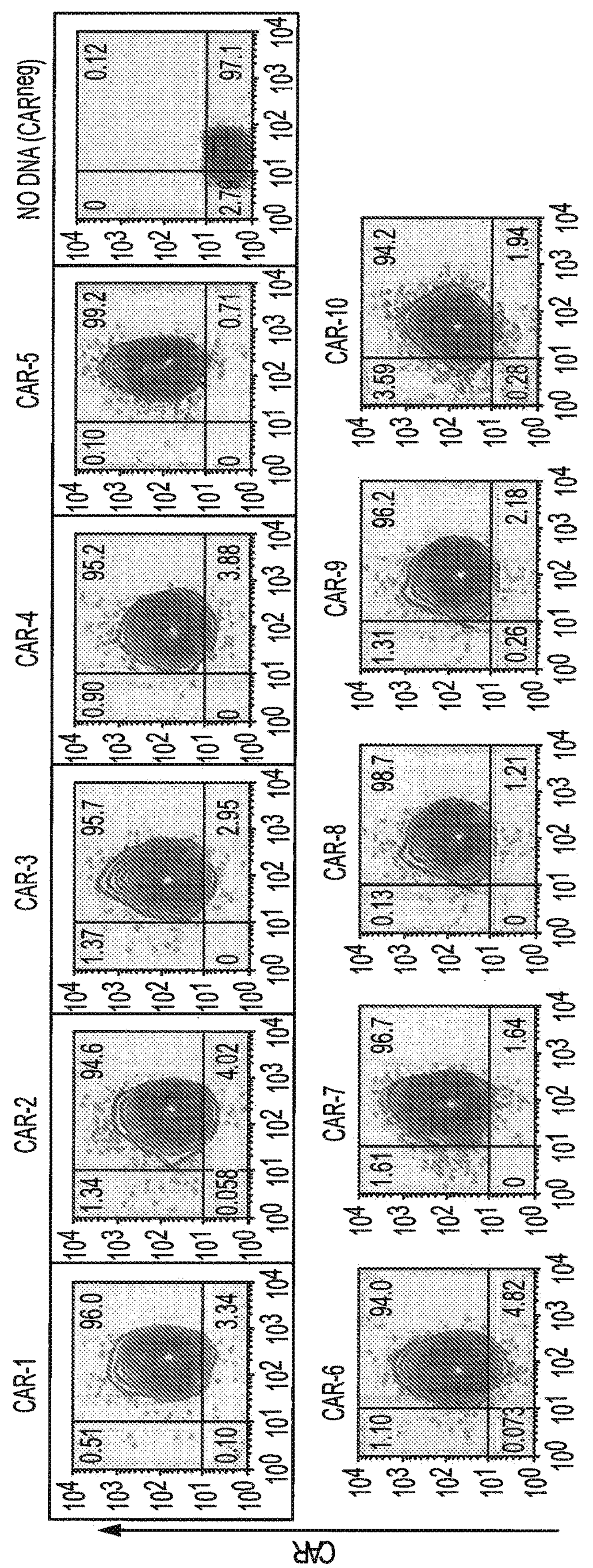
FIGS. 4A-4C. Expression and expansion kinetics of chimeric CARs. CAR expression and expansion kinetics following electroporation and expansion on Clone 1-CD123 in presence of IL-2 and IL-2. (A) CAR expression on Day 21 after electroporation detected by CD123 recombinant protein fused to Fc followed by serial staining with Fc and CD3 antibodies. PBMC electroporated with nucleofector solution without CAR plasmids ($CAR^{neg}$) used as negative control. (B) Expansion kinetics of CARs 1 to 4. (C) CARs 5-10 over a period of 28 days and data pooled from 3 donors mean±SD.
Figure 4C:
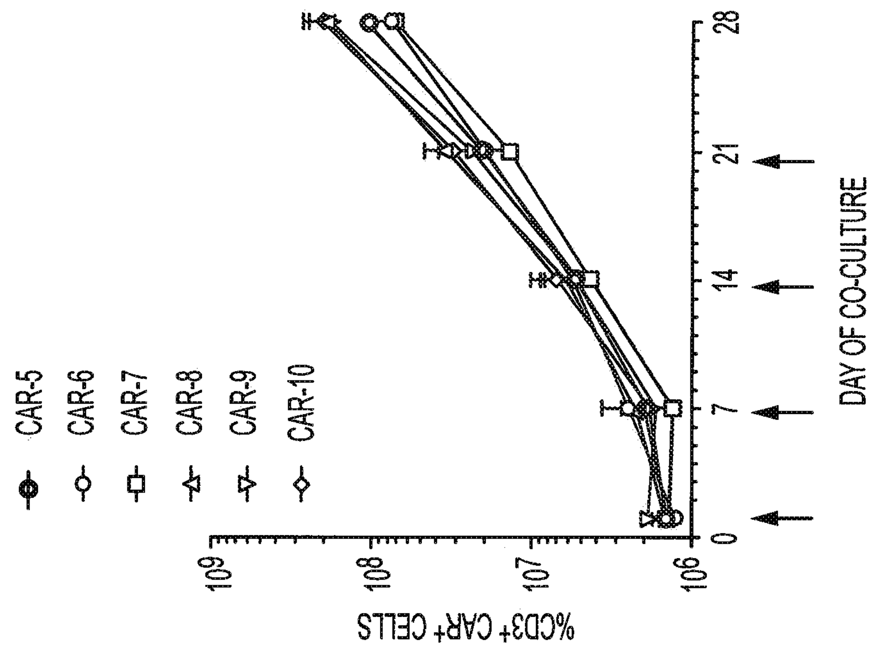
Figure 4B:
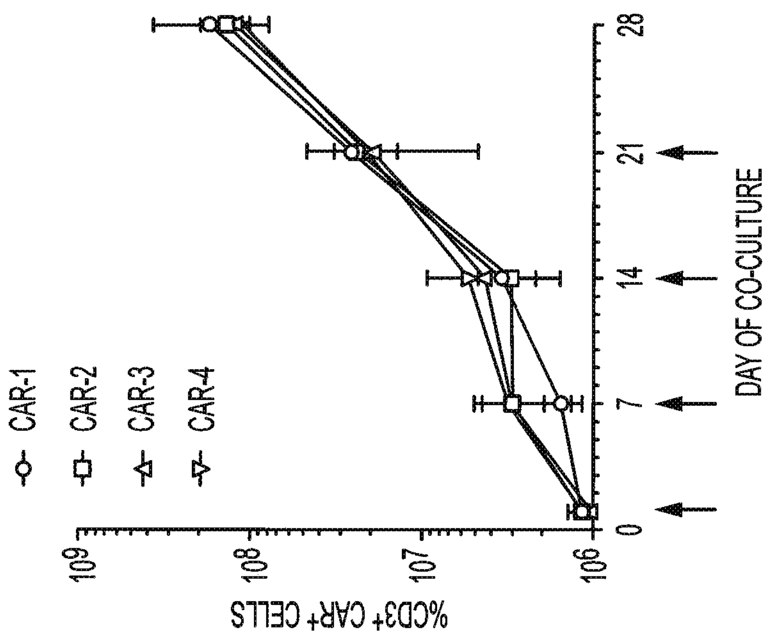

CAR plasmids (typical representation of CAR plasmid is given in FIG. 3B, left) along with transposase SB11 (FIG. 3B, right) were electroporated into CD56$^+$ NK cell depleted PBMC and expanded on Clone1-CD123 at 2:1 AaPC:T cell ratio in presence of recombinant cytokines IL2 and IL-21. T cell cultures were stimulated with AaPC and surface phenotyped every 7 days starting from day 1. CAR expression was detected with CD123 recombinant protein fused to Fc followed by serial staining with antibodies specific to Fc and CD3. The results are shown in FIG. 4A. Cultures were devoid of NK cells though a small proportion of T cells express CD56, they do not express CD3 (data not shown). Chimeric CARs expanded at similar rates as regular CARs (FIGS. 4B and 4C).

Chimeric CARs Maintain Specificity to CD123.

Figure 5:
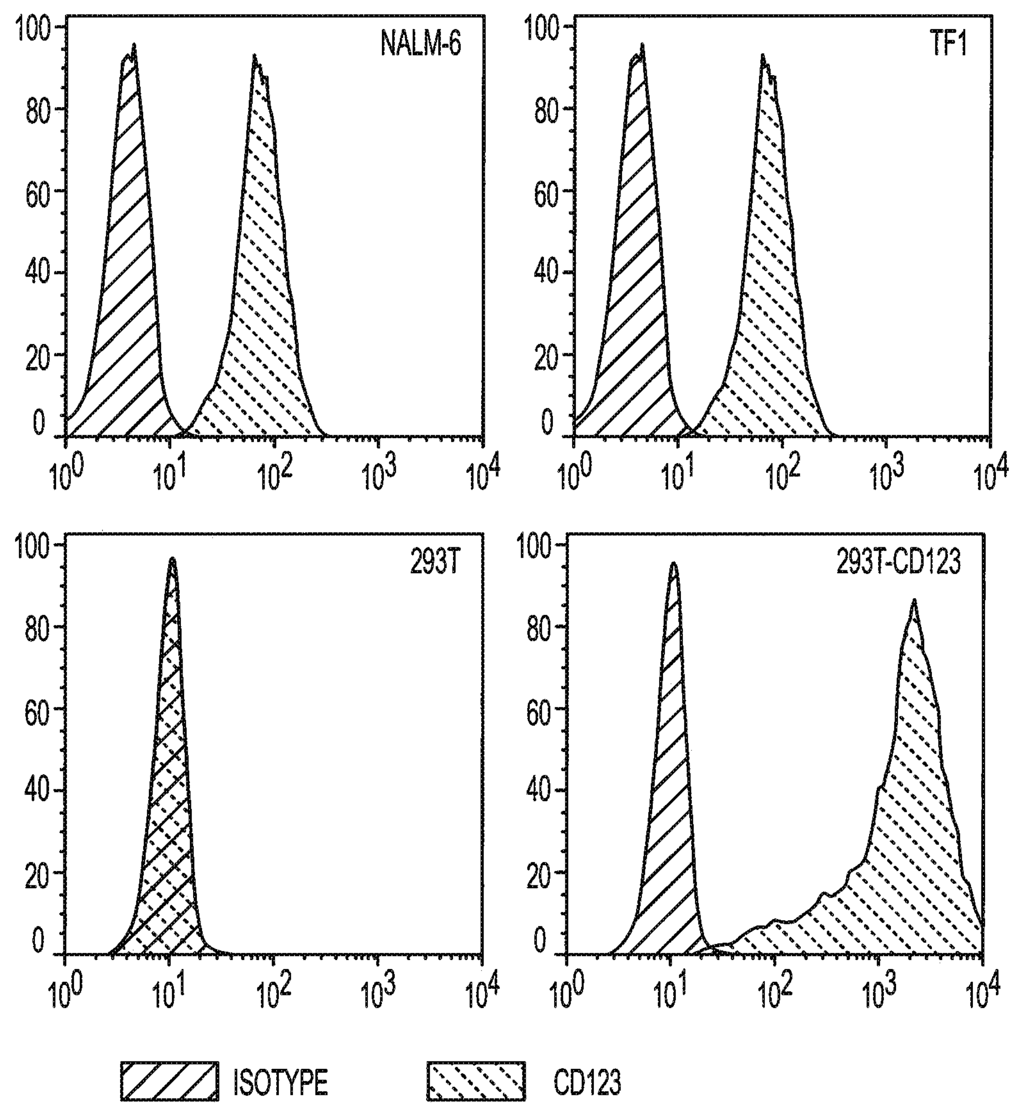
FIG. 5. CD123 expression on leukemic cell lines and 293T cells CARs. CD123 expression assessed by flow cytometry in $CD123^+$ Leukemic cell lines NALM6, TF1, $CD123^{neg}$ human embryonic kidney cell line, and 293T transfected with CD123.
Figure 6A:
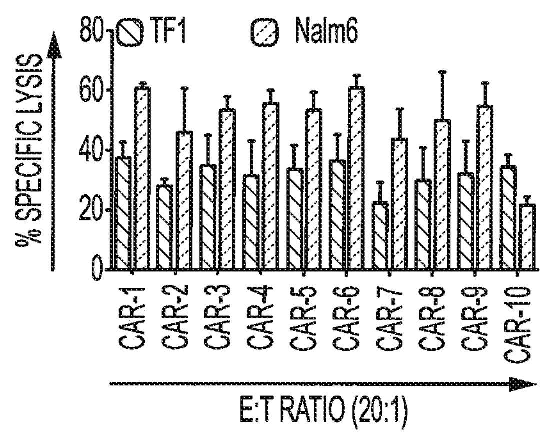
FIGS. 6A-6C. Specific cytolysis of chimeric CAR T cells. (A) Left. in vitro efficacy of CAR T cells in established $CD123^+$ pre B-ALL cell line Nalm6 and $CD123^+$ AML cell line TF1. (B) Right. Antigen specific cytolysis in $CD123^{neg}$ human embryonic kidney cell line 293T and 293T cells stably transfected with CD123 antigen. (C) Cytolysis by $CAR^{neg}$ T cells in NALM6, TF1, 293T and 293T-CD123. All data are mean±SD of triplicate measurements in CRA.
Figure 6B:
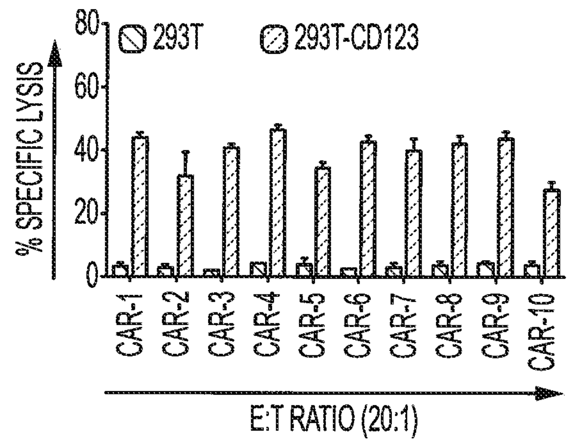
Figure 6C:
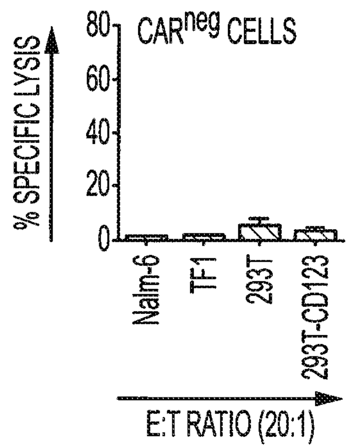

Before testing in vitro efficacy of chimeric CARs, several leukemic cell lines including pre-B-ALL cell line Nalm6 and AML cell line TF1 and human embryonic kidney cell line 293T (FIG. 5). To test if chimeric CAR T cells demonstrate specific lysis of CD123+ tumor cells in vitro, chromium-51 labeled target cell lines were co-cultured with CAR T cells in a standard 4 hour chromium release assay (effector:target (E:T) ratio 20:1). CD123+ pre B-ALL cell line Nalm6, and AML cell line TF1 were used as positive controls and 293T human embryonic kidney cell line used as negative control. CAR T cells able to lyse CD123+B-ALL tumor cell lines (FIG. 6A) but not CD123neg cell line 293T (FIG. 6B). To further verify killing by CAR T cells, CAR$^{neg}$ was co-cultured with target cell lines at a ratio of 20:1; they failed to kill CD123$^+$ B-ALL cell lines. To test antigen-specific lysis, 293T cells and CAR T cells were co-cultured with 293T cells CAR T cells and 293T cells transfected with CD123. CAR T cells lysed transfected cells, but not CD123$^{neg}$ 293T (FIG. 6A). This data suggests that chimeric CARs recognize the CD123 antigen and execute antigen specific killing.

IFN-γ Production by Chimeric CARs in Response to CD123 Antigen.

Figure 7:
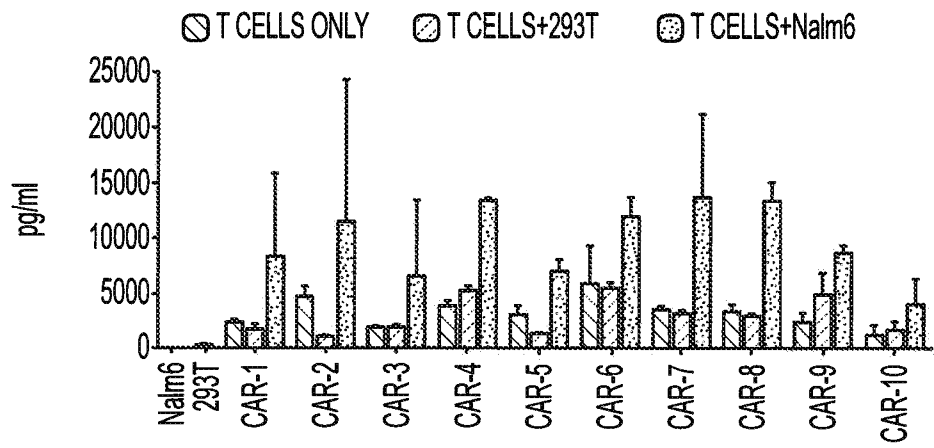
FIG. 7. IFN-γ production by chimeric CARs in response to CD123 antigen. T cells on Day 21 after electroporation were incubated with Nalm-6 and 293T cells in E:T ratio 2:1 for 48 hours. IFN-γ production was assessed by cytokine capture beads by LEGEND PLEX™ Human Th1 panel kit (Biolegend). Samples were run in IQUE® Screener Systems (intellicyt) and analyzed by LEGEND PLEX™ software provided with the kit.

In order to assess antigen-specific effector function of chimeric CARs, IFN-γ production was assessed in CD123$^+$ Nalm6 cells. 293T cells used as negative control. T cells on Day 21 after electroporation were incubated with Nalm6 and 293T cells in E:T ratio 2:1 for 48 hours. T cells without targets used to see the difference with and without targets. Nalm6 stimulated chimeric CAR T cells produced IFN-γ in significant amounts compared to CAR T cells treated with 293T and T cells alone (FIG. 7). These data established the effector function and functionality of chimeric CARs in response to antigen.

In Vitro Toxicity of Chimeric CAR T cells in Normal Hematopoietic Cells.

Many studies have explored the expression of CD123 indicate that part of hematopoietic progenitors from human cord blood, bone marrow, peripheral blood and fetal liver express CD123 while primitive population of HSCs express at low levels or absent (157). Though the antibody based CD123– targeting therapies in AML were reported to be well tolerated sparing normal hematopoietic cells, recent pre-clinical studies employing CD123-specific CAR T cells resulted in eradication of normal human myelopoiesis (161).

Figure 8A:
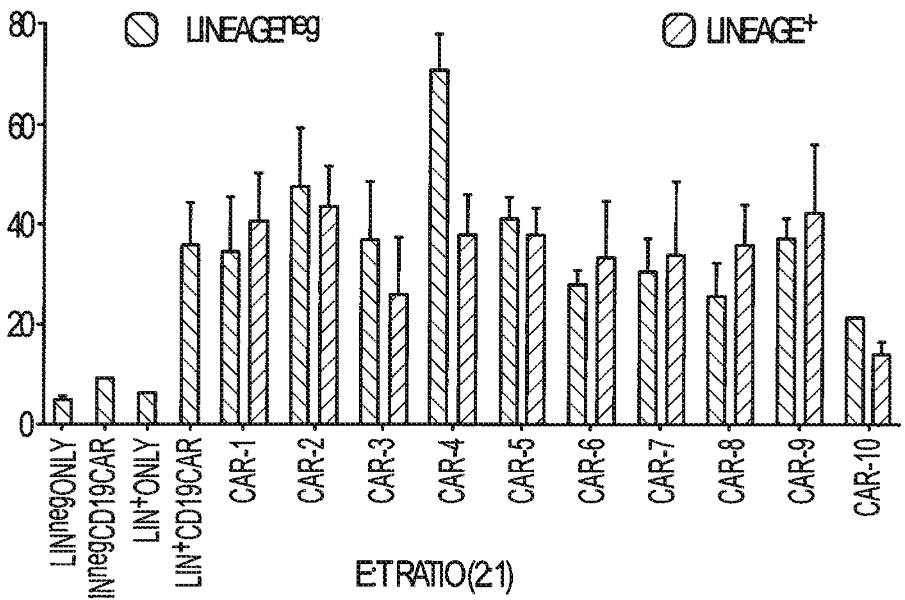
FIGS. 8A-8C. Anti-tumor efficacy of chimeric CARs and IgG4 CAR. (A) In vitro lysis of normal hematopoietic cells by chimeric CARs. (B) Flow analysis of CD123 expression on B-ALL cell lines RCH-ACV, KASUMI-2, Nalm6 and B-cell lymphoma OCI-Ly19. (C) In vitro efficacy of CD123-IgG4-CD28 (CAR-10) specific $CAR^+$ T cells in B-ALL cell lines in a standard 4 hour chromium release assay. $CD123^{neg}$ mouse T cell lymphoma cell line EL4 was transfected with CD123 antigen to determine antigen specific killing. Data was reported as mean±SD.
Figure 8B:
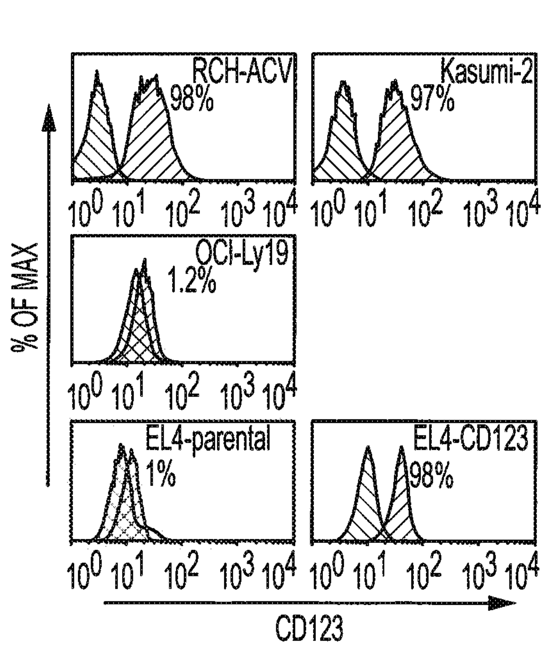
Figure 8C:
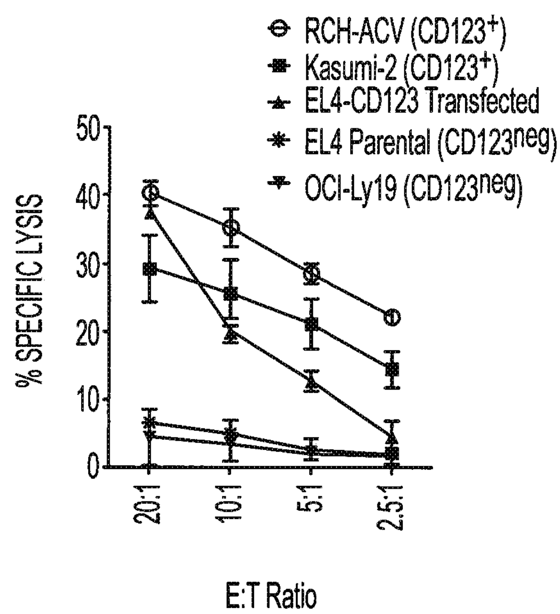

To test the in vitro toxicity of chimeric CARs for normal hematopoietic cells, lineage$^+$ and HSCs enriched lineage$^{neg}$ fractions were isolated from normal BM cells and labeled with PKH-26. CAR T cells co-cultured with PKH-26 labeled cells for 48 hours with E:T ratio 2:1. CD19 CAR T cells used as control. Cells were stained with 7AAD and live/dead cells were enumerated by 7AAD exclusion. CAR T cells are apparently lysed both lineage+ and lineage$^{neg}$ hematopoietic cells (FIG. 8A). CD19 is expressed on differentiated cells but not expressed on HSCs. This is apparent by minimal lysis in lineage$^{neg}$ population than lineage$^+$ population. These data raise concern that CD123-specific CAR therapy may be detrimental to normal hematopoiesis. However IgG4 hinge based CAR-10 showed less cytotoxicity to normal hematopoietic cells when compared to its counterparts with CD8α hinge (CARs 5-9). CAR-10 (referred to as CD123-IgG4 CAR hereafter) was chosen to take forward to generate preclinical data in support of clinical trials in B-ALL (current example) and AML (Example 2). Before testing the in vivo efficacy of CD123-IgG4 CAR T cells in NSG mice in B-ALL, in vitro efficacy was reconfirmed in additional cell lines. CD123 expression was assessed in CD123$^+$ B-ALL tumor cell lines RCH-ACV, kasumi-2 and CD123$^{neg}$ cell lines OCI-Ly19 and EL4 (FIG. 8B). CAR T cells were co-cultured with 51 chromium labeled target cells in different ratios in 4-hour chromium release assay. CAR T cells able to lyse CD123$^+$ B-ALL tumor cell lines, but not OCI-Ly19. Antigen specific killing was determined by using EL4 and EL4 transfected with CD123 where CAR T cells able to lyse EL4-CD123 but not EL4-parental (FIG. 8C).

In Vivo Clearance of B-ALL Tumors by CD123-Specific T Cells.

Figure 9B:
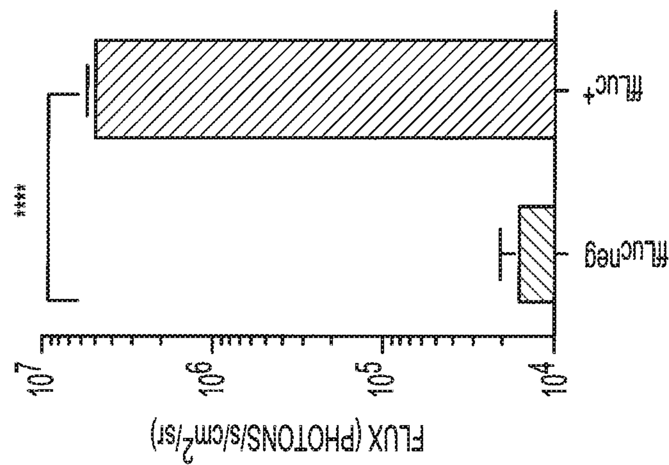
FIGS. 9A-9B. Expressing fire fly luciferase on RCH-ACV. (A) Lentiviral vector pLVU3G effluc T2A mKateS158A transduced to genetically modify RCH-ACV to express mKate red fluorescence protein and firefly luciferase (ffLuc; bioluminescence reporter) for non-invasive bioluminescence imaging (BLI) of tumor burden in vivo (B) Flux activity in B-ALL cell line RCH-ACV transduced with lenti-viral vector expressing firefly luciferase compared to $effluc^{neg}$ control (****$p<0.0001$ unpaired t-test).
Figure 9A:
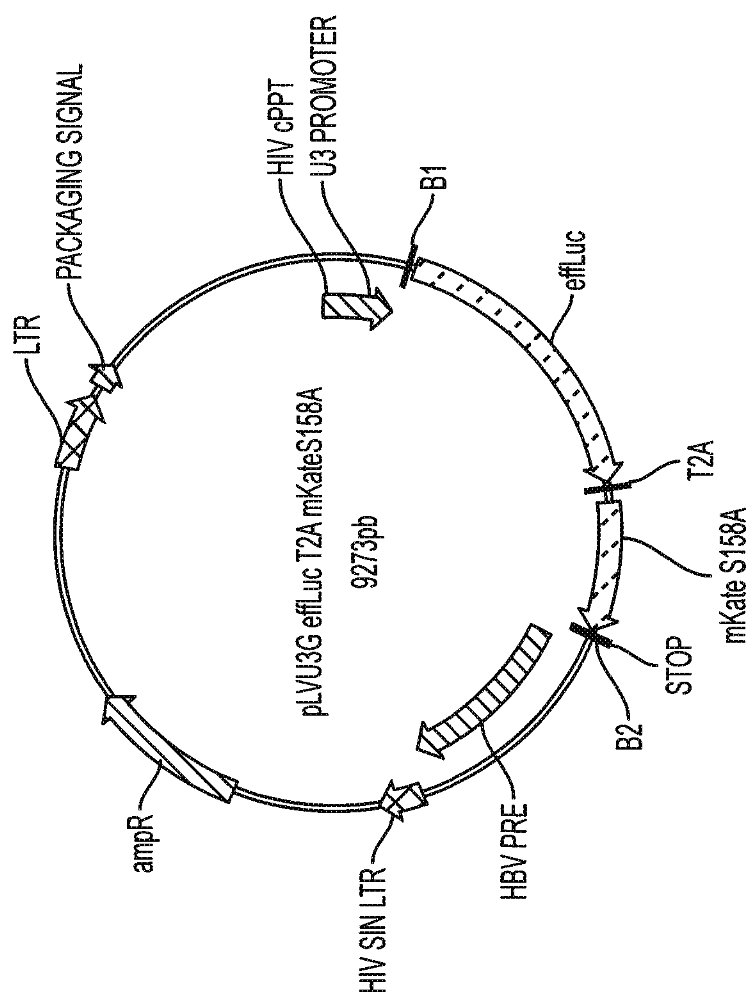
Figure 10A:
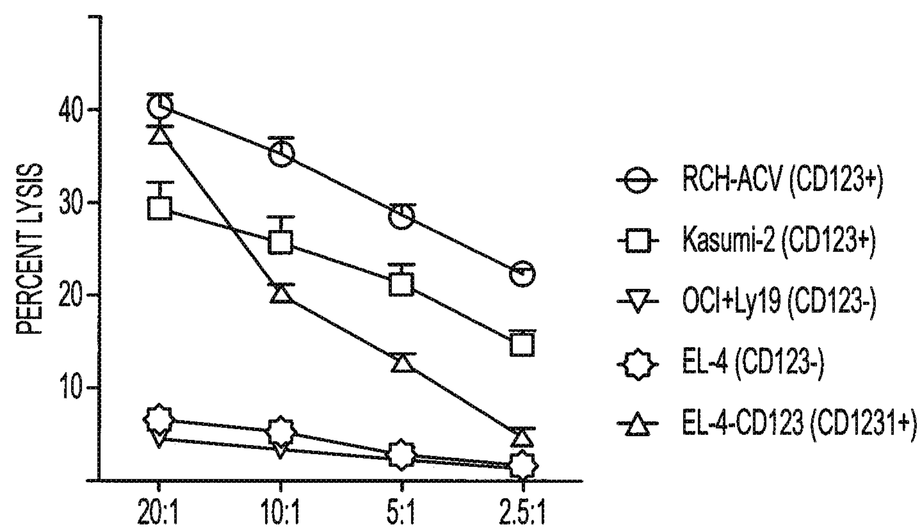
FIG. 10A-10E. Efficacy of CD123-specific $CAR^+$ T cells for the treatment of B-ALL in a murine model. (A) In vitro lysis of B-ALL cell lines by CD123-specific $CAR^+$ T cells measured with a 4 hour chromium release assay (B) Schematic of the RCH-ACV B-ALL xenograft model. The experimental design is similar to that shown in 5A, but T cells and cytokines were given on days 7, 14 and 21, with imaging weekly. (C) BLI imaging of the CAR-treated and untreated groups on day 28. BLI images of mice display an overlay of luciferase activity, using the scale shown on the right, displayed over the white-light image of the mice. (D) Luciferase activity measured by BLI in the CAR-treated group compared with the untreated group. (E) Kaplan-Meier curves display the survival analysis of xenograft mice treated with CD123-specific CAR T cells compared with untreated mice. **$p<0.01$.
Figure 10B:
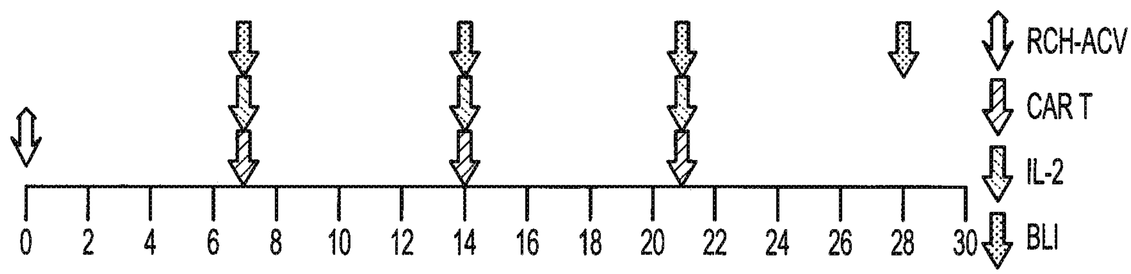
Figure 10C:
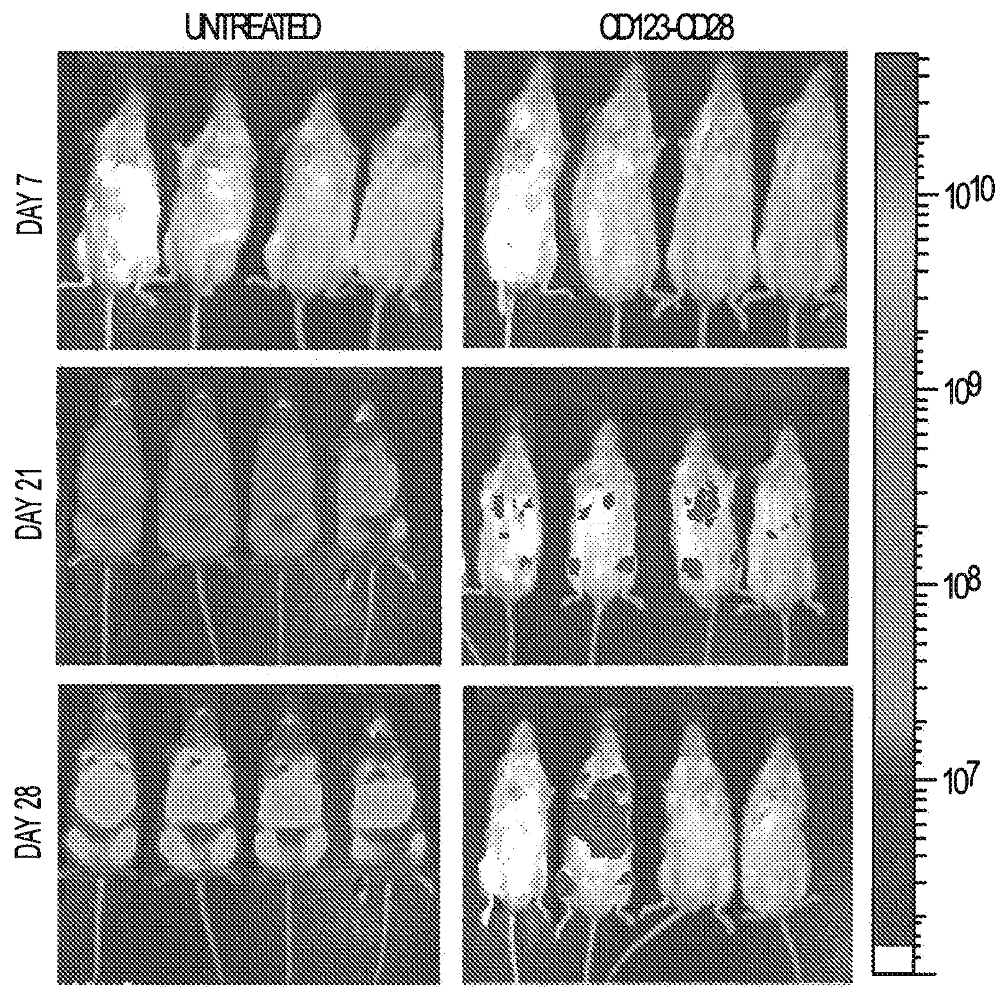
Figure 10D:
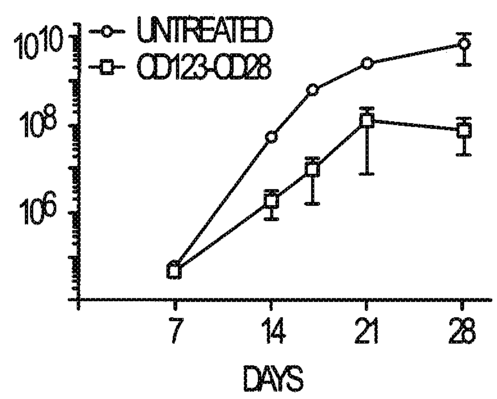
Figure 10E:
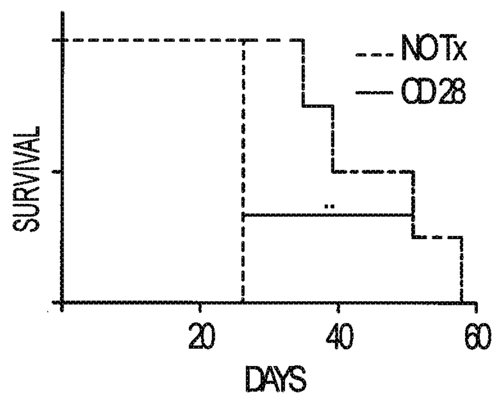

In order to test in vivo efficacy of CAR T cells, B-ALL cell line RCH-ACV were transduced with lentiviral vector pLVU3G effluc T2A mKateS158A (FIG. 9A) and mKate$^+$ cells were Fluorescence-activated cell (FACS) sorted and the clones from single cells were developed for uniform mKate expression for bioluminescent imaging (BLI). RCH-ACV cells expressed luciferase confirmed by standard luciferase assay (**$p<0.0001$) (FIG. 9B). On Day 0 and day 1 mice were intravenously treated with tumor cells and CAR T cells respectively. 3 more infusions of CAR T cells were given on day 7, 14 and 21 followed by intraperitoneal treatment of IL2 (60000 units/mice). Untreated group did not receive CAR T cells (FIG. 10A). CAR treated group showed reduced tumor burden quantified by BLI (FIG. 10B) and flux activity ($p<0.0001$) (FIG. 10C) and significant improvement in survival ($p<0.01$ (FIG. 10D) compared to control mice. These data suggests that CD123 provides additional approach to treat B-ALL through chimeric antigen receptors in addition to targeting CD19.

Example 2—Targeting AML by iCaspase9 Co-Expressing CD123-Specific CAR T Cells

Acute myeloid leukemia (AML) is a clonal proliferation of malignant myeloid blast cells in the BM with impaired normal hematopoiesis. Despite many advances AML remains a lethal disease. Standard treatment regimens chemotherapy and radiation ensure long-term remission only in 30 to 50% of patients with a low survival probability resulting in resistance and relapse (109-111). The relapse in AML is due to minimal residual disease caused by small population of Leukemic stem cells (LSC) resistant to drugs and radiation. Antigen specific based adoptive immunotherapy will play a complimentary role in eradicating minimal residual disease by targeting leukemia associated antigens expressed on LSCs and leukemic cells (112-114).

CARs have demonstrated clinical efficacy in treating leukemia in preclinical models and are being tested in several clinical trials and emerging as powerful tools for adoptive immunotherapy (115). CARs are derived by fusing scFv of mAbs specific TAAs to T cell signaling domains CD28 or CD137 and CD3ζ. CARs re-direct the specificity of T cells to recognize tumor antigens independent of MHC (116-119). CD123, the IL-3 receptor α-subunit has been reported to be overexpressed on up to 95% of leukemic blasts and leukemic stem cells (LSC) in AML with weak on normal HSCs and absent on cells outside hematopoietic lineage (120-124). PhaseI clinical trials targeting CD123 in AML using neutralizing mAbs and cytotoxic protein fused to IL-3 cytokine showed limited therapeutic efficacy pressing the need for more novel efficacious treatments (125, 126). CD123 is a viable target in AML through chimeric antigen receptors given its wide expression on leukemic blasts, progenitors, LSCs and weak or no detectable expression on hematopoietic stem cells. The main goal of this study is, to redirect T-cell specificity to CD123 to target AML and to generate preclinical data in support of an adoptive immunotherapy trial. It was hypothesized that T cells can be re-directed with a CAR to target CD123 expressed on leukemic blasts and leukemic stem cells. Comparative functional evaluation of two CD123-specific CARs is described with CD28 or CD137 co-stimulatory domains (these co-stimulatory domains are provided as SEQ ID NOs: 46 and 47, respectively). The approach is based on methodology used in the first-in-human clinical trials using CD19-specific CAR T cells generated by Sleeping Beauty system and expanding them on Activating and Propagating cells (127-129). CD123-specific CARs with CD28 or CD137 co-stimulatory domains efficiently lysed $CD123^+$ AML tumor cell lines, primary AML patient samples and showed activated multiple effector functions. The study further shows that both CD123-CD28 and CD123-CD137 $CAR^+$ T cells are equally effective in clearing tumor in NSG mice engrafted with $CD123^+$ tumors.

Construction of iCaspase 9 Co-Expressing CD123-Specific CAR SB Plasmids.

Several pre-clinical and animal models have demonstrated that $CAR^+$ T cells with CD28 or CD137 co-stimulatory domains have been shown to have improved persistence compared to CARs with CD3 zeta signaling domain alone. However, the improved anti-tumor efficacy of one over the other is not investigated at depth. Two codon-optimized Sleeping Beauty transposons encoding CD123-specific second generation CARs fused to suicide gene iCaspase 9 with CD28 (designated as CD123-CD28 CAR) (FIG. 11A) or CD137 (designated as CD123-CD137 CAR) (FIG. 11B) co-stimulatory domains The CAR plasmids were constructed in the following order: human elongation factor-α (hEF-α) promoter was used to drive expression of CARs. Following the promoter, iCaspase 9 suicide gene is fused to CD123-specific CAR construct of 5' to 3' CAR open reading frame (ORF) consisting of signal peptide, scFv, whitlow linker, modified IgG4 hinge, CD28 transmembrane domain, CD28 or CD137 endo-domain and CD3ζ signaling domain. iCaspase 9 and CAR construct were fused through F2A cleavage peptide. iCaspase 9 was fused upstream of F2A to make sure iCaspase 9 translated first. The scFv is derived from $V_L$ of mAb 26292 and $V_H$ of mAb 32703 specific to CD123 (FIG. 3A, CAR-10 described in Example 1). To distinguish CARs with CD28 and CD137 endo-domains a unique oligonucleotide SIM for CD28 CAR and FRA for CD137 CAR were interspersed between stop codon of CAR and BGH Poly A tail. Upon electroporation the indirect repeats (IR) of SB system flanking 5' end of hEF-α promoter and 3' end of Poly A tail is cut by SB11 transposase and integrates within the TA repeats in human T cell genome. Kanamycin resistance gene will allow to amplify the SB plasmids in large numbers in bacteria.

SB Modified T Cells Stably Co-Express CD123-Specific CAR and iCaspase 9.

Figure 12:
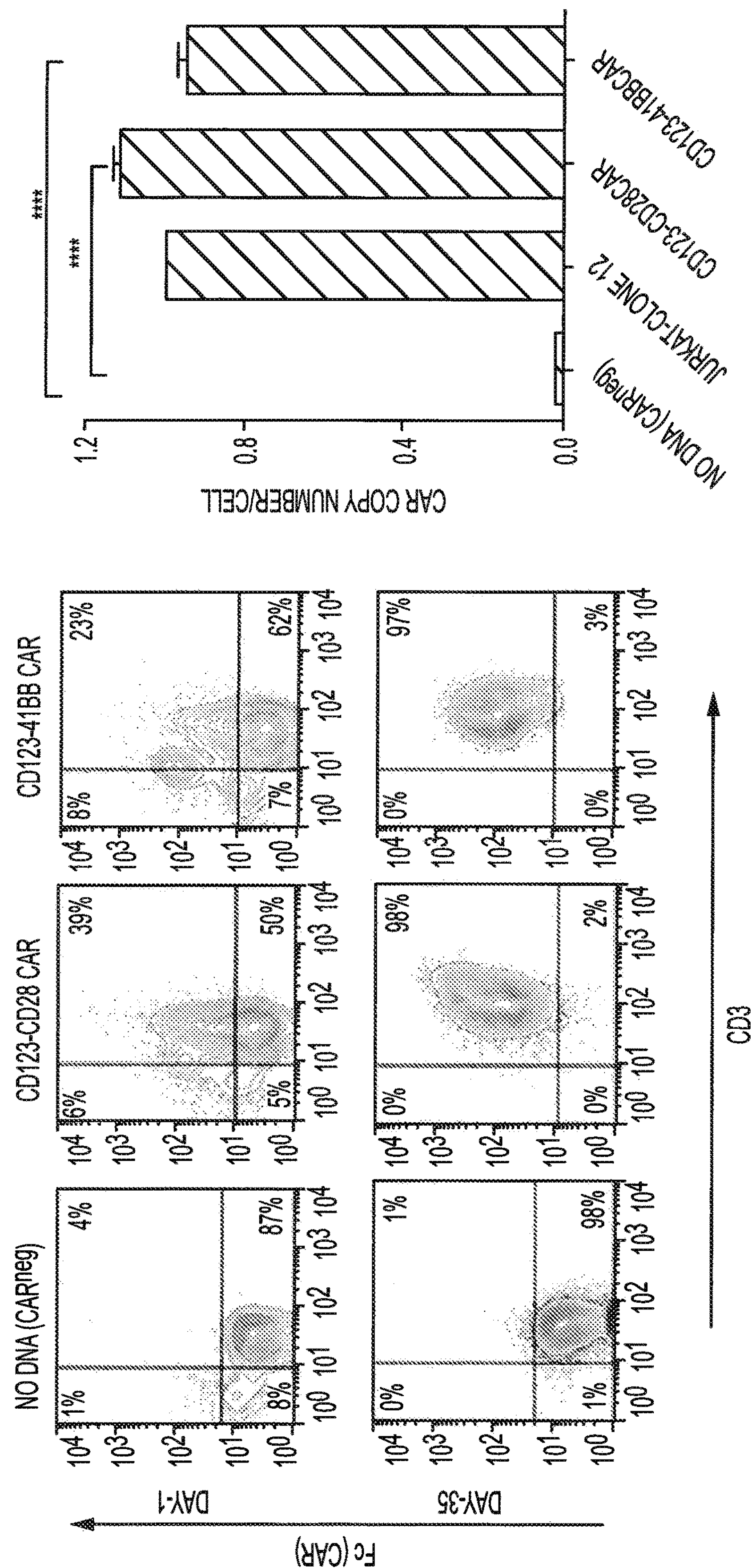
FIG. 12. CAR Expression and copy number in iCaspase $9^+$ CD123− specific CARs. CAR Expression in CD123-CD28 (middle) and CD123-41BB (right) T cells on day 1 and 35 after electroporation and co-culture on AaPC Clone 1-CD123 where $CAR^{neg}$ T cells (left) were used as negative controls. T cells were detected with CD3 antibody and CAR expression with Fc-specific antibody against IgG4. CAR copy number was determined on day 28 using primers and probes specific for CD28 transmembrane and IgG4 hinge region. $CAR^{neg}$ and Jurkat cells were used as negative and positive controls respectively.
Figure 13:
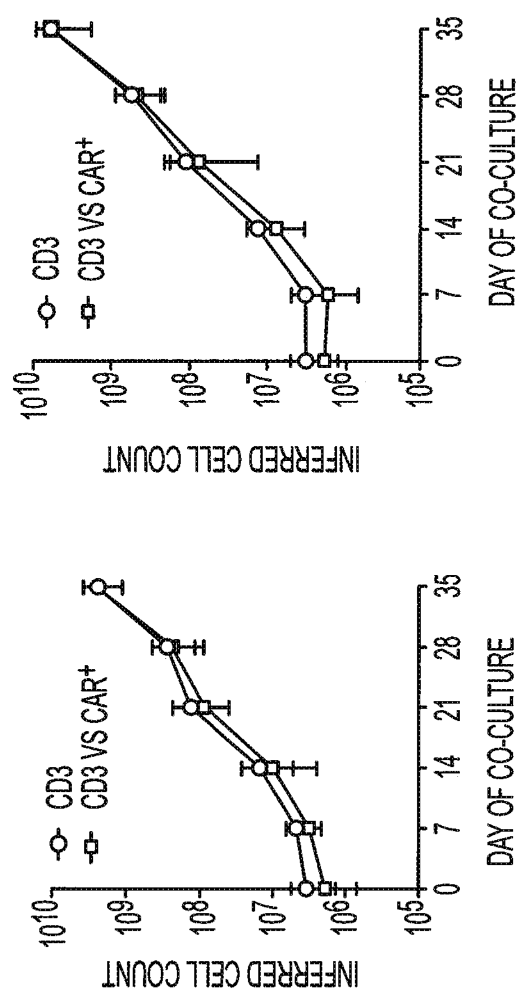
FIG. 13. Expansion kinetics of $iCaspase^+$ CD123-specific CARs. CD3+ and $CD3^+CAR^+$ T cells over a period of 35 days as noted by total number of cells counted at the end of culture (p=0.14) Two-way ANOVA.

PBMC from normal donors were co-electroporated with CD123-CD28 or CD123-CD137 transposon and SB11 transposase co-cultured with $CD123^+$ AaPC (designated as clone1-CD123) for 4 to 5 weeks. PBMC electroporated with nucleofector solution without CAR plasmids used as negative control ("NO DNA" $CAR^{neg}$ T cells) were expanded on OKT3 loaded Clone1-CD123. By day 35 more than 95% of T cells expressed CAR (FIG. 12A) and CD3 (Both CARs expanded at similar rates as noted by total number of cells counted at the end of culture (p=0.14) Two-way ANOVA) (FIG. 13). Genomic DNA from Day 35 CAR T cells amplified by using primers and probes specific to IgG4-Fc and CD28 transmembrane domains showed on an average integration of 1 copy of CAR expression cassette per cell. Jurkat clone1 of known copy number per cell used as positive control and NO DNA cells used as negative control (FIG. 12B). Thus SB transposition of CAR into PBMC and selective propagation on AaPC, Clone 1-CD123 resulted in generation of CAR T cells to clinically relevant numbers with high CAR expression.

Immuno-Phenotype of iCaspase $9^+$ CD123 $CAR^+$ T Cells.

Figure 14A:
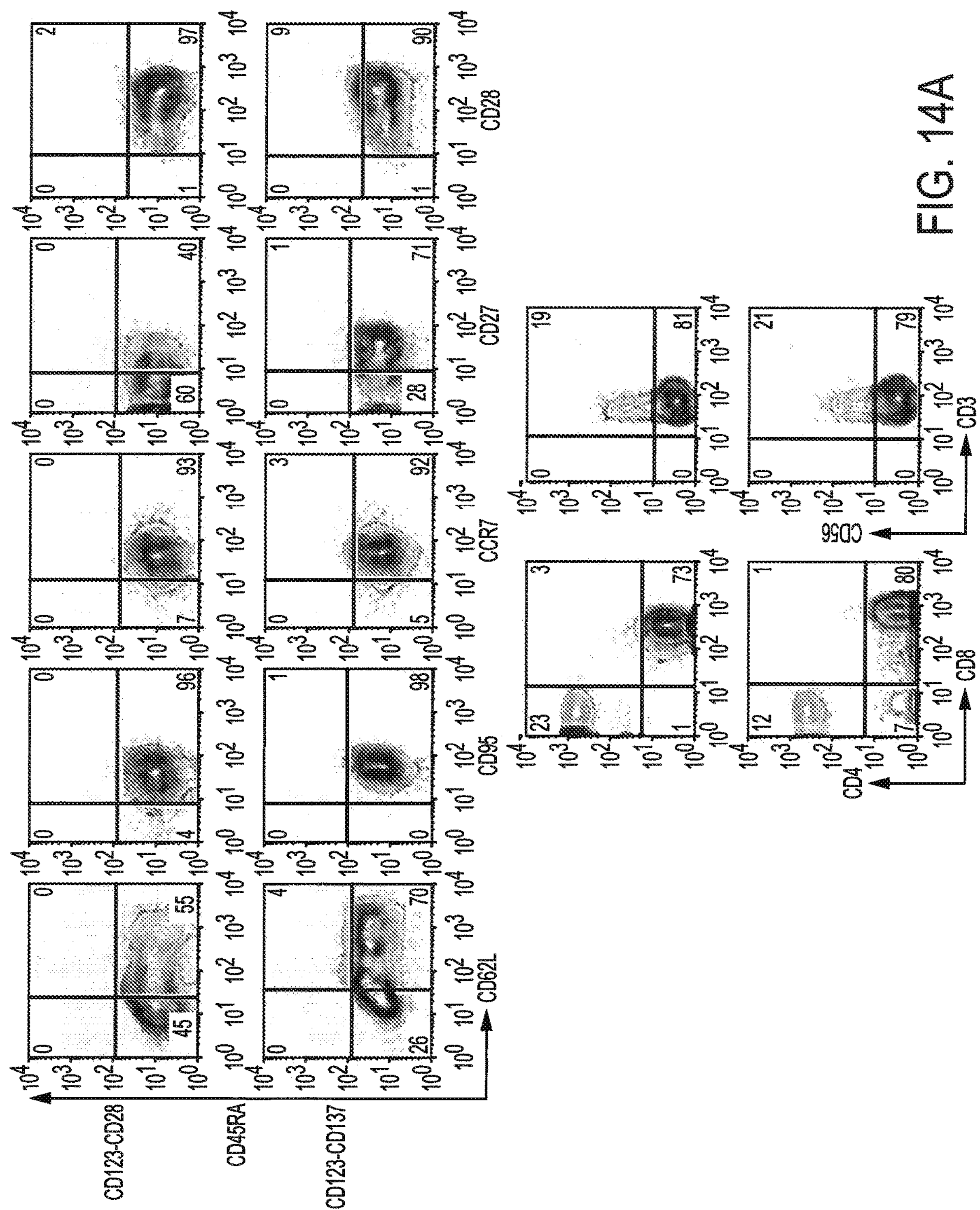
FIGS. 14A-14C. Immunophenotype of iCaspase $9^+$ CD123-specific CAR T cells. (A) Flow analysis of memory markers on $CD3+Fc^+$ gated T cells. Representation of one donor of total 3 donors actually used in the experiment (left) and selective surface markers CD4, CD8, and CD56 (right). (B) memory and exhaustion markers CD57 and PD1 expressed (n=3) on CD123-CD28 and CD123-CD137 CAR+ T cells. Paired Student's two-tailed t-test was used *$p<0.05$. (C) T cell differentiation subsets gated on CD3+ $Fc^+$ population, histograms depicting cell percentage in each subset, $T_{Naive}$ $CD45RA^+CD62L^+CD95^{neg}$ $CCR7^+$, $T_{EMRA}$ ($CD45RA^+CD62L^{neg}CD95^{neg}CCR7^{neg}$), $T_{EM}$ ($CD45RA^{neg}CD62L^{neg}CD95^+$ $CCR7^{neg}$) and $T_{CM}$ ($CD45RA^{neg}CD62L^+CD95^+$ $CCR7^+$) in CD123-CD28
Figure 14C:
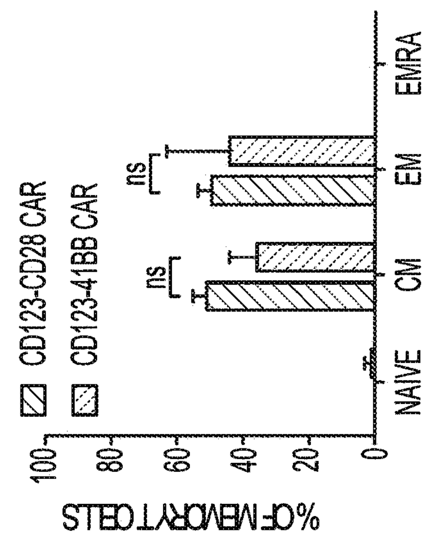

The immunophenotypic analysis of CAR T cells by flow cytometry shows >95% T cells co-expressing CD3 and CAR with a mixture of $CD8^+$ and $CD4^+$ T cells. (FIG. 14A, right). Establishment of long term memory and survival is the key for improving anti-tumor efficacy of CAR T cells in clinical setting. Terminally differentiated effector memory ($T_{EM}$) T cells lose their capacity to expand and persist after adoptive transfer. On the contrary, less differentiated and minimally manipulated T cells with central memory phenotype ($T_{CM}$) can further expand, differentiate and self-renew with superior clinical response. To date, adoptively transferred $CAR^+$ T cells have demonstrated minimal in vivo expansion and antitumor efficacy in clinical trials (130-132). Though IL-2 is routinely used for T cell expansion, recent reports suggests that other common gamma chain cytokines such as IL-15 and IL-21 more usefully suppress differentiation of naive T cells into effector T cells (133).

SB transposition and expansion on $mIL15^+$ AaPC in presence of IL-2 and IL-21 resulted in outgrowth of T cells with less differentiated phenotype and memory associated markers CD45RA, CD45RO, CD62L, CCR7, CD27, CD28, and no detectable expression of exhaustion markers CD57 and PD1. Few cells express BM homing receptor CXCR4. (FIG. 14B).

Figure 14B:
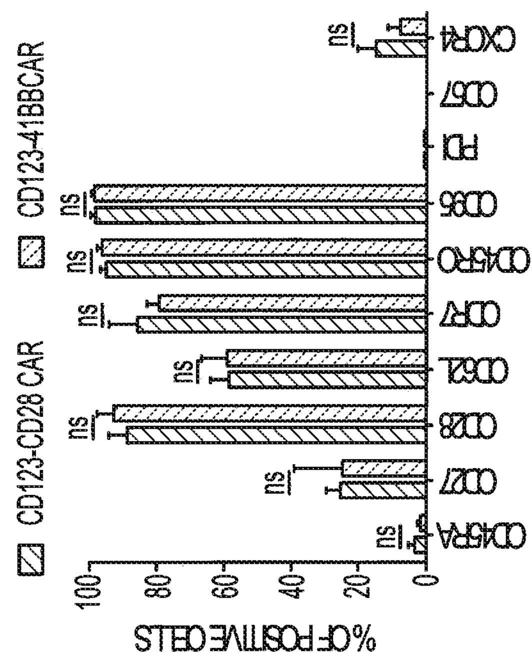

$CAR^+$ T cells belonged to less differentiated phenotype primarily composed of few naive (TN) defined by $CD45RA^+CD62L^+CD95^{neg}$ $CCR7^+$ $T_{EMRA}$ ($CD45RA^+$ $CD62L^{neg}CD95^{neg}$ $CCR7^{neg}$), $T_{EM}$ ($CD45RA^{neg}CD62L^{neg}CD95^+$ $CCR7^{neg}$) and $T_{CM}$ ($CD45RAnegCD62L^+CD95^+CCR7^+$) and co-express CD27 and CD28 to engage co-stimulatory ligands for long term survival (FIGS. 14A-14B).

Transcriptional Profile of iCaspase $9^+$ CD123-Specific CAR T Cells.

Transcriptional profile of $CAR^+$ T cells was assessed by nanostring digital multiplex array of mRNA showed expression of T cell activation markers CD69, CD44, TIM3, co-stimulatory molecules CD40L, CD27 CD28 and no expression of exhaustion and terminal differentiation markers above detectable levels B3GAT1 (Beta-1, 3-Glucuronyltra nsferase-1; CD57) and KLRG1 (KLRG1) by CAR T cells shows they are fully activated and has the potential for persistence after adoptive transfer (FIG. 15A). Concurrent expression of transcription factors associated with less differentiated phenotype ie. ID2 (Inhibitor of DNA Binding-2), KLF2 (Kruppel-like Factor-2), FOXO1 (Forkhead Box-O1), CTNNB1 (β-Catenin), BACH2 (BTB and CNC Homology-2), GFI1 (Growth Factor Independence-1), LEF1 (Lymphoid Enhancer Binding Factor-1) and later memory stages, i.e. BCL6 (B-cell Lymohoma-6), PRDM1 (BLIMP-1), and TBX21 (T-bet), suggests that the expanded $CAR^+$ T cells were heterogeneous in memory regulation (FIG. 15B). Expression of cytokine receptors e.g., IL2RA (IL-2-Receptor-α; CD25), IL2RB (IL-2-Receptor-β; CD122), IL2RG (IL-2-Receptor-γ; CD132), IL7R (IL-7-Receptor-α; CD127), and IL15RA (IL-15-Receptor-α), suggests that CAR T cells has potential for continuous survival and persistence after adoptive transfer. CAR T cells express molecules associated with T cell effector (Granzyme A, Granzyme B, Perforin 1, Granulysin, IFN-γ and TNF) memory and trafficldng (SELL (L-Selectin; CD62L), CD95, CCR7) predicts homing, persistence and therapeutic efficiency of CAR T cells (FIG. 15C). In summary, APC expanded, IL2/IL21 supplemented CAR T cells contain subpopulations with desirable phenotype, and gene expression patterns predictive of therapeutic efficacy after adoptive transfer.

In Vitro Functionality of iCaspase $9^+$ CD123-Specific CAR T Cells.

Before testing functionality of CAR T cells, CD123 expression was evaluated on AML cell lines MV4-11, TF1, Molm-13, OCI-AML3 and mouse T cell lymphoma cell line $CD123^{neg}$ EL4-parental (EL4-P) and EL4-P transfected with CD123 antigen. All the cell lines tested were positive for CD123 except EL4-P cells and OCI-Ly19 (FIG. 16A). To evaluate functionality of CD123-specific $CAR^+$ T cells in vitro, 4 hour chromium release assay was used for AML cell lines and flow-cytometry based killing assay was used for AML primary cells. CD123-specific T cells were able to lyse $CD123^+$ AML cell lines but did not kill $CD123^{neg}$ B-cell lymphoma cell line OCI-Ly19. To provide further evidence that CD123-specific T cells specifically target $CD123^+$ tumors, EL4 parental cell lines were genetically modified to enforce CD123 expression. CD123-specific T cells efficiently killed EL4-CD123 but not EL4 parental cells (FIG. 16B).

In order to assess killing efficacy in primary patient samples, CD123 expression was analyzed on primary samples by flow cytometry (FIG. 17A). All 4 primary samples do not express CD19 (data not shown). CAR T cells were co-cultured with PKH-26 labeled $CD123^+$ primary AML cells in E:T ratio 2:1 for 72 hours and CD19 CAR T cells were used as negative control. CD123-specific T cells recognized and killed $CD123^+$ AML primary cells but not in $CD19^{neg}$ AML primary cells co-cultured with CD19 CAR T cells (FIG. 17B). iCaspase 9 expression on CAR T cells was assessed by flow cytometry (FIG. 18A) and in vitro functionality of iCasp9 was assessed by treating CAR T cells with 100 nM chemical inducer of dimerization (CID) a synthetic homo-dimerizer AP20187 for 24 hours. Untreated CAR T cells was used as negative control. Within 24 hours the dimerizer drug rapidly eliminated CAR T cells in CID treated group (FIG. 18B) compared to untreated control. In summary CD123-specific CAR T cells demonstrated anti-tumor efficacy in $CD123^+$ cell lines and primary tumors, and conditionally ablated CAR T cells.

In Vivo Efficacy of iCaspase $9^+$ CD123-Specific CAR T Cells.

Figure 19B:
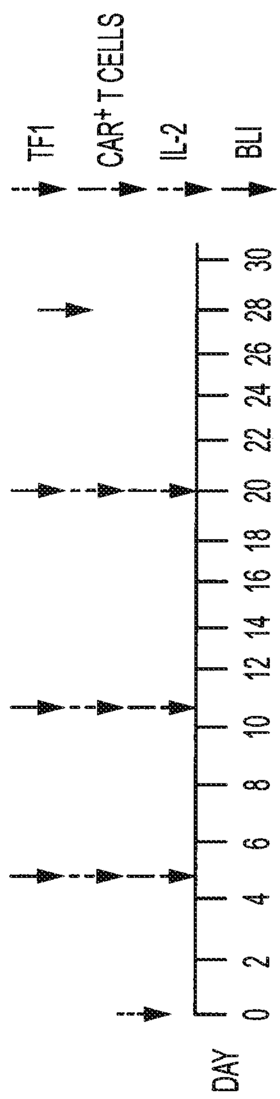
Figure 19C:
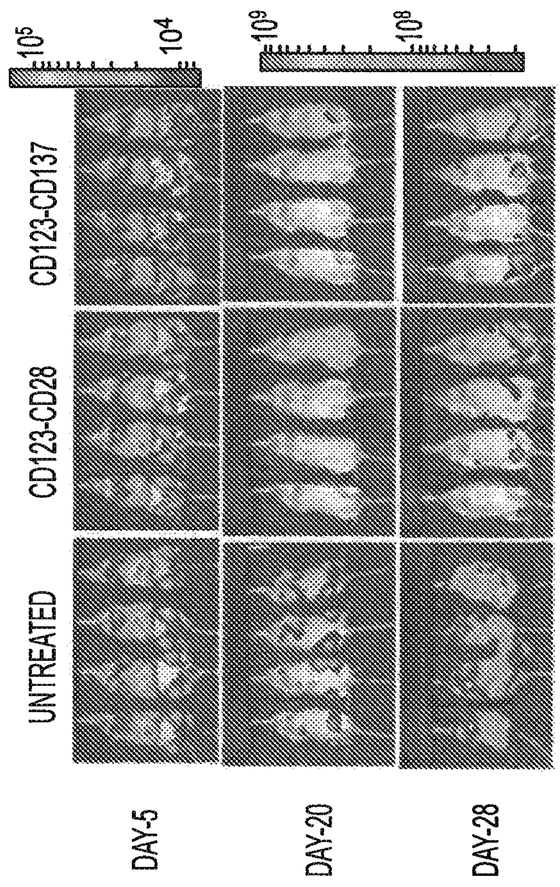
Figure 19A:
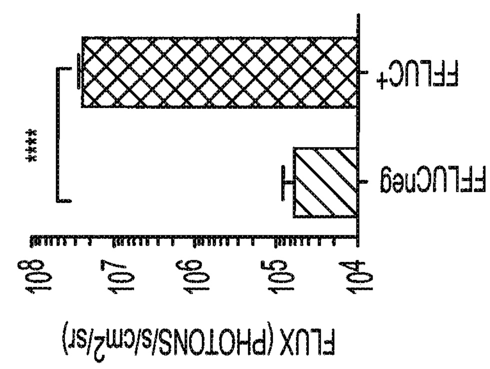
Figure 19D:
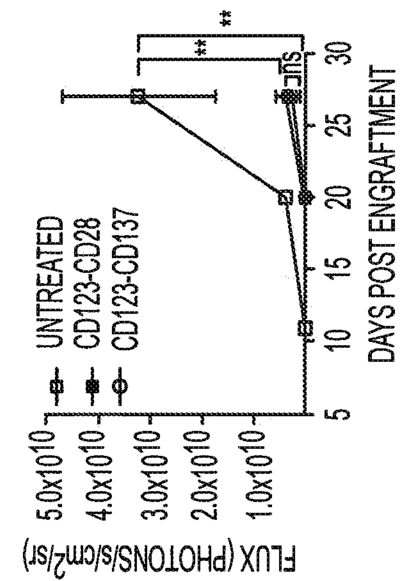
Figure 19E:
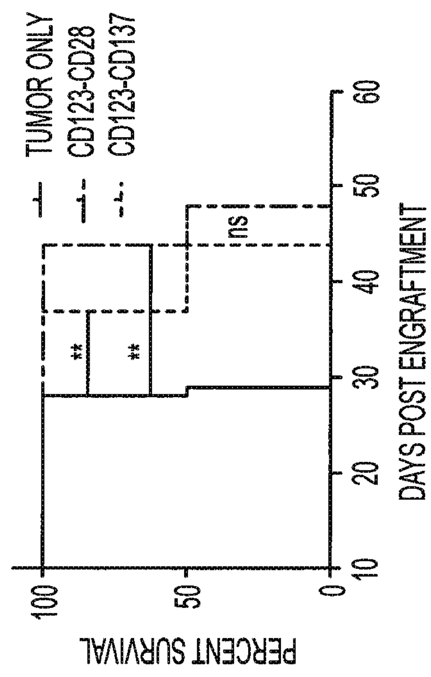
Figure 19F:
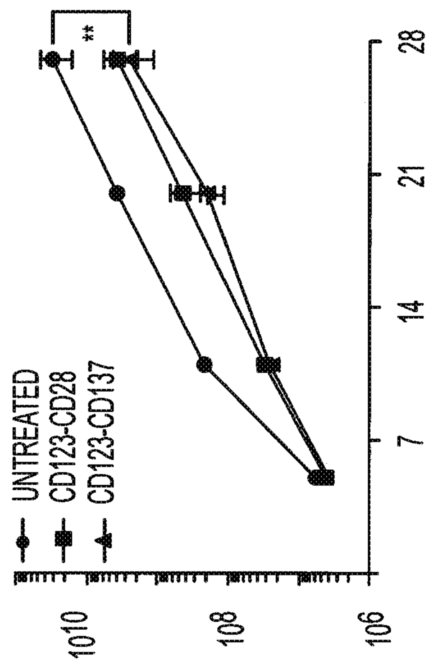

To evaluate antitumor activity of CAR T cells in vivo, a xenograft model of AML was established in NSG mice genetically engineered for human interleukin-3 (IL-3), stem cell factor, and granulocyte macrophage colony-stimulating factor (NSGS). GMCSF dependent erythrocytic leukemia cell line TF1 was genetically modified with lentiviral particles to express mKate red fluorescent protein (RFP) and enhanced firefly luciferase (ffLuc) (FIG. 19A) for allowing to track tumor burden by serial non-invasive bioluminescence imaging (BLI). On day 0 mice were injected with $2.5\times10^6$ TF1-mKate-ffluc cells allowed to engraft for 5 days. On day 5 tumor engraftment confirmed by BLI and $10^7$ CD123-CD28 or CD123-CD137 $CAR^+$ T cells/mice were infused along with intraperitoneal injection of IL-2 (60,000 units/mice). Untreated mice served as control. 2 more infusion of T cells were given on day 11 and 20 and mice were imaged for tumor burden on day 20 and 28 (FIG. 19B). Untreated mice showed continuous tumor growth evidenced by increase in bioluminescence flux in comparison to CAR T cells treated group (FIG. 19C). Both CD123-CD28 and CD123-CD137 CAR T cells treated groups were able to reduce tumor burden compared to untreated group as measured by tumor BLI flux $p<0.01$ (FIG. 19D). Treatments with CD123-specific CAR T cells significantly prolonged survival of mice in both treated groups compared to control group (FIG. 19E). However, a statistically significant difference in survival between mice treated with CD123-CD28 and CD123-CD137 CAR T cells (p value>0.05) was not observed.

Example 3—Targeting Leukemic Stem Cells by CD123-Specific CAR T Cells

In vitro killing efficacy of CD123-specific chimeric CAR T cells targeting leukemic stem cells was evaluated in AML and normal hematopoietic cells.

CD123 is Frequently Expressed in AML and Leukemic Stem Cells.

In order to decide whether CD123 is a suitable target for CAR therapy in AML, CD123 expression levels were determined in 30 random primary AML patient samples. Peripheral blood samples of 30 patients were processed for mononuclear cells (MNCs) established protocols. Samples include treated non-treated and relapsed patients. FAB classification was not available for some of the patients. MNCs from each patient were stained with CD34, CD38 and CD123 antibodies. CD123 expression levels were assessed on LSC enriched fraction ($CD34^+$ $CD38^{neg}$) fraction (FIG. 20A) and blasts ($CD38^+$) population (FIG. 20B). In AML patients, the percentages of total $CD34^+$ cells, $CD34^+$ $CD38^+$ cells, and $CD34^+$ $CD38^{neg}$ $CD34^{neg}CD38^+$ cells within the MNC fraction was highly heterogeneous. However, consistent with previous reports, CD123 was frequently expressed on more than 95% of AML samples (FIG. 21). A list of patients samples used in the study and total % of CD123 on each sample is given in Table2 below.

TABLE 2

Patient Data.

| S. No | Patient | FAB | $CD123^+$ (%) |
|---|---|---|---|
| 1 | 5480 | Relapsed | 92 |
| 2 | 3469 | Relapsed | 72 |
| 3 | 2842 | AML-TR | 82 |
| 4 | 5586 | AML-MRC | 45 |
| 5 | 5812 | AML-TR | 97 |
| 6 | 6280 | AML | 76 |
| 7 | 6430 | Relapsed | 92 |
| 8 | 3162 | M4 | 90 |
| 9 | 6542 | AML | 19 |
| 10 | 3206 | MRC treated | 99 |
| 11 | 3385 | AML-TR | 94 |
| 12 | 5402 | AML | 40 |
| 13 | 5595 | M1 | 92 |
| 14 | 6059 | AML-M5a | 86 |
| 15 | 3515 | N/A | 91 |
| 16 | 5703 | M5a | 46 |
| 17 | 5757 | AML-MRC | 28 |
| 18 | 6037 | M5a | 12 |
| 19 | 3107 | MRC | 31 |
| 20 | 1983 | M2 | 92 |
| 21 | 1929 | M5 | 92 |
| 22 | 2004 | M4 | 94 |
| 23 | 1592 | N/A | 78 |
| 24 | 6246 | AML-treated | 86 |
| 25 | 2842 | relapsed | 93 |
| 26 | AML-1 | N/A | 94 |
| 27 | AML-2 | N/A | 76 |
| 28 | AML-3 | N/A | 96 |
| 29 | AML-4 | N/A | 96 |
| 30 | AML-5 | N/A | 93 |

Leukemic Stem Cells Express CD123.

To determine whether CD123 is expressed on AML-LSCs, $CD34^+CD38^{neg}$ cells were isolated from $lin^{neg}$ fraction of primary AML samples HTB numbers 5480, 6280, 6430, 2842, 5586, 5512. Four relapsed samples and two samples with high blast counts were chosen. The analysis indicated that LSCs are enriched in relapsed patients (HTB2842, HTB5480, HTB6430 and HTB6280). Percentage of $CD34^+CD38^{neg}$ cells is more in relapsed patients than the patients with higher blast count (HTB 5586 and HTB 5812). To isolate LSCs, $lin^{neg}$ cells were isolated from MNCs of patient samples with CD34 diamond isolation kit (Miltenyi), next FACS sorted into $CD34^+CD38^{neg}$ population and stained with CD123 antibody with appropriate isotype controls. CD123 is expressed in all the samples tested (FIG. 21). Contrary to previous reports, CD123 expression was no higher on phenotypically defined leukemic stem cells. These results suggests that CD123 may be a therapeutic target in AML given its frequent expression on LSCs.

In vitro cytotoxicity of chimeric CAR T cells against AML-LSCs and normal hematopoietic cells. Human HSCs express lineage associated genes during their differentiation into blood cells. However, HSCs are generally regarded as being devoid of lineage specific markers expressed by differentiated blood cells. Studies in mice indicate that well established myeloid lineage associated markers CD33, CD13, CD123 are expressed on long-term repopulating HSCs from cord blood and BM. This finding raises the concern that myeloid antigen targeted therapies has the potential of killing HSCs (155). To determine whether chimeric CARs target normal hematopoietic stem cells and progenitors, lineage positive and negative cells were isolated from normal BM samples, $Lineage^+$ and HSCs ($lin^{neg}$ $CD34^+CD38^{neg}$) from cord blood MNCs and co-cultured with chimeric CAR T cells in E:T ratio 1:1 for 48 hours. in vitro toxicity by CAR T cells was observed in lineage positive and lineage negative cells from BM (FIG. 22A). However HSCs and lineage positive cells from cord blood showed minimal lysis by CAR T cells. (FIG. 22B). Next, anti-tumor efficacy was determined in freshly isolated phenotypically defined $lin^{neg}$ $CD34^+CD38^{neg}$ AML-LSCs with similar co-culture conditions used for hematopoietic cells.

Example 4—Expansion of LSC Under Hypoxia

Reports suggests that LSCs reside in hypoxic regions of BM microenvironment in quiescent stage and resistant to conventional treatments. It has been demonstrated that intravenously injected AML-LSCs home to BM engraft and subsequently reside in endosteal regions. Therefore novel approached are needed to target LSCs in hypoxic regions of BM niche thereby preventing relapse and therapy failure (167). LSCs are rare and few in number in AML which limits the feasibility of cell-based assays. Current culture conditions do not prevent LSCs and HSCs from differentiation. It has been shown that Aryl hydrocarbon receptor (AHR) pathway is inactive in vivo and rapidly activated in vitro in HSCs and LSCs. Stem regeninl (SR1) is an antagonist of the aryl hydrocarbon receptor that promotes the self-renewal of human I-ISCs and LSCs in culture supplemented by cytokines and prevents their differentiation (168, 169).

To expand LSCs under hypoxic conditions, $lin^{neg}$ $CD34^+$ $CD38^{neg}$ fraction was isolated from relapsed AML patients cultured at 1% oxygen and 5% $CO_2$. Cells were cultured in serum free stemspanII media (stem cell technologies) in presence SR1 1 μM/ml supplemented by cytokines stem cell factor (SCF), human FLT3 ligand, interleukin-3 for 7 days. SR1 non treated cells used as control. All AML-LSCs treated with SR1 showed higher percentages of $CD34^+CD38^{neg}$ fraction with relative CD123 expression after a 7-day culture period compared to SR1 non treated controls (FIG. 24). On day 7, LSCs were labeled with PKH26 and co-cultured with CD123– specific chimeric CAR T cells in 1:1 ratio for 48 hours under hypoxic conditions. CD19 CAR T cells used as negative control. CD23-specific CAR T cells lysed LSCs expanded under hypoxia compared to CD19 CAR which exhibited minimal lysis (FIG. 25).

These in vitro data suggests that CAR therapy can be detrimental to normal hematopoiesis and CD123-specific CAR T cells need to be employed with rescue strategies such as myeloablation as conditioning regimen for HSC transplantation.

Example 5—Materials and Methods

Primary Samples and Animal Use

All patient samples used for this study were obtained after written informed consent was granted in accordance with protocols established and approved by the MD Anderson Cancer Center (MDACC) and Internal Review Board (IRB). The identities of all samples were kept private. Animals were handle d in accordance with the strict guidelines established by the MDACC Institutional Animal Care and Use Committee (IACUC).

Generation of CD123 Specific CARs with Chimeric scFvs

Six second generation CARs with chimeric scFvs were generated by mix and matching $V_L$ and $V_H$ chains of mAbs 26292, 32701, 32703 and 32716 specific to CD123. CARs derived from scFvs of mAbs were used as positive control. All the scFvs except CAR-10 were fused in frame to CD3ζ and CD28 endo domains via CD8α and CD8 transmembrane domain whereas IgG4 and CD28TM were used for CAR-10. CAR constructs were custom synthesized and cloned into sleeping beauty system.

Construction of iCaspase $9^+$ CARs in SB Transposons

Two SB Transposons containing codon optimized (CoOp) second generation CARs specific for human CD123 flanked by inverted repeats to CD3ζ via CD28 or CD137 have been generated as described previously (22-23). Briefly, the scFv specific to CD123 is created by joining heavy chain of clone 32703 with light chain of clone 26292 (CAR 10 FIG. 1A) through a flexible linker. The chimeric scFv is in turn fused to signaling domains CD28 or CD137 and CD3ζ via IgG4 hinge and CD28 transmembrane domain in frame with iCaspase 9 through oligonucleotide encoding F2A peptide. The CAR constructs were custom synthesized and codon optimized by Geneart, (Invitrogen, Grand Island, N.Y.) into CD19 CAR constructs. The sequence for both plasmids was verified by Sanger sequencing (DNA Sequencing Core, MDACC).

Primary Cells and Cell Lines

TF1 cell line was obtained from European collection cell cultures (ECACC), Molml3, MV411, AML-10 and OCI-AML3 were obtained from Prof. Dean A. Lee (MD Anderson Cancer Center (MDACC)). EL4 cell were obtained from ATCC. RCH-ACV and Kasumi-2 were a gift from Jeffrey Tyner (Oregon Health & Science University). OCI-Ly19 was a kind gift from Prof. Richard Eric Davis (MDACC). K562-derived aAPC were obtained from Dr. Carl H. June, University of Pennsylvania (UPenn) and further modified with mL15 and tumor associated antigens ROR1 and CD123. Nalm6 cell line was obtained from NALM-6 Deutsche Sammlung von Mikroorganismen und Zellkulturen (DSMZ). Peripheral blood mononuclear cells (PBMC) for T cell transfections were obtained from healthy donors after informed consent. PBMC were isolated by density gradient centrifugation using FICOLL-PAQUE™ PLUS (GE Healthcare). All cell lines were maintained in complete RPMI media, 10% FBS and 1× Glutamax-100. STR DNA Fingerprinting was done to confirm the identity of all cell lines at MDACC's Cancer Center Support Grant (CCSG) supported facility "Characterized Cell Line Core."

Generation of $CD123^+$ Clone1-APC and EL4 aAPC Clone 9 was generated by enforced expression of CD19, CD64, CD86, and CD137L on K562 cells (June CH, UPenn). Clone 9 was further modified to express IL15/IL15Rα fusion protein (FIG. 26A), CD64, ROR1 (FIG. 26B), and CD123 (FIG. 26C, designated Clone1-CD123). K562-clone 1 and EL4 were transfected with CD123 SB plasmid (FIGS. 11A-C) and transposase pCMV-SB11 with AMAXA® Cell Line NUCLEOFECTOR® Kit V (Lonza, cat.no VCA-1003) according to manufacture instructions. Briefly 1 million K562-clone1 and EL4 cells were mixed with 3 g of CD123 SB plasmid and 1 μg of SB transposase and transfected with NUCLEOFECTOR® Program U16. $CD123^+$ cells were selected by hygromycin selection.

Electroporation and Propagation of CAR T Cells

On day 0, 20 million PBMC were resuspended in 100 μL of Amaxa human T cell Nucleofector solution (Cat. no. VPA-1002; Lonza, Basel, Switzerland) mixed with 15 μg of transposon and 5 μg of transposase (pKan-CMV-SB11) and electroporated using Program U-14. The following day (day1) cells were counted, surface stained for CAR expression by Fc antibody and stimulated with γ-irradiated (100 Gy) Clone 1-CD123 at 1:2 ratio of T cells to AaPCs. Cultures were supplemented with recombinant human IL-2 50 units/ml and 30 ng/ml of recombinant human IL-21 (Pepro Tech). AaPCs added every 7 days and IL-2, IL-21 added Monday-Wednesday and F riday schedule beginning of day 1 of each 7 day T cell expansion cycle. T cell cultures were phenotyped every week to monitor CAR expression and outgrowth of NK cells ($CD3^{neg}CD56^+$ population) usually occurred between 10 to 14 days after electroporation. If the percentage of NK cells exceeded approximately 10% total population, depletion of NK cells was carried out with CD56 beads (cat.no. 130-050-401, Miltenyi Biotech) according to manufacture instructions. As a control, $5\times10^6$ PBMC were mock transfected with nucleofector solution without CAR plasmid and were co-cultured on γ-irradiated (100 Gy) anti-CD3 (OKT3) loaded K562-aAPC clone #1 at a ratio of 1:1 in a 7-day stimulation cycle along with similar concentrations of IL-2 and IL-21 as CAR T cells.

Real Time PCR to Determine Integrated CAR Copy Number

The number of integrated copies of CD123-specific CAR genes was determined by isolating genomic DNA using AllPrep DNA/RNA Mini Kit, (Qiagen cat #80204) as described in (25). Briefly about 50-100 ng of DNA amplified using Steponeplus Real-time PCR system (Applied Biosystems), forward primer (5'-CAGCGACGGCAGCTTCTT-3' (SEQ ID NO: 9)), reverse primer (5'-TGCATCACGGAGCTAAA-3' (SEQ ID NO: 10)) and carboxyfluoresce in (FAM)-labeled probe and (5'-AGAGCCGGTGGCAGG-3' (SEQ ID NO: 11)). These primers hybridize to the CAR in IgG4 and CD28 transmembrane region. Genomic DNA from a genetically modified Jurkat T-cell (clone #12) containing 1 copy of CAR per cell from CoOpCD19RCD28/pSBSO DNA plasmid was used as positive control. No DNA ($CAR^{neg}$) T cells were used as negative control. Results were analyzed using GraphPad Prism software.

Immunophenotype of $CAR^+$ T Cells

T cells were immunophenotyped using appropriate antibodies (See Table 3 below) and isotype controls. Cells were stained for 30 minutes at 4° C. followed by 2 washes with FACS buffer (PBS, 2% FBS, 0.1% sodium azide). For intracellular staining cells were fixed and permeabilized for 20 minutes at 4° C. with BD Cytofix/Cytoperm (BD Biosciences, San Diego, Calif.) followed by staining with appropriate antibodies. All samples were acquired on FACS Calibur (BD Bioscience) and analyzed with FlowJo software (version 7.6.3).

TABLE 3

Antibodies used for immunophenotyping of CD123-specific CAR T cells.

| Antibody | Catalog # | Source |
|---|---|---|
| CD123 Recombinant fused to Fc | 10518-H03H-20 | Sino biologicals |
| CD3 | 552852 | BD Biosciences |
| Fc | H10104 | Invitrogen |
| CD56 | 340410 | BD Biosciences |
| CD4 | 341654 | BD Biosciences |

TABLE 3-continued

Antibodies used for immunophenotyping of CD123-specific CAR T cells.

| Antibody | Catalog # | Source |
|---|---|---|
| CD8 | 340659 | BD Biosciences |
| CD45RA | 555488 | BD Biosciences |
| CD27 | 558664 | BD Biosciences |
| CD28 | 555729 | BD Biosciences |
| CD45RO | 555492 | BD Biosciences |
| CD62L | 555544 | BD Biosciences |
| CCR7 | 335605 | Biolegend |
| CD95 | 558814 | BD Biosciences |
| CD57 | 555619 | BD Biosciences |
| PD1 | 557860 | BD Biosciences |
| CXCR4 | 555974 | BD Biosciences |

Multiplex Gene Expression Analysis of CAR T Cells

On day 35 of co-culture of CAR T cells on AaPC about $10^5$ were lysed in 17 μl of RLT buffer (Qiagen) and frozen at −80° C. Cell lysates were thawed and analyzed immediately using nCounter analysis System (NanoString Technologies, Seattle, Wash.) with the lymphocyte code-set array as described in Table 4 below (26). Data was normalized to spike positive control RNA and housekeeping genes (ACTB, G6PD, OAZ1, POLR1B, POLR2A, RPL27, Rpsl3, and TBP) where 2 normalization factors were calculated and applied to the raw counts. Each normalization factor was calculated from the average of sum of all samples divided by the sum of counts for an individual sample. Total counts for LCA genes described in CD123-specific $CAR^+$ T cells were directly reported as normalized mRNA counts. Limit-of-detection (LOD) was calculated from the negative control counts and reported as the mean plus two-times the standard deviation (mean+2×SD) and shown as dashed lines in graphs of mRNA data.

TABLE 4

Lymphocyte code-set array.

| Gene ID | Accession# | Target Region |
|---|---|---|
| ABCB1 | NM_000927.3 | 3910-4010 |
| ABCG2 | NM_004827.2 | 285-385 |
| ACTB | NM_001101.2 | 1010-1110 |
| ADAM19 | NM_023038.3 | 1690-1790 |
| AGER | NM_001136.3 | 340-440 |
| AHNAK | NM_001620.1 | 15420-15520 |
| AIF1 | NM_032955.1 | 315-415 |
| AIM2 | NM_004833.1 | 607-707 |
| AKT1 | NM_005163.2 | 1772-1872 |
| ALDH1A1 | NM_000689.3 | 11-111 |
| ANXA1 | NM_000700.1 | 515-615 |
| ANXA2P2 | NR_003573.1 | 257-357 |
| AP1 | NM_002228.3 | 140-240 |
| Apaf1 | NM_181869.1 | 1160-1260 |
| ARG1 | NM_000045.2 | 505-605 |
| ATM | NM_000051.3 | 30-130 |
| ATP2B4 | NM_001684.3 | 7640-7740 |
| B2M | NM_004048.2 | 25-125 |
| BACH2 | NM_021813.2 | 3395-3495 |
| BAD | NM_004322.2 | 195-295 |
| BATF | NM_006399.3 | 825-925 |
| BAX | NM_138761.2 | 694-794 |
| BCL10 | NM_003921.2 | 1250-1350 |
| Bcl2 | NM_000633.2 | 1525-1625 |
| BCL2L1 | NM_138578.1 | 1560-1660 |
| BCL2L11 | NM_138621.2 | 2825-2925 |
| Bcl6 | NM_001706.2 | 675-775 |
| Beta-arrestin (ARRB2) | NM_004313.3 | 1652-1752 |
| BHLHE41 | NM_030762.2 | 655-755 |
| BID | NM_197966.1 | 2095-2195 |

TABLE 4-continued

Lymphocyte code-set array.

| Gene ID | Accession# | Target Region |
|---|---|---|
| BIRC2 | NM_001166.3 | 1760-1860 |
| BMI1 | NM_005180.5 | 1145-1245 |
| BNIP3 | NM_004052.2 | 325-425 |
| C10RF24 | NM_052966.2 | 3526-3626 |
| C11ORF17 | NM_020642.3 | 570-670 |
| C5ORF13 | NM_001142474.1 | 990-1090 |
| C80RF70 | NM_016010.2 | 665-765 |
| CA9 | NM_001216.2 | 960-1060 |
| CASP1 | NM_033292.2 | 575-675 |
| Caspase9 | NM_052813.2 | 1850-1950 |
| CAT | NM_001752.2 | 1130-1230 |
| CCL3 | NM_002983.2 | 681-781 |
| GATA3 | NM_001002295.1 | 2835-2935 |
| Gfi1 | NM_005263.2 | 2235-2335 |
| GILZ | NM_198057.2 | 1400-1500 |
| GLIPR1 | NM_006851.2 | 255-355 |
| GLO1 | NM_006708.1 | 1240-1340 |
| GSK3B | NM_002093.2 | 925-1025 |
| GZMA | NM_006144.2 | 155-255 |
| GZMB | NM_004131.3 | 540-640 |
| GzmH | NM_033423.3 | 705-805 |
| HDAC1 | NM_004964.2 | 785-885 |
| HDAC2 | NM_001527.1 | 930-1030 |
| HES1 | NM_004649.5 | 1340-1440 |
| HLA-A | NM_002116.5 | 1000-1100 |
| HOXA10 | NM_018951.3 | 1503-1603 |
| HOXA9 | NM_152739.3 | 1015-1115 |
| HOXB3 | NM_002146.4 | 60-160 |
| HOXB4 | NM_024015.4 | 1340-1440 |
| HPRT1 | NM_000194.1 | 240-340 |
| HRH1 | NM_000861.2 | 3055-3155 |
| HRH2 | NM_022304.1 | 600-700 |
| IAP | NM_001777.3 | 897-997 |
| ICOS | NM_012092.2 | 640-740 |
| ICOSLG | NM_015259.4 | 1190-1290 |
| ID2 | NM_002166.4 | 505-605 |
| IFNa1 | NM_024013.1 | 585-685 |
| IFNG | NM_000619.2 | 970-1070 |
| IFNGR1 | NM_000416.1 | 1140-1240 |
| IGF1R | NM_000875.2 | 455-555 |
| IKZF1 | NM_006060.3 | 4485-4585 |
| IL10 | NM_000572.2 | 230-330 |
| IL10RA | NM_001558.2 | 150-250 |
| IL12A | NM_000882.2 | 775-875 |
| IL12RB1 | NM_00535.1 | 1292-1392 |
| IL12RB2 | NM_001559.2 | 1315-1415 |
| IL13 | NM_002188.2 | 516-616 |
| IL15 | NM_172174.1 | 1685-1785 |
| IL15Ra | NM_002189.2 | 39-139 |
| IL17A | NM_002190.2 | 240-340 |
| IL17F | NM_052872.3 | 210-310 |
| IL17RA | NM_014339.4 | 3020-3120 |
| IL18 | NM_001562.2 | 48-148 |
| IL18R1 | NM_003855.2 | 2025-2125 |
| IL18RAP | NM_003853.2 | 2412-2512 |
| IL2 | NM_000586.2 | 300-400 |
| IL21R | NM_021798.2 | 2080-2180 |
| IL22 | NM_020525.4 | 319-419 |
| IL23R | NM_144701.2 | 710-810 |
| IL2RA | NM_000417.1 | 1000-1100 |
| IL2RB | NM_000878.2 | 1980-2080 |
| IL2RG | NM_000206.1 | 595-695 |
| IL4 | NM_000589.2 | 625-725 |
| IL4R | NM_000418.2 | 705-805 |
| IL5 | NM_000879.2 | 105-205 |
| IL6 | NM_000600.1 | 220-320 |
| IL6R | NM_000565.2 | 993-1093 |
| IL7R | NM_002185.2 | 1610-1710 |
| IL9 | NM_000590.1 | 300-400 |
| INDO | NM_002164.3 | 50-150 |
| IRF1 | NM_002198.1 | 510-610 |
| IRF2 | NM_002199.2 | 1375-1475 |
| IRF4 | NM_002460.1 | 325-425 |
| ITGA1 | NM_181501.1 | 1875-1975 |
| ITGA4 | NM_000885.4 | 975-1075 |

TABLE 4-continued

Lymphocyte code-set array.

| Gene ID | Accession# | Target Region |
|---|---|---|
| ITGA5 | NM_002205.2 | 925-1025 |
| ITGAL | NM_002209.2 | 3905-4005 |
| ITGB1 | NM_033666.2 | 2000-2100 |
| ITK | NM_005546.3 | 3430-3530 |
| JAK1 | NM_002227.1 | 285-385 |
| JAK2 | NM_004972.2 | 455-555 |
| JAK3 | NM_000215.2 | 1715-1815 |
| JunB | NM_002229.2 | 1155-1255 |
| KIR2DL1 (NKAT1)/CD158a | NM_014218.2 | 881-981 |
| KIR2DL2 (NKAT6)/CD158b | NM_014219.2 | 814-914 |
| KIR2DL3 (NKAT2)/CD158b | NM_015868.2 | 741-841 |
| KIR2DL4 (p49CD158d) | NM_002255.5 | 15-115 |
| KIR2DL5A | NM_020535.3 | 1451-1551 |
| KIR2DS1 | NM_014512.1 | 698-798 |
| KIR2DS2 (NKAT5)/CD158b | NM_012312.2 | 856-956 |
| KIR2DS3 (NKAT7) | NM_012313.1 | 693-793 |
| KIR2DS4 (NKAT8) | NM_012314.3 | 1427-1527 |
| KIR2DS5 (NKAT9) | NM_014513.2 | 204-304 |
| KIR3DL1 (NKAT3/NK_B1) | NM_013289.2 | 1054-1154 |
| KIR3DL2 (NKAT4) | NM_006737.2 | 884-984 |
| KIR3DL3 (KIRC1CD158z) | NM_153443.3 | 508-608 |
| KIR3DS1 NKAT10) | NM_00083539. | 1000-1100 |
| KIT | NM_000222.1 | 5-105 |
| KLF10 | NM_005655.1 | 570-670 |
| Klf2 | NM_016270.2 | 1015-1115 |
| KLF4 | NM_004235.4 | 1980-2080 |
| KLF6 | NM_001008490.1 | 11651265 |
| KLRB1 | NM_002258.2 | 85-185 |
| KLRC1 | NM_002259.3 | 335-435 |
| KLRD1 (CD94) | NM_002262.3 | 542-642 |
| KLRG1 | NM_005810.3 | 45-145 |
| LAIR1 | NM_002287.3 | 1195-1295 |
| LCK | NM_005356.2 | 1260-1360 |
| LDHA | NM_005566.1 | 985-1085 |
| Lef1 | NM_016269.3 | 1165-1265 |
| LGALS3 | NM_002306.2 | 120-220 |
| LNK | NM_005475.2 | 4285-4385 |
| LOC282997 | NR_026932.1 | 665-765 |
| LRP5 | NM_002335.1 | 2515-2615 |
| LRP6 | NM_002336.1 | 2185-2285 |
| LRRC32 | NM_005512.2 | 3470-3570 |
| MAD1L1 | NM_003550.2 | 306-406 |
| MAP2K1 | NM_002755.2 | 970-1070 |
| MAPK14 | NM_001315.1 | 450-550 |
| MAPK3 | NM_002746.2 | 580-680 |
| MAPK8 | NM_139049.1 | 945-1045 |
| MCL1 | NM_021960.3 | 1260-1360 |
| MIF | NM_002415.1 | 319-419 |
| MMP14 | NM_004995.2 | 1470-1570 |
| MPL | NM_005373.2 | 895-995 |
| MYB | NM_005375.2 | 3145-3245 |
| Myc | NM_002467.3 | 1610-1710 |
| MYO6 | NM_004999.3 | 6655-6755 |
| NBEA | NM_015678.3 | 8645-8745 |
| NCAM1 | NM_000615.5 | 1620-1720 |
| NCL | NM_005381.2 | 1492-1592 |
| NFAT5 | NM_173214.1 | 3290-3390 |
| NFATC1 | NM_172390.1 | 2510-2610 |
| NFATC2 | NM_012340.3 | 1815-1915 |
| NFATC3 | NM_004555.2 | 2190-2290 |
| NKG2C | NM_002260.3 | 942-1042 |
| NKG2D | NM_007360.1 | 760-860 |
| NKG2E | NM_002261.2 | 760-860 |
| NKG2F | NM_013431.2 | 29-129 |
| NKp30 (CD337) | NM_147130.1 | 50-150 |
| NKp44 (CD336) | NM_004828.3 | 798-898 |
| NKp46 (CD335) | NM_001145457.1 | 145-245 |
| NKp80 | NM_016523.1 | 275-375 |
| NOS2 | NM_000625.4 | 605-705 |
| Notch1 | NM_017617.3 | 735-835 |
| NR3C1 | NM_001018077.1 | 1665-1765 |
| NR4A1 | NM_002135.3 | 155-255 |
| NRIP1 | NM_003489.2 | 335-435 |
| NT5E | NM_00526.2 | 1214-1314 |
| OPTN | NM_001008211.1 | 625-725 |
| P2RX7 | NM_002562.4 | 340-440 |
| p38 | NM_006303.3 | 507-607 |
| Pax5 | NM_016734.1 | 2288-2388 |
| PDCD1 | NM_005018.1 | 175-275 |
| PDCD1LG2 | NM_025239.3 | 235-335 |
| PDE3 | NM_000921.3 | 3010-3110 |
| PDE4 | NM_001111307.1 | 3855-3955 |
| PDE7 | NM_002604.2 | 2210-2310 |
| PDK1 | NM_002610.3 | 1170-1270 |
| PECAM1 | NM_000442.3 | 1365-1465 |
| PHACTR2 | NM_001100164.1 | 8350-8450 |
| PHC1 | NM_004426.2 | 2905-3005 |
| POP5 | NM_015918.3 | 560-660 |
| PPARA | NM_001001928.2 | 5220-5320 |
| PPP2R1A | NM_014225.3 | 1440-1540 |
| PRDM1 | NM_182907.1 | 310-410 |
| PRF1 | NM_005041.3 | 2120-2220 |
| PROM1 | NM_006017.1 | 925-1025 |
| PTGER2 | NM_000956.2 | 1410-1510 |
| PTK2 | NM_005607.3 | 1005-1105 |
| PTPRK | NM_001135648.1 | 43154415 |
| RAC1 | NM_198829.1 | 1250-1350 |
| RAC2 | NM_002872.3 | 1069-1169 |
| RAP46 | NM_004323.3 | 1490-1590 |
| RARA | NM_000964.2 | 115-215 |
| RHOA | NM_001664.2 | 1230-1330 |
| RORA | NM_134261.2 | 1715-1815 |
| RORC | NM_001001523.1 | 1350-1450 |
| RUNX1 | NM_001754.4 | 635-735 |
| RUNX2 | NM_004348.3 | 1850-1950 |
| S100A4 | NM_002961.2 | 263-363 |
| SATB1 | NM_001131010.1 | 1335-1435 |
| SCAP2 | NM_003930.3 | 3374-3474 |
| SCML1 | NM_001037540.1 | 925-1025 |
| SCML2 | NM_006089.2 | 360-460 |
| SEL1L | NM_005065.4 | 980-1080 |
| SELL | NM_000655.3 | 110-210 |
| SERPINE2 | NM_006216.2 | 240-340 |
| SHP-1 | NM_002831.5 | 1734-1834 |
| SIT1 | NM_014450.2 | 720-820 |
| SLA2 | NM_032214.2 | 1640-1740 |
| SLAMF1 | NM_003037.2 | 580-680 |
| SLAMF7 | NM_021181.3 | 215-315 |
| SLC2A1 | NM_006516.2 | 2500-2600 |
| SMAD3 | NM_005902.3 | 4220-4320 |
| SNAI1 | NM_005985.2 | 63-163 |
| SOD1 | NM_000454.4 | 35-135 |
| SPI1 | NM_003120.1 | 730-830 |
| STAT1 | NM_007315.2 | 205-305 |
| STAT3 | NM_139276.2 | 4535-4635 |
| STAT4 | NM_003151.2 | 789-889 |
| STAT5A | NM_003152.2 | 3460-3560 |
| STAT5B | NM_012448.3 | 200-300 |
| Stat6 | NM_003153.3 | 2030-2130 |
| STMN1 | NM_203401.1 | 287-387 |
| TBX21 | NM_013351.1 | 890-990 |
| TBXA2R | NM_001060.3 | 385-485 |
| Tcf7 | NM_003202.2 | 2420-2520 |
| TDGF1 | NM_003212.2 | 1567-1667 |
| TDO2 | NM_005651.1 | 0-100 |
| TEK | NM_000459.2 | 615-715 |
| TERT | NM_198253.1 | 2570-2670 |
| TF | NM_001063.2 | 640-740 |
| TFRC | NM_003234.1 | 1220-1320 |
| TGFA | NM_003236.2 | 780-880 |

TABLE 4-continued

| Lymphocyte code-set array. | | |
|---|---|---|
| Gene ID | Accession# | Target Region |
| TGFB1 | NM_000660.3 | 1260-1360 |
| TGFB2 | NM_003238.2 | 1125-1225 |
| TGFBR1 | NM_004612.2 | 4280-4380 |
| TIE1 | NM_005424.2 | 2610-2710 |
| TLR2 | NM_003264.3 | 180-280 |
| TLR8 | NM_138636.3 | 2795-2895 |
| TNF | NM_000594.2 | 1010-1110 |
| TNFRSF18 | NM_004195.2 | 445-545 |
| TNFRSF1B | NM_001066.2 | 835-935 |
| TNFRSF4 | NM_003327.2 | 200-300 |
| TNFRSF7 | NM_001242.4 | 330-430 |
| TNFRSF9 | NM_001561.4 | 255-355 |
| TNFSF10 | NM_003810.2 | 115-215 |
| TNFSF14 | NM_003807.2 | 270-370 |
| TOX | NM_014729.2 | 3950-4050 |
| TP53 | NM_000546.2 | 1330-1430 |
| TRAF1 | NM_005658.3 | 3735-3835 |
| TRAF2 | NM_021138.3 | 1325-1425 |
| TRAF3 | NM_145725.1 | 1795-1895 |
| TSLP | NM_033035.3 | 395-495 |
| TYK2 | NM_003331.3 | 485-585 |
| VEGFA | NM_001025366.1 | 1325-1425 |
| WEE1 | NM_003390.2 | 5-105 |
| ZAP70 | NM_001079.3 | 1175-1275 |
| ZNF516 | NM_014643.2 | 4830-4930 |
| p16 | NM_000077.3 | 95-1075 |
| SHP2 | NM_002834.3 | 4650-4750 |
| CD57/B3GAT1 | NM_018644.3 | 145-245 |
| CD85/LILRB1 | NM_001081637.1 | 2332-2432 |
| Neil1 | NM_024608.2 | 1675-1775 |
| Neil2 | NM_145043.2 | 2570-2670 |
| PNK | NM_003681.3 | 580-680 |
| POLR2A | NM_000937.2 | 3775-3875 |
| POLR1B | NM_019014.3 | 3320-3420 |
| IL-1alpha | NM_000575.3 | 1085-1185 |
| IL-1beta | NM_000576.2 | 840-940 |
| IL-12p40 | NM_002187.2 | 1435-1535 |
| Raf-1 | NM_002880.2 | 1990-2090 |
| IL-23p19 | NM_016584.2 | 411-511 |
| gBAD-1R_scfv | SCFV001.1 | 1-101 |
| CD20 scfv rutuximab | SCFV002.1 | 8-108 |
| c-MET_scfv | SCFV004.1 | 138-238 |
| CD45R_scfv | SCFV006.1 | 222-322 |
| Thymidine_kinase | SCFV007.1 | 100-200 |
| CD56R_scfv | SCFV008.1 | 197-297 |
| Human CD19R_scfv | SCFV009.1 | 215-315 |
| DECTIN-1R | SCFV010.1 | 270-370 |
| HERVK6H5scfv | SCFV012.1 | 137-237 |
| CD19Rscfv | SCFV013.1 | 204-304 |
| HER2scfv | SCFV014.1 | 64-164 |
| EGFRscfv_NIMOCAR | SCFV015.1 | 7-107 |
| RPL27 | NM_000988.3 | 23-123 |
| OAZ1 | NM_004152.2 | 313-413 |
| GABPa | NM_002040.3 | 1160-1260 |
| XBP-1 | NM_005080.2 | 440-540 |
| MBD2 | NM_003927.3 | 2015-2115 |
| Bcl6b | NM_181844.3 | 2135-2235 |
| TSLP-R | NM_022148.2 | 1420-1520 |
| BTLA | NM_001085357.1 | 890-990 |
| HVEM | NM_003820.2 | 916-1016 |
| LTbR | NM_002342.1 | 1435-1535 |
| CD43 | NM_001030288.1 | 2798-2898 |
| mTOR | NM_004958.2 | 5095-5195 |
| AMPK | NM_006252.2 | 975-1075 |
| SIP1 | NM_001009182.1 | 537-637 |
| EphA2 | NM_004431.2 | 1525-1625 |
| CD254 | NM_003701.2 | 490-590 |
| BCLxL | NM_001191.2 | 260-360 |
| Xbp1 | NM_001079539.1 | 935-1035 |
| IL27 | NM_145659.3 | 143-243 |
| IKZF2 | NM_001079526.1 | 945-1045 |
| GNLY | NM_006433.2 | 305-405 |
| NFkB | NM_001165412.1 | 2305-2405 |
| GADD45α | NM_001924.2 | 865-965 |

TABLE 4-continued

| Lymphocyte code-set array. | | |
|---|---|---|
| Gene ID | Accession# | Target Region |
| GADD45β | NM_015675.2 | 365-465 |
| ATF3 | NM_001030287.2 | 600-700 |
| MAD | NM_002357.2 | 880-980 |
| Crem | NM_001881.2 | 260-360 |
| SOCS1 | NM_003745.1 | 1025-1125 |
| SOCS3 | NM_003955.3 | 1870-1970 |
| DUSP16 | NM_030640.2 | 615-715 |
| Rps13 | NM_001017.2 | 331-431 |
| TBP | NM_003194.3 | 25-125 |
| G6PD | NM_000402.2 | 1155-1255 |
| Rbpms | NM_001008710.1 | 842-942 |
| KLF7 | NM_001270943.1 | 1546-1646 |
| Vax2 | NM_012476.2 | 871-971 |
| RUNX3 | NM_004350.1 | 2085-2185 |
| ERK | NM_01449.2 | 785-885 |
| ITCH | NM_031483.4 | 155-255 |
| CBLB | NM_170662.3 | 3195-3295 |
| DGKA | NM_001345.4 | 1375-1475 |
| LTA | NM_000595.2 | 885-985 |
| FoxP1 | NM_032682.5 | 6758-6858 |
| CD223 (LAG3) | NM_002286.5 | 1735-1835 |
| CD118 | NM_002310.3 | 2995-3095 |
| Txk | NM_003328.1 | 800-900 |
| Prkcq | NM_006257.2 | 1325-1425 |
| STS2 (Ubash3a) | NM_001895.1 | 1970-2070 |
| RNF125 | NM_017831.3 | 790-890 |
| Lat | NM_001014987.1 | 1290-1390 |
| Skap1 | NM_003726.3 | 1360-1460 |
| Dok2 | NM_003974.2 | 650-750 |
| Axin2 | NM_004655.3 | 1035-1135 |
| Sh2d2a | NM_001161443.1 | 341-441 |
| Klra5 (Ly49E) | NR_028045.1 | 414-514 |
| CD7 | NM_006137.6 | 440-540 |
| CD11c | NM_000887.3 | 700-800 |
| Syk | NM_003177.3 | 1685-1785 |
| Lyn | NM_002350.1 | 1285-1385 |
| Lat2 | NM_014146.3 | 1863-1963 |
| Clnk | NM_052964.2 | 1108-1208 |
| Car2 | NM_000067.2 | 575-675 |
| Fgl2 | NM_006682.2 | 250-350 |
| cathepsinC | NM_001114173.1 | 260-360 |
| CathepsinD | NM_001909.3 | 1495-1595 |
| Rab31 | NM_006868.3 | 3800-3900 |
| Spry2 | NM_005842.2 | 85-185 |
| S100A6 | NM_014624.3 | 539-639 |
| Lgals1 | NM_002305.3 | 60-160 |
| Hmgb2 | NM_001130688.1 | 125-225 |
| HopX | NM_001145460.1 | 1117-1217 |
| Dock5 | NM_024940.6 | 630-730 |
| Ptpn4 | NM_002830.2 | 705-805 |
| PLZF | NM_006006.4 | 1585-1685 |
| Foxo1 | NM_002015.3 | 1526-1626 |
| Foxo3 | NM_001455.2 | 1860-1960 |
| ID3 | NM_002167.3 | 195-295 |
| ZEB2 | NM_014795.2 | 20-120 |
| SMAD4 | NM_005359.3 | 1370-1470 |
| YAP | NM_139118.2 | 755-855 |
| E2A | NM_003200.2 | 4325-4425 |
| Nanog | NM_024865.2 | 1100-1200 |
| OCT4 | NM_002701.4 | 1225-1325 |
| Sox2 | NM_003106.2 | 151-251 |
| TAL1 | NM_003189.2 | 4635-4735 |
| ELF1 | NM_032377.3 | 125-225 |
| SOX13 | NM_005686.2 | 3039-3139 |
| Nrp1 | NM_003873.5 | 370-470 |
| Blk | NM_001715.2 | 990-1090 |
| CCR10 | NM_001296.3 | 1345-1445 |
| ITGB7 | NM_000889.1 | 1278-1378 |
| Sox5 | NM_152989.2 | 1885-1985 |
| Bcl11b | NM_022898.1 | 3420-3520 |
| SOX4 | NM_003107.2 | 3040-3140 |
| Tcfl2 | NM_207037.1 | 1105-1205 |

TABLE 4-continued

Lymphocyte code-set array.

| Gene ID | Accession# | Target Region |
|---|---|---|
| Dapl1 | NM_001017920.2 | 190-290 |
| Trf | NM_003218.3 | 1037-1137 |
| Cpt1 | NM_020244.2 | 1303-1403 |
| Bim | NM_138621.4 | 257-357 |
| C-flip | NM_001127183.1 | 653-753 |

iCaspase 9 Functional Assay

CAR+ T cells with and without iCaspase 9 were seeded in 24 well plate @ $10^6$ cells/well. 1 μM of chemical inducer of dimerization (CID) (AP20187; Clontech) was added, cells were harvested after 24 hours and surface stained with CD3, FC followed by annexin-V and 7-amino-actinomyc in D (7-AAD) for 15 minutes according to the manufacturer's instructions (BD Pharmingen). Within 1 hour after staining, cells were analyzed by flow cytometry using BD FACS caliber.

Chromium Release Assay

The cytolytic efficacy of CAR+ T cells with target cell lines was evaluated by 4-hour chromium release assay as described in (20). Briefly $5\times10^3$ 51Cr-labeled target cells were incubated with CD123 specific CAR+ T cells in complete medium or 0.1% Triton X-100 (company) to determine spontaneous and maximum $^{51}$Cr release, in a V-bottomed 96-well plate. The mean percentage of specific cytolysis of triplicate wells was calculated from the release of $^{51}$Cr using a Top Count NXT (Perkin-Elmer Life and Analytic al Sciences, Inc.) as 100×(experimental release−spontaneous release)/(maximal release−spontaneous release). Data was reported as mean±SD.

Flow Cytometric Killing Assay

For T cell killing assays, target cells were labeled with PKH-26 (Sigma, cat.no PKH26PCL) according to manufacture instructions and co-culture d with CAR+ T cells at E:T ratio of 1:1 for 3 days without exogenous cytokines. 7-AAD was added prior to flow cytometric analysis to exclude dead cells, viable cells phenotyped by CD3 and PKH-26.

Cytokine Production by CAR+ T Cells

Effector cells were incubated with target cells at T cell to target ratio of 1:1 for 24 hours. Cytokine production from CAR+ T cells in response to antigen was determined using LEGENDplex™ multi analyte flow assay kit (Biolegend, cat.no 790004) according to manufacture instructions.

Mice Studies

In vivo antitumor efficacy of CAR+ T cells was assessed in NSG mice engineered mice for human interleukin-3 (IL-3), stem cell factor (SCF), and granulocyte macrophage colony-stimulating factor (GM-CSF) obtained from Jackson Laboratories. For bioluminescent xenograft models, TF1 cell line was genetically modified to express enhanced firefly luciferase (effLuc) by transducing pLVU3G effLuc-T2A-mKateS158A lentivirus construct and sorted cells for uniform mKate expression as described previously (27). On day 0 mice were intravenously (i.v.) injected with 2.5 million TF1-effLuc cells for three groups of mice (4 mice/group). On day 5, group 1 didn't receive T cells served as control whereas group 2 and 3 were injected with $10^7$ cells CD123-CD28 or CD123-41BB CAR+ T cells per mice. Tumor engraftment was confirmed by bioluminescent imaging (BLI) before T cell infusion. Two more infusions of T cells were administered on day 11 and 20 and followed by tumor burden assessment by BLI.

Determining CD123 Expression on BM Cells

To determine CD123 expression on normal BM cells, lineage positive cells were isolated using biotin conjugated lineage antibody cocktail followed by positive selection with anti-biotin microbeads using LD Column unlabeled fraction collected lineage and labeled fraction positive and labeled fraction lineage negative.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. http://www.cancer.gov/publications/patient-education/wyntk-non-hodgkin-lymphoma
2. http://www.lls.org/disease-information/myeloma
3. http://www.cancer.gov/publications/patient-education/leukemia.pdf
4. Porter et al., Chimeric antigen receptor-modified T cells in chronic lymphoid leukemia. N. Engl. J. Med. 365, 725-733 (2011).
5. Kalos, M. et al. T cells with chimeric antigen receptors have potent antitumor effects and can established memory in patients with advanced leukemia. Sci. Transl. Med. 3, 95ra73 (2011).
6. Kochenderfer, J. N. et al. Chemotherapy-refractory diffuse large B-cell lymphoma and indolent B-cell malignancies can be effectively treated with autologous T cells expressing an anti-CD19 chimeric antigen receptor. J. Clin. Oncol. 33, 540-549(2015).
7. Maude, S. L. et al. Chimeric antigen receptor T cells for sustained remissions in leukemia. N. Engl. J. Med. 371, 1507-1517 (2014)
8. Davila, M. L. et al. Efficacy and toxicity management of 19-28z CAR T cell Therapy in B cell acutelymphoblastic leukemia. Sci. Transl. Med. 6, 224ra25 (2014).
9. Hjalgrim et al., et al. Age- and sex-specific incidence of childhoodleukemia by immune immunophenotype in the Nordic countries. J Natl CancerInst 2003. 95: 1539-1544.
10. Pui et al., Mechanisms of Disease: acute lymphoblastic leukemia. N Engl J Med 2004. 350: 1535-1548.
11. Campana D. Role of minimal residual disease monitoring in adult and pediatric Acute lymphoblastic leukemia. Hematol Oncol Clin North Am. Oct. 2009; 23 (5):1083-98.
12. Hunger et al., Improved survival for children and adolescents with acute lympholymphoblastic leukemia between 1990 and 2005: a report from the children's oncology group.

13. MacMillan et al., Twenty years of unrelated donor bone marrow transplantation for pediatric acut leukemia facilitated by the National Marrow Donor Program. Biol Blood Marrow Transplant 2008; 14(9 Suppl): 16-22.
14. Hahn et al., Significant improvement in survival after allogeneic hematopoietic cell transplantation during a period of significantly increased use, older recipient age, anduse of unrelated donors. J Clin Oncol 2013; 31: 2437-2449.
15. Leung et al., High success rate of hematopoietic cell transplantation regardless of donor source in children with very high-risk leukemia. Blood 2011; 118: 223-230.
16. Pediatric acute lymphoblastic leukemia: the emerging role of peritransplantation minimal residual disease/chimerism monitoring and novel chemotherapeutic, molecular, and immune approaches aimed at preventing relapse. Biol Blood Marrow Transplant 2008; 15(1 Suppl): 62-71.
17. National Cancer Institute. SEER Stat Fact Sheets: Acute Myeloid Leukemia, 1975-2009. Available at http://seer-.cancer.gov/statfacts/html/amyl.html #incidence-mortality. Accessed Apr. 16, 2013.
18. Dohner et al. Diagnosis and management of acute myeloid leukemia in adults: recommendations from an international expert panel, on behalf of the European LeukemiaNet. Blood 2010; 115:453-74.
19. Fuad El Rassi and Martha Arellano. Update on Optimal Management of Acute Myeloid Leukemia. Clinical Medicine Insights: Oncology 2013:7 181-197.
20. Norimitsu Kadowaki and Toshio Kitawaki. Recent Advance in Antigen-Specific Immunotherapy for Acute Myeloid Leukemia. Clinical and Developmental Immunology Volume 2011, Article ID 104926, 7 pages
21. Buccisano et al., Prognostic and therapeutic implications of minimal residual disease detection in acute myeloid leukemia. Blood, 2012 volume (112), Number (2) P. 332-341
22. Joseph G. Jurcic. Immunotherapy for Acute Myeloid Leukemia. Current Oncology Reports 2005, 7:339-346.
23. Frankel et al: Activity and tolerability of SL-401, a targetedtherapy directed to the interleukin-3 receptor on cancer stem cells and tumor bulk, as a single agent in patients with advanced hematologic malignancies. J Clin Oncol 2013, 31(suppl): abstract nr 7029.
24. Roberts et al: A phase I study of anti-CD123 monoclonal antibody (CD123) CSL360 targeting leukemia stem cells (LSC) in AML. J Clin Oncol 2010, 28: abstract nr e13012.
25. Gross et al., Expression of immunoglobulin-T-cell receptor chimeric molecules as functional receptors with antibody-type specificity. Proc. Natl. Acad. Sci. USA Vol. 86, pp. 10024-10028, December 1989
26. Sadelain et al., The Basic Principles of Chimeric Antigen Receptor Design Cancer discovery. 2013.Cancer Discovery, 3(4): 388-398.
27. Zhao et al., 2009. A herceptin-Based chimeric antigen receptor with modified signaling domains leads to enhanced survival of transduced T lymphocytes and antitumor activity. Journal of Immunology 183:5563-5574.
28. Wang, et al., 2007. Optimizing adoptive polyclonal T cell immunotherapy of lymphomas, using a chimeric T cell receptor possessing CD28 and CD137 costimulatory domains. Human GeneTherapy 18:712-725.
29. Carpenito et al., 2009. Control of large, established tumor xenografts with genetically retargeted human T cells containing CD28 and CD137 domains. Proceedings of the National Academy of Sciences of the United States of America 106:3360-3365.
30. Dustin M L, Depoil D. New insights into the T cell synapse from single molecule techniques. Nat Rev Immunol 2011; 11: 672-84.
31. Bridgeman et al., Building better chimeric antigen receptors for adoptive T cell therapy Curr Gene Ther 2010; 10: 77-90.
32. Stone et al., T-cell receptor binding affinities and kinetics: impact on T-cell activity and specificity. Immunology 2009; 126:165-76.
33. Edwards L J, Evavold B D. T cell recognition of weak ligands: roles of signaling, receptor number, and affinity. Immunol Res 2011; 50:39-48.
34. Li et al., Identification of the earliest B lineage stage in mouse bone marrow. Immunity. 1996 Dec.; 5 (6):527-35.
35. Li et al., The regulated expression of B lineage associated genes during B cell differentiation in bone marrow and fetal liver. J Exp Med. 1993 Sep. 1; 178 (3):951-60
36. www.clinical trials.gov
37. Grupp et al., 2013. Chimeric antigen receptor-modified T cells for acute lymphoid leukemia. The New England Journal of Medicine 368:1509-1518.
38. Kochenderfer et al., 2012. B-cell depletion and remissions of malignancy along with cytokine-associated toxicity in a clinical trial of anti-CD19 chimeric-antigen-receptor-transduced T cells. Blood 119:2709-2720.
39. Brentjens et al., 2011. Safety and persistence of adoptively transferred autologous CD19-targeted T cells in patients with relapsed or chemotherapy refractory B-cell leukemias. Blood 118: 4817-4.
40. https://www.novartis.com/news/media-releases/novartis-personalized-cell-therapy-ctl019-receives-fda-breakthrough-therapy
41. Milone et al., Chimeric Receptors Containing CD137 Sigma 1 Transduction Domains Mediate Enhanced Survival of T Cells and Increased Antileukemic efficacy in vivo
42. Maus et al., Antibody-modified T cells: CARs take the front seat for hematologic malignancies Blood 2014 123: 2625-2635
43. Scholler J, Brady T L, Binder-Scholl G, et al. Decade-long safety and function of retroviralmodified chimeric antigen receptor T cells. Sci Transl Med. 2012; 4(132): 132ra153.
44. Biffi A, Bartolomae C C, Cesana D, et al. Lentiviral vector common integration sites in preclinical models and a clinical trial reflect a benign integration bias and not oncogenic selection. Blood. 2011; 117(20):5332-5339.
45. Zolta'n Ivics, and Zsuzsanna Izsva'k. Nonviral Gene Delivery with the Sleeping Beauty Transposon System. Human gene therapy 22:1043-1051 (September 2011)
46. Singh, H., P. R. Manuri, S. Olivares, N. Dara, M. J. Dawson, H. Huls, P. B. Hackett, D. B. Kohn, E. J. Shpall, R. E. Champlin, and L. J. Cooper. 2008. Redirecting specificity of T-cell populations for CD19 using the Sleepin Beauty system. Cancer Research 68:2961-2971.
47. Hackett, P. B., D. A. Largaespada, K. C. Switzer, and L. J. Cooper. 2013. Evaluating risks of insertional mutagenesis by DNA transposons in gene therapy. Translational Research: The Journal of Laboratory and Clinical Medicine 161:265-283.
48. Hackett, P. B., Jr., E. L. Aronovich, D. Hunter, M. Urness, J. B. Bell, S. J. Kass,L. J. Cooper, and S. McIvor. 2011. Efficacy and safety of Sleeping Beauty transposon-mediated gene transfer in preclinical animal studies. Current Gene Therapy 11:341-349.
49. Liu, G., A. M. Geurts, K. Yae, A. R. Srinivasan, S. C. Fahrenkrug, D. Largaespada, J. Takeda, K. Horie, W. K.

Olson, and P. B. Hackett. 2005 Target-site preferences of Sleeping Beauty transposons. Journal of Molecular Biology 346:161-173.

50. Boissel L, Betancur M, Wels W S, et al. Transfection with mRNA for CD19 specific chimeric antigen receptor restores NK cell mediated killing of CLL cells. Leuk Res. 2009; 33 (9):1255-1259.

51. Antigen presenting cells. Hamilos D L. Immunol Res. 1989; 8(2):98-117. Review 52. Dhodapkar M V, Steinman R M, Sapp M, Desai H, Fossella C, Krasovsky J, et al. Rapid generation of broad T-cell immunity in humans after a single injection of mature dendritic cells. J Clin Invest. 1999; 104:173-180. [PubMed: 10411546]

53. Nestle F O, Banchereau J, Hart D. Dendritic cells: on the move from bench to bedside. Nat Med. 2001; 7:761-765.

54. Almand B, Resser J R, Lindman B, Nadaf S, Clark J I, Kwon E D, et al. Clinical significance of defective dendritic cell differentiation in cancer. Clin Cancer Res. 2000; 6:1755-1766.

55. Maiti et al., 2013. Sleeping beauty system to redirect T-cell specificity for human applications. Journal of Immunotherapy 36:112-123.

56. Bagley, C. J., Woodcock, J. M., Stomski, F. C., and Lopez, A. F. (1997). The structural and functional basis of cytokine receptor activation: lessons from the common beta subunit of the granulocyte-macrophage colony-stimulating factor, interleukin-3 (IL-3), and IL-5 receptors. Blood 89, 1471-148257.

57. Miyajima, A., Mui, A. L., Ogorochi, T., and Sakamaki, K. (1993). Receptors for granulocyte-macrophage colony-stimulating factor, interleukin-3, and interleukin-5. Blood 82, 1960-1974.

58. Graf, M., Hecht, K., Reif, S., Pelka-Fleischer, R., Pfister, K., and Schmetzer, H (2004). Expression and prognostic value of hemopoietic cytokine receptors in acute myeloid leukemia (AML): implications for future therapeutical strategies. Eur. J. Haematol. 72, 89-106.

59. Testa, U., Riccioni, R., Militi, S., Coccia, E., Stellacci, E., Samoggia, P., Latagliata, R., Mariani, G., Rossini, A., Battistini, A., et al. (2002). Elevated expression of IL-3Ralpha in acute myelogenous leukemia is associated with enhanced blast proliferation, increased cellularity, and poor prognosis. Blood 100, 2980-2988.

60. Testa, U., Riccioni, R., Diverio, D., Rossini, A., Lo Coco, F., and Peschle, C. (2004). Interleukin-3 receptor in acute leukemia. Leukemia 18, 219-226.

61. Moretti S, Lanza F, Dabusti M, et al. CD123 (interleukin 3 receptor alpha chain). J Biol Regul Homeost Agents. 2001; 15:98-100.

62. Jordan C T, Upchurch D, Szilvassy S J, et al. The interleukin-3 receptor alpha chain is a unique marker for human acute myelogenous leukemia stem cells. Leukemia. 2000; 14: 1777-1784

63. Munoz L, Nomdedeu J F, Lopez O, et al. Interleukin-3 receptor alpha chain (CD123) is widely expressed in hematologic malignancies Haematologica. 2001; 86: 1261-1269.

64. Testa U, Riccioni R, Militi S, et al. Elevated expression of IL-3R alpha in acute myelogenous leukemia is associated with enhanced blast proliferation, increased cellularity, and poor prognosis. Blood. 2002; 100: 2980-2988.

65. Graf M, Hecht K, Reif S, et al. Expression and prognostic value of hemopoietic cytokine receptors in acute myeloid leukemia (AML): implications for future therapeutical strategies. Eur J Haematol. 2004; 72:89-106.

66. Testa U, Riccioni R, Diverio D, et al. Interleukin-3 receptor in acute leukemia. Leukemia. 2004; 18:219-226.

67. Black J H[1], McCubrey J A, Willingham M C, Ramage J, Hogge D E, Franke A E. Diphtheria toxin-interleukin-3 fusion protein (D T (388) IL3) prolongs disease-free survival of leukemic immunocompromised mice.

68. Feuring-Buske M, Frankel A E, Alexander R L, Gerhard B, Hogge D E. A diphtheria toxin-interleukin 3 fusion protein is cytotoxic to primitive acute myeloid leukemia progenitors but spares normal progenitors.Cancer Res. 2002 Mar. 15; 62 (6):1730-6.

69. Lapidot T, Sirard C, Vormoor J, Murdoch B, Hoang T, Caceres-Cortes J, Minden M, Paterson B, Caligiuri M A, Dick J E. A cell initiating human acute myeloid leukaemia after transplantation into SCID mice. Nature. 1994 Feb. 17; 367(6464):645-8.

70. Bhatia, M., Wang, J. C., Kapp, U., Bonnet, D., and Dick, J. E. (1997). Purification of primitive human hematopoietic cells capable of repopulating immune-deficient mice. Proc. Natl. Acad. Sci. USA 94, 5320-5325.

71. Bonnet, D., and Dick, J. E. (1997). Human acute myeloid leukemia is organize d as a hierarchy that originates from a primitive hematopoietic cell. Nat. Med. 3, 730-737

72. Florian, S., Sonneck, K., Hauswirth, A. W., Krauth, M. T., Schernthaner, G. H., Sperr, W. R., and Valent, P. (2006). Detection of molecular targets on the surface of CD34+/CD38− stem cells in various myeloid malignancies. Leuk. Lymphoma 47, 207-222

73. Jordan C T, Upchurch D, Szilvassy S J, Guzman M L, Howard D S, et al. (2000) The interleukin-3 receptor alpha chain is a unique marker for human acute myelogenous leukemia stem cells. Leukemia 14: 1777-1784.

74. Bachas et al., The role of minor subpopulations within the leukemic blast compartment of AML patients at initial diagnosis in the development of relapse. Leukemia. 2012 Jun.; 26 (6):1313-20.

75. Estey E H.Acute myeloid leukemia: 2012 update on diagnosis, risk stratification, and management. Am J Hematol. 2012 January; 87(1):89-99.

76. Roug A S, Larsen H, Nederby L, Just T, Brown G, Nyvold C G, Ommen H B, Hokland P.hMICL and CD123 in combination with a CD45/CD34/CD117 backbone—a universal marker combination for the detection of minimal residua 1 disease in acute myeloid leukemia. Br J Haematol. 2014 January; 164(2):212-22

77. M Ruella, O Shestova, S Kenderian, D Barrett, S Grupp, J Scholler,S Lacey, M Kalos, C H June, S GillAnti-CD123 chimeric antigen receptors redirected T cells for relapsed B-cell acute lymphoblstic leukemia.cytotherapy April 2014Volume 16, Issue 4, Supplement, Page S8

78. Medzhitov, R., and C. Janeway, Jr. 2000. Innate immunity. The New England Journal of Medicine 343:338-344.

79. Hoebe, K., E. Janssen, and B. Beutler. 2004. The interface between innate and adaptive immunity. Nature Immunology 5:971-974.

80. Schenten, D., and R. Medzhitov. 2011. The control of adaptive immune responses by the innate immune system. Advances in Immunology 109:87-124.

81. Vesely, M. D., M. H. Kershaw, R. D. Schreiber, and M. J. Smyth. 2011. Natural Innate and adaptive immunity to cancer. Annual Review of Immunology 29:235-271.

82. Janeway, C. A., Jr., and R. Medzhitov. 2002. Innate immune recognition. Annual review of Immunology 20:197-216.

83. Janeways immunology 5$^{th}$ edition chapter 3

84. Janeways immunology 5$^{th}$ edition chapter 5

85. Janeways immunology 5$^{th}$ edition chapter 9

86. Gideon Gross, Tova Waks, and Zelig Eshar. Expression of immunoglobulin-T-cell receptor chimeric molecules as functional receptors with antibody-type specificity. Proc. Natl. Acad. Sci. USA Vol. 86, pp. 10024-10028, December 1989 Immunology 87. Caruso et al., Tuning sensitivity of CAR to EGFR density limits recognition of normal tissue while maintaining potent antitumor activity Cancer Res; 75(17) 3505-3518

88. Liu et al., Affinity-Tuned ErbB2 or EGFR Chimeric Antigen Receptor T Cells Exhibit an Increased Therapeutic Index against Tumors in Mice. CancerResearch75 (17) 3596-3607, 201

89. Gunzer et al., A spectrum of biophysical interaction modes between T cells and different antigen-presenting cells during priming in 3-D collagen and invivo Blood, 2004 vol. 104 (9) p. 2801-2809

90. Acuto, O and Michel, F (2003). CD28-mediated co-stimulation: a quantitative support for TCR signalling. Nat Rev Immunol 3: 939-951.

91. Zhe Shao and Herbert Schwarzl. CD137 ligand, a member of the tumor necrosis factor family, regulates immune responses via reverse signal transduction. Journal of Leukocyte Biology 2 Volume 89, J 2011 p. 21-29

92. Tamzalit et al., IL-15.IL-15Rα complex shedding following trans-presentation is essential for the survival of IL-15 responding N K and T cells. Proc Natl Acad Sci USA. 2014 Jun. 10; 111(23): 8565-8570.

93. Huntington et al., IL-15 transpresentation promotes both human T-cell reconstitution and T-cell-dependent antibody responses in vivo) PNAS 2011 vol. 108 no. 15 6217-6222

94. Stonier, S. W., and K. S. Schluns. 2010. Trans-presentation: a novel mechanism regulating IL-15 delivery and responses. Immunology Letters 127:85-92.

95. Stonier, S. W., L. J. Ma, E. F. Castillo, and K. S. Schluns. 2008. Dendritic cells drive memory CD8 T-cell homeostasis via IL-15 transpresentation. Blood 112:4546-4554.

96. Xing Du, Mitchell Ho, and Ira Pastan. New Immunotoxins Targeting CD123, a Stem Cell Antigen on Acute Myeloid Leukemia Cells. J Immunother 2007; 30:607-613)

97. Hudecek M, Lupo-Stanghellini M-T, Kosasih P L, Sommermeyer D, Jensen M C, Rader C, Riddell S R: Receptor affinity and extracellular domain modifications affect tumor recognition by ROR1-specific chimeric antigen receptor T cells. Clin Cancer Res 2013, 19:3153-3164.

98. James S E, Greenberg P D, Jensen M C, Lin Y, Wang J, Till B G, Raubitschek A A, Forman S J, Press O W: Antigen sensitivity of CD22-specific chimeric TCR is modulated by target epitope distance from the cell membrane. J Immunol 2008, 180:7028-7038.

99. Miroslav Djokic, Elisabet Bjorklund, Elisabeth Blennow, Joanna Mazur, Stefan Soderhall, and Anna Porwit. Overexpression of CD123 correlates with the hyperdiploid genotype in acute lymphoblastic leukemia. Haematologica. 2009 July; 94(7): 1016-1019.

100. Hassanein N M[1], Alcancia F, Perkinson K R, Buckley P J, Lagoo A S. Distinct expression patterns of CD123 and CD34 on normal bone marrow B-cell precursors ("hematogones") and B lymphoblastic leukemia blasts. Am J Clin Pathol. 2009 October; 132(4):573-80

101. R. Bassan, et al., Improved risk classification for risk-specific therapy based on the molecular study of minimal residual disease (MRD) in adult acute lymphoblastic leukemia (ALL), Blood 113 (18) (2009) 4153-4162.

102. J. Holowiecki, et al., Status of minimal residual disease after induction predicts outcome in both standard and high-risk Ph-negative adult acute lymphoblast ic leukaemia. The Polish Adult Leukemia Group ALL 4-2002 MRD study, Br. J. Haematol. 142 (2) (2008) 227-237.

103. M. Krampera, et al., Outcome prediction by immunophenotypic minimal residual disease detection in adult T-cell acute lymphoblastic leukaemia, Br. J. Haematol. 120 (1) (2003) 74-79.

104. T. Raff, et al., Molecular relapse in adult standard-risk ALL patients detected by prospective MRD monitoring during and after maintenance treatment: data from the GMALL 06/99 and 07/03 trials, Blood 109 (3) (2007) 910-915.

105. P. Stow, et al., Clinical significance of low levels of minimal residual disease at the end of remission induction therapy in childhood acute lymphoblastic leukemia, Blood 115 (23) (2010) 4657-4663.

106. M. B. Vidriales, et al., Minimal residual disease in adolescent (older than 14 years) and adult acute lymphoblastic leukemias: early immunophenotypic evaluation has high clinical value, Blood 101 (12) (2003) 4695-4700.

107. M. B. Vidriales, et al., Minimal residual disease in adolescent (older than 14 years) and adult acute lymphoblastic leukemias: early immunophenotypic evaluation has high clinical value, Blood 101 (12) (2003) 4695-4700.

108. Ruella et al., Novel Chimeric Antigen Receptor T Cells for the Treatment of CD19-Negative Relapses Occurring after CD19-Targeted Immunotherapies. Oral and Poster Abstracts ASH 2014

109. National Cancer Institute. SEER Stat Fact Sheets: Acute Myeloid Leukemia, 1975-2009. Available at http://seer.cancer.gov/statfacts/html/amyl.html #incidence-mortality. Accessed Apr. 16, 2013.

110. Dohner H, Estey E H, Amadori S, et al. Diagnosis and management of acute myeloid leukemia in adults: recommendations from an international expert panel, on behalf of the European LeukemiaNet. Blood 2010; 115:453-74.

111. Fuad El Rassi and Martha Arellano. Update on Optimal Management of Acute Myeloid Leukemia. Clinical Medicine Insights: Oncology 2013:7 181-197

112. Norimitsu Kadowaki and Toshio Kitawaki. Recent Advance in Antigen-SpecificImmunotherapy for Acute Myeloid Leukemia. Clinical and Developmental ImmunologyVolume 2011, Article ID 104926, 7 pages 113. Buccisano et al., Prognostic and therapeutic implications of minimal residual disease detection in acute myeloid leukemia. Blood, 2012 volume (112), Number (2) P. 332-341

114. Joseph G. Jurcic. Immunotherapy for Acute Myeloid Leukemia. Current Oncology Reports 2005, 7:339-346

115. Saar Gill and Carl H.June. Going viral: chimeric antigen receptor T-cell therapy for hematological malignancies. Immunological reviews 2015 Vol. 263: 68-89

116. Jena B, Dotti G, Cooper L J (2010) Redirecting T-cell specificity by introducing a tumor-specific chimeric antigen receptor. Blood 116: 1035-1044.

117. Goverman J, Gomez S M, Segesman K D,Hunkapiller T, Laug W E, Hood L. Chimeric immunoglobulin-T cell receptor proteins form functional receptors: implications for T cell receptor complex formation and activation. Cell 1990; 60:929-939.

118. Milone M C, et al. Chimeric receptors containing CD137 signal transduction domains mediate enhanced survival of T cells and increased antileukemic efficacy invim. Mol Ther 2009; 17:1453-1464.

119. Savoldo B, et al. Brief report CD28 costimulation improves expansion and persistence of chimeric antigen receptor-modified T cells in lymphomapatients. J Clin Invest 2011; 121:1822-1826.

120. Ugo Testal, Elvira Pelosi[1] and Arthur Frankel. C D 123 is a membrane biomarker and a therapeutic target in hematologic malignancies. Biomarker Research 2014 2:4 p. 1-11

121. Jordan C T, Upchurch D, Szilvassy S J, Guzman M L, Howard D S, Pettigrew A L, Meyerrose T, Rossi R, Grimes B, Rizzieri D A, Luger S M, Phillips G L: The interleukin-3 receptor alpha is a unique marker for human acute myelogenous leukemis stem cells. Leukemia 2000, 14(10):1777-1784

122. Testa U, Riccioni R, Coccia E, Stellacci E, Samoggia P, Latagliata R, Latagliata R, Mariani G, Rossini A, Battistini A, Lo-Coco F, Peschle C: Elevated expression of IL-3Ralpha in acute myelogenous leukemia is associated with enhanced bast proliferation, increased cellularity and poor prognosis. Blood 2002, 100(8):2980-2988.

123. Hassanein N, Alcancia F, Perkinson K, Buckley P, Lagoo A: Distinct expression patterns of CD123 and CD 34 on normal bone marrow B-cell precursors ("hematogenes") and B lymphoblastic leukemia blasts. Am J Clin Pathol 2009, 132(4):573-580

124. Munoz L, Nomdedeu J F, Lopez O, Cornier M J, Bellido M, Aventin A, Brunet S, Sierra J: Interleukin-3 receptor alpha chain (CD123) is widely expressed in hematologic malignancies. Haematologica 2001, 86(12): 1261-1269.

125. Frankel A E, Konopleva M, Hogge D, Rizzieri D, Brooks C, Cirrito T, et al: Activity and tolerability of SL-401, a targeted therapy directed to the interleukin-3 receptor on cancer stem cells and tumor bulk, as a single agent in patients with advanced hematologic malignancies. J Clin Oncol 2013, 31(suppl):abstract nr 7029.

126. Roberts A W, He S, Ritchie D, Hertzberg M S, Kerridge I, et al: A phase I study of anti-CD123 monoclonal antibody (CD123) CSL360 targeting leukemia stem cells (LSC) in AML. J Clin Oncol 2010, 28: abstract nr e 13012.

127. Singh H, Manuri P R, Olivares S, Dara N, Dawson M J, et al. (2008) Redirecting specificity of T-cell populations for CD19 using the Sleeping Beauty system. Cancer Research, 68: 2961-2971

128. Singh H, Figliola M J, Dawson M J, Huls H, Olivares S, et al. (2011) Reprogramming CD19-Specific T Cells with IL-21 Signaling Can Improve Adoptive Immunotherapy of BLineage Malignancies. Cancer Res 71: 3516-3527

129. Singh H, Figliola M J, Dawson M J, Huls H, Olivares S, et al. (2011) ReprogrammingCD19-Specific T Cells with IL-21 Signaling Can Improve Adoptive Immunotherapy of BLineage Malignancies. Cancer Res 71: 3516-3527.

130. Pule M A, et al. Virus-specific T cells engineered to coexpress tumor-specific receptors: persistence and antitumor activity in individuals with neuroblastoma. *Nat Med.* 2008; 14(11):1264-1270.

131. Till B G, et al. Adoptive immunotherapy for indolent non-Hodgkin lymphoma and mantle cell lymphoma using genetically modified autologous CD20-specific T cells. *Blood.* 2008; 112 (6):2261-2271.

132. Kershaw M H, et al. A phase I study on adoptive immunotherapy using gene-modified T cells for ovarian cancer. *Clin Cancer Res.* 2006; 12 (20 pt 1):6106-6115.

133. Hinrichs C S, Spolski R, Paulos C M, Gattinoni L, Kerstann K W, Palmer D C, Klebanoff C A, Rosenberg S A, Leonard W J, Restifo N P. IL-2 and IL-21 confer opposing differentiation programs to CD8+ T cells for adoptive immunotherapy. Blood. 2008 Jun. 1; 111(11): 5326-33.

134. Mardiros et al., T cells expressing CD123-specific chimeric antigen receptors exhibit specific cytolytic effector functions and antitumor effects against human acute myeloid leukemia. Blood. 2013; 122 (18):3138-3148

135. Saar Gill, Sarah K. Tasian, Marco Ruella, Olga Shestova, Yong Li, David L. Porter, Martin Carroll, Gwenn Danet-Desnoyers, John Scholler, Stephan A. Grupp, Carl H. June and Michael Kalos Preclinical targeting of human acute myeloid leukemia and myeloablation using chimeric antigen receptor-modified T cells. 2014 123: 2343-2354

136. Huntington N D, Alves N L, Legrand N, Lim A, Strick-Marchand H, Mention J J,Plet A, Weijer K, Jacques Y, Becker P D, Guzman C,Soussan P, Kremsdorf D, Spits H, Di Santo J P. IL-15 transpresentation promotes both human T-cell reconstitution and T-cell-dependent antibody responses invivo Proc Natl Acad Sci USA. 2011 Apr. 12; 108(15):6217-22

137. Jonnalagadda M, Mardiros A, Urak R, Wang X, Hoffman L J, Bernanke A. Chang W C, Bretzlaff W, Starr R, Priceman S,Ostberg J R, Forman S J, Brown C E.Chimeric Antigen Receptors with Mutated IgG4 Fc Spacer Avoid Fc Receptor Binding and Improve T cell Persistence and Anti-Tumor Efficacy. Mol Ther. 2015 Apr.; 23(4):757-68

138. Karin C. Straathof, Martin A. Pule', Patricia Yotnda, Gianpietro Dotti, Elio F. Vanin, Malcolm K. Brenner Helen E. Heslop, David M. Spencer, and Cliona M. Rooney. An inducible caspase 9 safety switch for T-cell therapy. Blood. 2005; 105:4247-4254

139. S S Kenderian, M Ruella, O Shestova, M Klichinsky, V Aikawa, J J D Morrissette, J Scholler, D Song, D L Porter, M Carroll, C H June and S Gill CD33 specific chimeric antigen receptor t cells exhibit potent preclinical activity against human acute myeloid leukemia Leukemia advance online publication 22 May 2015

140. Han et al., Leukemia Stem Cell Marker CD123 (IL-3R alpha) Predicts Minimal Residual Disease and Relapse, Providing a Valid Target For SL-101 In Acute Myeloid Leukemia With FLT3-ITD Mutations 141. Bachas C, Schuurhuis G J, Assaraf Y G, Kwidama Z J, Kelder A, Wouters F, Snel A N, Kaspers G J, Cloos J. The role of minor subpopulations within the leukemic blast compartment of AML patients at initial diagnosis in the development of relapse. Leukemia. 2012 Jun.; 26(6): 1313-20

142. Estey E H. Am J Hematol. 2012 January; 87(1):89-99.Acute myeloid leukemia: 2012 update on diagnosis, risk stratification, and management 143. Roug A S, Larsen H, Nederby L, Just T, Brown G, Nyvold C G, Ommen H B, Hokland P.hMICL and CD123 in combination with a CD45/CD34/CD117 backbone—a universal marker combination for the detection of minimal residual disease in acute myeloid leukaemia. Br J Haematol. 2014 January; 164(2):212-22.

144. Ruella et al., Novel Chimeric Antigen Receptor T Cells for the Treatment of CD19− Negative Relapses Occurring after CD19-Targeted Immunotherapies. Oral and Poster Abstracts ASH 2014

145. Casucci et al., CD44v6-targeted T cells mediate potent antitumor effects against acute myeloid leukemia and multiple myeloma. Blood. 2013 Nov. 14; 122(20):3461-72.

146. Gill S[1], Tasian S K, Ruella M, Shestova O, Li Y, Porter D L, Carroll M, Danet-Desnovers, Scholler J, Grupp S A, June C H, Kalos M.Preclinical targeting of human acute myeloid leukemia and myeloablation using chimeric antigen receptor-modified T cells. Blood. 2014 Apr. 10; 123(15):2343-54

147. Shlush et al., Identification of pre-leukaemic haematopoietic stem cells in acuteleukaemia. Nature 506: 328-333.

148. Jordan C T, Upchurch D, Szilvassy S J, Guzman M L, Howard D S, et al. (2000) The interleukin-3 receptor alpha chain is a unique marker for human acute myelogenous leukemia stem cells. Leukemia 14: 1777-1784.

149. Testa U, Riccioni R, Militi S, Coccia E, Stellacci E, et al. (2002) Elevated expression of IL-3Ralpha in acute myelogenous leukemia is associated with enhanced blast proliferation, increased cellularity, and poor prognosis. Blood 100: 2980-2988.

150. Vergez et al., High levels of CD34+CD38low/− CD123+ blasts are predictive of an adverse outcome in acute myeloid leukemia: a Groupe Ouest-Est des Leucemies Aigues et Maladies du Sang (GOELAMS) study Haematologica. 2011 December; 96(12):1792

151. Roberts A W, He S, Ritchie D, Hertzberg M S, Kerridge I, et al. (2010) A phase I study of anti-CD123 monoclonal antibody (mAb) CSL360 targeting leukemia stem cells (LSC) in AML. J Clin Oncol 28: Abstract nr e 13012.

152. Jin L, Lee E M, Ramshaw H S, Busfeld S J, Peoppl A G, et al. (2009) Monoclonal antibody-mediated targeting of CD123, IL-3 receptor a chain, eliminates human acute myeloid leukemic stem cells. Cell Stem Cells 5: 31-42.

153. Rongvaux A, Takizawa H, Strowig T, et al. Human hemato-lymphoid system m ice: current use and future potential for medicine. Annu Rev Immunol. 2013; 31:635-674.

154. Frankel et al. Phase 1 clinical study of diphtheria toxin-interleukin 3 fusion protein in patients with acute myeloid leukemia and myelodysplasia. Leuk Lymphoma. 2008; 49 (3):543-553.

155. Taussig et al., Hematopoietic stem cells express multiple myeloid markers: implication for the origin and targeted therapy of acute myeloid leukemia 156. Ravindra Majeti, Christopher Y. Park, and Irving L. Weissman. Identification of a Hierarchy of Multipotent Hematopoietic Progenitors in Human Cord Blood Cell Stem Cell 1, 635-645, December 2007

157. Bhatia M[1], Wang J C, Kapp U, Bonnet D, Dick J E. Purification of primitive human hematopoietic cells capable of repopulating immune deficient mice. Proc Natl Acad Sci USA. 1997 May 13; 94 (10):5320-5.

158. Bernt K M[1], Armstrong S A. Kathrin M. Bernt and Scott A. Armstrong. Leukemia Stem Cells and Human Acute Lymphoblastic Leukemia. Semin Hematol 2009 January; 46 (1):33-8

159. Cox C V, Evely R S, Oakhill A, Pamphilon D H, Goulden N J, Blair A. Characterization of acute lymphoblastic leu-kemia progenitor cells. Blood. 2004; 104: 2919-25.

160. Hotfilder M, Rottgers S, Rosemann A, Jurgens H, Harbott J, Vormoor J. Immature $CD34^{+}CD19^{-}$ progenitor/stem cells in TEL/AML1-positive acute lymphoblastic leukemia are genetically and functionally normal. Blood. 2002; 100:640-6.

161. Gill et al., Preclinical targeting of human acute myeloid leukemia and myeloablation using chimeric antigen receptor-modified T cells. Blood. 2014; 123(15):2343-2354

162. Marcela V. Maus, Stephan A. Grupp, David L. Porter and Carl H. June Antibody-modified T cells: CARs take the front seat for hematologic malignancies. Blood 2014 123: 2625-2635

163. Haso W, Lee D W, Shah N N, et al. Anti-CD22-chimeric antigen receptors targeting B-cell precursor acute lymphoblastic leukemia. Blood. 2013; 121(7):1165-1174.

164. Hudecek M, Lupo-Stanghellini M T, Kosasih P L, et al. Receptor affinity and extracellular domain modifications affect tumor recognition by ROR1-specific chimeric antigen receptor T cells. Clin Cancer Res. 2013; 19(12):3153-3164.

165. Hombach A, Hombach A A, Abken H. Adoptive immunotherapy with genetically engineered T cells: modification of the IgG1 Fc 'spacer' domain in the extracellular moiety of chimeric antigen receptors avoids 'off-target' activation 166. mbach A, Heuser C, Gerken M, et al. T cell activation by recombinant FcepsilonRI gamma-chain immune receptors: an extracellular spacer domain impairs antigen-dependent T cell activation but not antigen recognition. Gene Ther. 2000; 7 (12):1067-1075.

167. Marina Y. Konopleva and Craig T. JordanLeukemia Stem Cells and Microenvironment: Biology and Therapeutic Targeting. *J Clin Oncol.* 2011 Feb. 10; 29 (5):591-9.

168. Anthony E. Boitano, Jian Wang, Russell Romeo, Laure C. Bouchez, Albert E. Parker2 Sue E. Sutton, John R. Walker, Colin A. Flaveny, Gary H. Perdew, Michael S. Denison Peter G. Schultz, Michael P. Cooke Aryl Hydrocarbon Receptor Antagonists Promote the Expansion of Human Hematopoietic Stem Cells. SCIENCE VOL 329 1345-1348.

169. Caroline Pabst, Jana Krosl, Inan Fares, Geneviéve Boucher, Réjean Ruel, Anne Marinier Sébastien Lemieux, Josée Hébert & Guy Sauvageau. Identification of small molecules that support human leukemia stem cell activity ex vivo Nature methods VOL. 11, NO. 4 2014 436-442

170. Jordan C T. Targeting myeloid leukemia stem cells. Sci. Transl Med 2010:2(31):31ps2

171. Andrews R G, Takahashi M, Segal G M, et al. The L4F3 antigen is expressed by unipotent and multipotent colony-forming cells but not by their precursors. Blood. 1986; 68:1030-1035.

172. Andrews R G, Singer J W, Bernstein I D. Human hematopoietic precursors in long-term culture: single CD34 cells that lack detectable T cell, B cell, and myeloid cell antigens produce multiple colony-forming cells when cultured with marrow stromal cells. J Exp Med. 1990; 172:355-358.

173. Andrews R G, Singer J W, Bernstein I D. Precursors of colony-forming cells in humans can be distinguished from colony-forming cells by expression of the CD33 and CD34 antigens and light scatter properties. J Exp Med. 1989; 169: 1721-1731. 4. Hu M, Krause D, Greaves M, et al. Multilineage gene expression precedes commitment in the hemopoietic system. Genes Dev. 1997; 11:774-785.

174. Hu M, Krause D, Greaves M, et al. Multilineage gene expression precedes commitment in the hemopoietic system. Genes Dev. 1997; 11:774-785.

175. Orkin S H. Priming the hematopoietic pump. Immunity. 2003; 19:633-634

176. Orkin S H. Priming the hematopoietic pump. Immunity. 2003; 19:633-634

177. Sievers E L, Appelbaum F R, Spielberger R T, et al. Selective ablation of acute myeloid leukemia using antibody-targeted chemotherapy: a phase I study of an anti-CD33 calicheamicin immunoconjugate. Blood. 1999; 93:3678-3684.

178. Jurcic J G, Larson S M, Sgouros G, et al. Targeted alpha particle immunotherapy for myeloid leukemia. Blood. 2002; 100:1233-1239.

179. Feuring-Buske M, Frankel A E, Alexander R L, Gerhard B, Hogge D E. A diphtheria toxin-interleukin 3 fusion protein is cytotoxic to primitive acute myeloid leukemia progenitors but spares normal progenitors. Cancer Res. 2002; 62:1730-1736.

180. Bae J, Martinson J A, Klingemann H G. Heteroclitic CD33 peptide with enhanced anti-acute myeloid leukemic immunogenicity. Clin Cancer Res. 2004; 10:7043-7052.

181. Griffin J D, Linch D, Sabbath K, Larcom P, Schlossman S F. A monoclonal antibody reactive with normal and leukemic human myeloid progenitor cells. Leuk Res. 1984; 8 (4):521-34.

182. Sievers E L, Larson R A, Stadtmauer E A, et al. Efficacy and safety of gemtuzumab ozogamicin in patients with CD33-positive acute myeloid leukemia in first relapse. J Clin Oncol. 2001; 19:3244-3254.

183. Kell W J, Burnett A K, Chopra R, et al. A feasibility study of simultane ous administration of gemtuzumab ozogamicin with intensive chemotherapy in induction and consolidation in younger patients with acute myeloid leukemia. Blood. 2003; 102: 4277-4283

184. Linenberger M L, Hong T, Flowers D, et al. Multidrug-resistance phenotype and clinical responses to gemtuzumab ozogamicin. Blood. 2001; 98:988-994

185. Majeti R, Park C Y, Weissman I L. Identification of a Hierarchyof Multipote nt Hematopoietic Progenitors in Human Cord Blood. Cell Stem Cell. 2007 Dec. 13; 1 (6):635-45.

186. Gill S, Tasian S K, Ruella M, Shestova O, Li Y, Porter D L, Carroll M, Danet-Desnoyers G, Scholler J, Grupp S A, June C H, Kalos M. Preclinical targeting of human acute myeloid leukemia and myeloablation using chimeric antigen receptor-modified T cells. Blood. 2014 Apr. 10; 123 (15):2343-54.

187. Taussig D C[1], Pearce D J, Simpson C, Rohatiner A Z, Lister T A, Kelly G, Luongo J L, Danet-Desnoyers G A, Bonnet D.Hematopoietic stem cells express multiple myeloid markers: implications for the origin and targeted therapy of acute myeloid leukemia. Blood. 2005 Dec. 15; 106(13):4086-92

188. Taussig D C, Vargaftig J, Miraki-Moud F, et al: Leukemia-initiating cells from some acute myeloid leukemia patients with mutated nucleophosmin reside in the CD34 (−) fraction. Blood 115:1976-1984, 2010

189. Taussig D C, Miraki-Moud F, Anjos-Afonso F, et al: Anti-CD38 antibody-mediated clearance of human repopulating cells masks the heterogeneity of leukemia-initiating cells. Blood 112:568-575, 2008

190. Leukemia-initiating cells from some acute myeloid leukemia patients with mutated nucleophosmin re-side in the CD34 (−) fraction. Blood 115:1976-1984 2010

191. Anti-CD38 antibody-mediated clearance of human repopulating cells masks the heterogeneity of leukemia-initiating cells. Blood 112:568-575, 2008

192. Pulsipher M A, Bader P, Klingebiel T, Cooper L J. Allogeneic transplantation for 193. Eggermont L J, Paulis L E, Tel J, Figdor C G. Towards efficient cancer immunotherapy: advances in developing artificial antigen-presenting cells. Trends in Biotechnology. 2015; 32(9):456-65.

194. Rosenberg S A, Restifo N P. Adoptive cell transfer as personalized immunotherapy for human cancer. Science. 2015; 348(6230):62-8.

195. Wargo J A, Cooper Z A, Flaherty K T. Universes Collide: Combining Immunotherapy with Targeted Therapy for Cancer. Cancer Discovery. 2014; 4(12): 1377-86.

196. Eshhar Z, Waks T, Gross G, Schindler D G. Specific activation and targeting of cytotoxic lymphocytes through chimeric single chains consisting of antibody-binding domains and the gamma or zeta subunits of the immunoglobulin and T-cell receptors. Proc Natl Acad Sci USA. 1993; 90(2):720-4. Epub 1993/01/15.

197. Kowolik C M, Topp M S, Gonzalez S, Pfeiffer T, Olivares S, Gonzalez N, et al. CD28 costimulation provided through a CD19-specific chimeric antigen receptor enhances in vivo persistence and antitumor efficacy of adoptively transferred T cells. Cancer Res. 2006; 66(22): 10995-1004. Epub 2006/11/17.

198. Zhang H, Snyder K M, Suhoski M M, Maus M V, Kapoor V, June C H, et al. 4-1BB is superior to CD28 costimulation for generating CD8+ cytotoxic lymphocytes for adoptive immunotherapy. J Immunol. 2007; 179(7):4910-8. Epub 2007/09/20. 179/7/4910 [pii].

199. Zhong X S, Matsushita M, Plotkin J, Riviere I, Sadelain M. Chimeric antigen receptors combining 4-1BB and CD28 signaling domains augment PI3kinase/AKT/Bcl-XL activation and CD8+ T cell-mediated tumor eradication. Mol Ther. 2010; 18(2):413-20. Epub 2009/09/24.

200. Kochenderfer J N, Wilson W H, Janik J E, Dudley M E, Stetler-Stevenson M, Feldman S A, et al. Eradication of B-lineage cells and regression of lymphoma in a patient treated with autologous T cells genetically engineered to recognize CD19. Blood. 2010; 116(20):4099-102. Epub 2010/07/30.

201. Porter D L, Hwang W-T, Frey N V, Lacey S F, Shaw P A, Loren A W, et al. Chimeric antigen receptor T cells persist and induce sustained remissions in relapsed refractory chronic lymphocytic leukemia. Science Translational Medicine. 2015; 7(303):303ra139-303ra139.

202. Caruso H G T H, Zhang L, Maiti S, Dai J, Do K, Singh H, Huls H, Lee D A, Champlin R E, Heimberger A B, Cooper L J N. Redirecting T cell specificity to EGFR using mRNA to self-limit expresssion of chimeric antigen receptor. Oncoimmunology. 2015; Submitted.

What is claimed is:

1. A chimeric antigen receptor (CAR) polypeptide comprising, from N- to C-terminus, an antigen binding domain; a hinge domain; a transmembrane domain and an intracellular signaling domain, wherein the CAR polypeptide binds to a target antigen and wherein the antigen binding domain comprises HCDR sequences from a first antibody that binds to the target antigen and LCDR sequences from a second antibody that binds to the target antigen, wherein the target antigen is CD123, wherein the antigen binding domain comprises:

(i) a heavy chain variable region (VH) having a VHCDR1 amino acid sequence comprising SEQ ID NO: 33, a VHCDR2 amino acid sequence comprising SEQ ID NO: 34, and a VHCDR3 amino acid sequence comprising SEQ ID NO: 35; and a light chain variable region (VL) having a VLCDR1 amino acid sequence comprising SEQ ID NO: 24, a VLCDR2 amino acid sequence comprising SEQ ID NO: 25, and a VLCDR3 amino acid sequence comprising SEQ ID NO: 26;

(ii) a heavy chain variable region (VH) having a VHCDR1 amino acid sequence comprising SEQ ID NO: 27, a VHCDR2 amino acid sequence comprising SEQ ID NO: 28, and a VHCDR3 amino acid sequence comprising SEQ ID NO: 29; and a light chain variable region (VL) having a VLCDR1 amino acid sequence comprising SEQ ID NO: 24, a VLCDR2 amino acid sequence comprising SEQ ID NO: 25, and a VLCDR3 amino acid sequence comprising SEQ ID NO: 26;

(iii) a heavy chain variable region (VH) having a VHCDR1 amino acid sequence comprising SEQ ID NO: 39, a VHCDR2 amino acid sequence comprising SEQ ID NO: 40, and a VHCDR3 amino acid sequence comprising SEQ ID NO: 41; and a light chain variable region (VL) having a VLCDR1 amino acid sequence comprising SEQ ID NO: 36, a VLCDR2 amino acid sequence comprising SEQ ID NO: 37, and a VLCDR3 amino acid sequence comprising SEQ ID NO: 38; or (iv) a heavy chain variable region (VH) having a VHCDR1 amino acid sequence comprising SEQ ID NO: 21, a VHCDR2 amino acid sequence comprising SEQ ID NO: 22, and a VHCDR3 amino acid sequence comprising SEQ ID NO: 23; and a light chain variable region (VL) having a VLCDR1 amino acid sequence comprising SEQ ID NO: 30, a VLCDR2 amino acid sequence comprising SEQ ID NO: 31, and a VLCDR3 amino acid sequence comprising SEQ ID NO: 32.

2. The polypeptide of claim 1, wherein the hinge domain is a CD8a hinge having a sequence comprising KPTTTPA-PRPPTPAPTIASQPLSLRPEACRPAAGGAVHTRGLD (SEQ ID NO: 12) or an IgG4 hinge having a sequence comprising ESKYGPPCPPCPAPE-FLGGPSVFLFPPKPKDTLMISRTPE-VTCVVVDVSQEDPEVQFNWY VDGVEVHNAKTKPREEQFN-STYRVVSVLTVLHQDWLNGKEYKCKVSNKGLPSS IEKTIS KAKGQPREPQVYTLPPSQEEMTKNQVSLT-CLVKGFYPSDIAVEWESNGQPENNYKTTPP VLDSDGSFFLY-SRLTVDKSRWQEGNVFSCSVMHEALHN-HYTQKSLSLSLGKM (SEQ ID NO: 13).

3. The polypeptide of claim 1, wherein the transmembrane domain is a CD8a transmembrane domain having a sequence comprising FACDIYI-WAPLAGTCGVLLLSLVITLYCNHRN (SEQ ID NO: 14) or a CD28 transmembrane domain having a sequence comprising FWVLVVVGGVLACYSLLVTVAFIIFWV (SEQ ID NO: 15).

4. The polypeptide of claim 1, wherein the intracellular signaling domain comprises a CD3z intracellular signaling domain having a sequence comprising RVKFSRSADAPA-YQQGQNQLYNELNLGRREEYDVLDKRR-GRDPEMGGKPRRKNPQEG LYNELQKDKMAEAYSEI-GMKGERRRGKGHDGLYQGLSTATKDTYDALHMQ ALPPR (SEQ ID NO: 16).

5. A nucleic acid molecule encoding a CAR polypeptide in accordance with claim 1.

6. The nucleic acid molecule of claim 5, wherein the sequence encoding the CAR polypeptide is operatively linked to expression control sequences.

7. An isolated immune effector cell comprising a CAR polypeptide in accordance with claim 1.

8. The cell of claim 7, wherein the nucleic acid is integrated into the genome of the cell.

9. The cell of claim 7, wherein the cell is a T-cell.

10. The cell of claim 7, wherein the cell is a human cell.

11. A pharmaceutical composition comprising a population of cells in accordance with claim 10 in a pharmaceutically acceptable carrier.

12. A method of treating a subject comprising administering an anti-tumor effective amount of chimeric antigen receptor (CAR) T-cells that expresses a CAR polypeptide according to claim 1.

13. The method of claim 12, wherein the CAR-T cells are allogeneic cells.

14. The method of claim 12, wherein the CAR-T cells are autologous cells.

15. The method of claim 12, wherein the CAR-T cells are HLA matched to the subject.

16. The method of claim 12, wherein the subject has a cancer.

* * * * *

SEQUENCE LISTING

```
<160> NUMBER OF SEQ ID NOS: 53

<210> SEQ ID NO 1
<211> LENGTH: 115
```

```
<212> TYPE: PRT
<213> ORGANISM: Artificial sequence
<220> FEATURE:
<223> OTHER INFORMATION: Synthetic amino acid

<400> SEQUENCE: 1

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
            100                 105                 110

Val Ser Ser
        115


<210> SEQ ID NO 2
<211> LENGTH: 107
<212> TYPE: PRT
<213> ORGANISM: Artificial sequence
<220> FEATURE:
<223> OTHER INFORMATION: Synthetic amino acid

<400> SEQUENCE: 2

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Lys
            100                 105


<210> SEQ ID NO 3
<211> LENGTH: 118
<212> TYPE: PRT
<213> ORGANISM: Artificial sequence
<220> FEATURE:
<223> OTHER INFORMATION: Synthetic amino acid

<400> SEQUENCE: 3

Gln Val Gln Leu Gln Gln Pro Gly Ala Glu Leu Val Lys Pro Gly Ala
1               5                   10                  15

Pro Val Lys Leu Ser Cys Lys Ala Ser Gly Tyr Thr Phe Thr Asn Tyr
            20                  25                  30

Trp Met Asn Trp Ile Lys Gln Arg Pro Gly Arg Gly Leu Glu Trp Ile
```

```
        35                  40                  45

Gly Arg Ile Asp Pro Ser Asp Ser Glu Ser His Tyr Asn Gln Lys Phe
    50                  55                  60

Lys Asp Lys Ala Thr Leu Thr Val Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Tyr Asp Tyr Asp Asp Thr Met Asp Tyr Trp Gly Gln Gly Thr
            100                 105                 110

Ser Val Thr Val Ser Ser
        115


<210> SEQ ID NO 4
<211> LENGTH: 112
<212> TYPE: PRT
<213> ORGANISM: Artificial sequence
<220> FEATURE:
<223> OTHER INFORMATION: Synthetic amino acid

<400> SEQUENCE: 4

Asp Ile Val Met Thr Gln Ala Ala Pro Ser Val Pro Val Thr Pro Gly
1               5                   10                  15

Glu Ser Val Ser Ile Ser Cys Arg Ser Asn Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110


<210> SEQ ID NO 5
<211> LENGTH: 118
<212> TYPE: PRT
<213> ORGANISM: Artificial sequence
<220> FEATURE:
<223> OTHER INFORMATION: Synthetic amino acid

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Thr Ser Gly Tyr Val Phe Thr Asn Tyr
            20                  25                  30

Gly Met Asn Trp Val Lys Gln Ala Pro Gly Lys Gly Phe Lys Trp Met
        35                  40                  45

Gly Trp Met Asn Thr Asn Thr Gly Glu Pro Thr Ser Leu Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Asp Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110
```

```
Ser Val Thr Val Ser Ser
        115


<210> SEQ ID NO 6
<211> LENGTH: 111
<212> TYPE: PRT
<213> ORGANISM: Artificial sequence
<220> FEATURE:
<223> OTHER INFORMATION: Synthetic amino acid

<400> SEQUENCE: 6

Asp Ile Val Leu Thr Gln Ser Pro Ala Ser Leu Ala Val Ser Pro Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Asp Ser Arg Thr Asp Phe Thr Leu Thr Ile Asn
65                  70                  75                  80

Pro Val Glu Ala Asp Asp Val Ala Thr Tyr Tyr Cys Gln Gln Ser Lys
                85                  90                  95

Glu Asp Pro Pro Thr Phe Gly Ala Gly Thr Lys Leu Glu Leu Lys
            100                 105                 110


<210> SEQ ID NO 7
<211> LENGTH: 118
<212> TYPE: PRT
<213> ORGANISM: Artificial sequence
<220> FEATURE:
<223> OTHER INFORMATION: Synthetic amino acid

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser
        115


<210> SEQ ID NO 8
<211> LENGTH: 111
<212> TYPE: PRT
<213> ORGANISM: Artificial sequence
<220> FEATURE:
<223> OTHER INFORMATION: Synthetic amino acid

<400> SEQUENCE: 8

Asp Ile Val Leu Thr Gln Ser Pro Ala Ser Leu Ala Val Ser Leu Gly
```

```
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys
            100                 105                 110


<210> SEQ ID NO 9
<211> LENGTH: 18
<212> TYPE: DNA
<213> ORGANISM: Artificial sequence
<220> FEATURE:
<223> OTHER INFORMATION: Synthetic primer

<400> SEQUENCE: 9

cagcgacggc agcttctt                                                    18


<210> SEQ ID NO 10
<211> LENGTH: 17
<212> TYPE: DNA
<213> ORGANISM: Artificial sequence
<220> FEATURE:
<223> OTHER INFORMATION: Synthetic primer

<400> SEQUENCE: 10

tgcatcacgg agctaaa                                                     17


<210> SEQ ID NO 11
<211> LENGTH: 15
<212> TYPE: DNA
<213> ORGANISM: Artificial sequence
<220> FEATURE:
<223> OTHER INFORMATION: Synthetic primer

<400> SEQUENCE: 11

agagccggtg gcagg                                                       15


<210> SEQ ID NO 12
<211> LENGTH: 43
<212> TYPE: PRT
<213> ORGANISM: Artificial sequence
<220> FEATURE:
<223> OTHER INFORMATION: Synthetic amino acid

<400> SEQUENCE: 12

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp
        35                  40


<210> SEQ ID NO 13
<211> LENGTH: 230
<212> TYPE: PRT
```

<213> ORGANISM: Artificial sequence
<220> FEATURE:
<223> OTHER INFORMATION: Synthetic amino acid

<400> SEQUENCE: 13

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230
```

<210> SEQ ID NO 14
<211> LENGTH: 32
<212> TYPE: PRT
<213> ORGANISM: Artificial sequence
<220> FEATURE:
<223> OTHER INFORMATION: Synthetic amino acid

<400> SEQUENCE: 14

```
Phe Ala Cys Asp Ile Tyr Ile Trp Ala Pro Leu Ala Gly Thr Cys Gly
1               5                   10                  15

Val Leu Leu Leu Ser Leu Val Ile Thr Leu Tyr Cys Asn His Arg Asn
            20                  25                  30
```

<210> SEQ ID NO 15
<211> LENGTH: 27
<212> TYPE: PRT
<213> ORGANISM: Artificial sequence
<220> FEATURE:
<223> OTHER INFORMATION: Synthetic amino acid

<400> SEQUENCE: 15

```
Phe Trp Val Leu Val Val Val Gly Gly Val Leu Ala Cys Tyr Ser Leu
1               5                   10                  15
```

```
Leu Val Thr Val Ala Phe Ile Ile Phe Trp Val
            20                  25
```

```
<210> SEQ ID NO 16
<211> LENGTH: 112
<212> TYPE: PRT
<213> ORGANISM: Artificial sequence
<220> FEATURE:
<223> OTHER INFORMATION: Synthetic amino acid

<400> SEQUENCE: 16

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 17
<211> LENGTH: 493
<212> TYPE: PRT
<213> ORGANISM: Artificial sequence
<220> FEATURE:
<223> OTHER INFORMATION: Synthetic amino acid

<400> SEQUENCE: 17

Met Leu Leu Leu Val Thr Ser Leu Leu Leu Cys Glu Leu Pro His Pro
1               5                   10                  15

Ala Phe Leu Leu Ile Pro Asp Val Gln Ile Thr Gln Ser Pro Ser Tyr
            20                  25                  30

Leu Ala Ala Ser Pro Gly Glu Thr Ile Thr Ile Asn Cys Arg Ala Ser
        35                  40                  45

Lys Ser Ile Ser Lys Asp Leu Ala Trp Tyr Gln Glu Lys Pro Gly Lys
    50                  55                  60

Thr Asn Lys Leu Leu Ile Tyr Ser Gly Ser Thr Leu Gln Ser Gly Ile
65                  70                  75                  80

Pro Ser Arg Phe Ser Gly Ser Gly Ser Gly Thr Asp Phe Thr Leu Thr
                85                  90                  95

Ile Ser Ser Leu Glu Pro Glu Asp Phe Ala Met Tyr Tyr Cys Gln Gln
            100                 105                 110

His Asn Lys Tyr Pro Tyr Thr Phe Gly Gly Gly Thr Lys Leu Glu Ile
        115                 120                 125

Lys Gly Ser Thr Ser Gly Ser Gly Lys Pro Gly Ser Gly Glu Gly Ser
    130                 135                 140

Thr Lys Gly Gln Ile Gln Leu Val Gln Ser Gly Pro Glu Leu Lys Lys
145                 150                 155                 160

Pro Gly Glu Thr Val Lys Ile Ser Cys Lys Thr Ser Gly Tyr Val Phe
                165                 170                 175

Thr Asn Tyr Gly Met Asn Trp Val Lys Gln Ala Pro Gly Lys Gly Phe
```

```
            180                 185                 190

Lys Trp Met Gly Trp Met Asn Thr Asn Thr Gly Glu Pro Thr Ser Leu
        195                 200                 205

Glu Asp Phe Lys Gly Arg Phe Ala Phe Ser Leu Glu Thr Ser Ala Ser
    210                 215                 220

Thr Ala Tyr Leu Gln Ile Asn Asn Leu Lys Asn Asp Asp Thr Ala Thr
225                 230                 235                 240

Tyr Phe Cys Ala Arg Ser Gly Gly Tyr Asp Pro Met Asp Tyr Trp Gly
                245                 250                 255

Gln Gly Thr Ser Val Thr Val Ser Ser Lys Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Asn His Arg Asn Arg Ser Lys Arg Ser Arg Gly Gly His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 18
<211> LENGTH: 497
<212> TYPE: PRT
<213> ORGANISM: Artificial sequence
<220> FEATURE:
<223> OTHER INFORMATION: Synthetic amino acid

<400> SEQUENCE: 18

Met Leu Leu Leu Val Thr Ser Leu Leu Leu Cys Glu Leu Pro His Pro
1               5                   10                  15

Ala Phe Leu Leu Ile Pro Asp Ile Val Leu Thr Gln Ser Pro Ala Ser
            20                  25                  30

Leu Ala Val Ser Pro Gly Gln Arg Ala Thr Ile Ser Cys Arg Ala Ser
        35                  40                  45

Glu Ser Val Asp Asn Tyr Gly Asn Thr Phe Met His Trp Tyr Gln Gln
```

```
    50                  55                  60

Lys Pro Gly Gln Pro Pro Lys Leu Leu Ile Tyr Arg Ala Ser Asn Leu
65                  70                  75                  80

Glu Ser Gly Ile Pro Ala Arg Phe Ser Gly Ser Asp Ser Arg Thr Asp
                85                  90                  95

Phe Thr Leu Thr Ile Asn Pro Val Glu Ala Asp Asp Val Ala Thr Tyr
            100                 105                 110

Tyr Cys Gln Gln Ser Lys Glu Asp Pro Pro Thr Phe Gly Ala Gly Thr
        115                 120                 125

Lys Leu Glu Leu Lys Gly Ser Thr Ser Gly Ser Gly Lys Pro Gly Ser
    130                 135                 140

Gly Glu Gly Ser Thr Lys Gly Gln Ile Gln Leu Val Gln Ser Gly Pro
145                 150                 155                 160

Glu Leu Lys Lys Pro Gly Glu Thr Val Lys Ile Ser Cys Lys Thr Ser
                165                 170                 175

Gly Tyr Val Phe Thr Asn Tyr Gly Met Asn Trp Val Lys Gln Ala Pro
            180                 185                 190

Gly Lys Gly Phe Lys Trp Met Gly Trp Met Asn Thr Asn Thr Gly Glu
        195                 200                 205

Pro Thr Ser Leu Glu Asp Phe Lys Gly Arg Phe Ala Phe Ser Leu Glu
    210                 215                 220

Thr Ser Ala Ser Thr Ala Tyr Leu Gln Ile Asn Asn Leu Lys Asn Asp
225                 230                 235                 240

Asp Thr Ala Thr Tyr Phe Cys Ala Arg Ser Gly Gly Tyr Asp Pro Met
                245                 250                 255

Asp Tyr Trp Gly Gln Gly Thr Ser Val Thr Val Ser Ser Lys Pro Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Asn His Arg Asn Arg Ser Lys Arg Ser Arg Gly Gly
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480
```

```
Ala Thr Lys Asp Thr Tyr Asp Ala Leu His Met Gln Ala Leu Pro Pro
                485                 490                 495

Arg


<210> SEQ ID NO 19
<211> LENGTH: 498
<212> TYPE: PRT
<213> ORGANISM: Artificial sequence
<220> FEATURE:
<223> OTHER INFORMATION: Synthetic amino acid

<400> SEQUENCE: 19

Met Leu Leu Leu Val Thr Ser Leu Leu Leu Cys Glu Leu Pro His Pro
1               5                   10                  15

Ala Phe Leu Leu Ile Pro Asp Ile Val Met Thr Gln Ala Ala Pro Ser
            20                  25                  30

Val Pro Val Thr Pro Gly Glu Ser Val Ser Ile Ser Cys Arg Ser Asn
        35                  40                  45

Lys Ser Leu Leu His Ser Asn Gly Asn Thr Tyr Leu Tyr Trp Phe Leu
    50                  55                  60

Gln Arg Pro Gly Gln Ser Pro Gln Leu Leu Ile Tyr Arg Met Ser Asn
65                  70                  75                  80

Leu Ala Ser Gly Val Pro Asp Arg Phe Ser Gly Ser Gly Ser Gly Thr
                85                  90                  95

Ala Phe Thr Leu Arg Ile Ser Arg Val Glu Ala Glu Asp Val Gly Val
            100                 105                 110

Tyr Tyr Cys Met Gln His Leu Glu Tyr Pro Tyr Thr Phe Gly Gly Gly
        115                 120                 125

Thr Lys Leu Glu Ile Lys Gly Ser Thr Ser Gly Ser Gly Lys Pro Gly
    130                 135                 140

Ser Gly Glu Gly Ser Thr Lys Gly Gln Val Gln Leu Gln Gln Pro Gly
145                 150                 155                 160

Ala Glu Leu Val Lys Pro Gly Ala Pro Val Lys Leu Ser Cys Lys Ala
                165                 170                 175

Ser Gly Tyr Thr Phe Thr Asn Tyr Trp Met Asn Trp Ile Lys Gln Arg
            180                 185                 190

Pro Gly Arg Gly Leu Glu Trp Ile Gly Arg Ile Asp Pro Ser Asp Ser
        195                 200                 205

Glu Ser His Tyr Asn Gln Lys Phe Lys Asp Lys Ala Thr Leu Thr Val
    210                 215                 220

Asp Lys Ser Ser Asn Thr Ala Tyr Ile Gln Leu Ser Ser Leu Thr Ser
225                 230                 235                 240

Glu Asp Ser Ala Val Tyr Tyr Cys Ala Arg Tyr Asp Tyr Asp Asp Thr
                245                 250                 255

Met Asp Tyr Trp Gly Gln Gly Thr Ser Val Thr Val Ser Ser Lys Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335
```

```
Ile Thr Leu Tyr Cys Asn His Arg Asn Arg Ser Lys Arg Ser Arg Gly
            340                 345                 350

Gly His Ser Asp Tyr Met Asn Met Thr Pro Arg Arg Pro Gly Pro Thr
        355                 360                 365

Arg Lys His Tyr Gln Pro Tyr Ala Pro Pro Arg Asp Phe Ala Ala Tyr
    370                 375                 380

Arg Ser Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg


<210> SEQ ID NO 20
<211> LENGTH: 497
<212> TYPE: PRT
<213> ORGANISM: Artificial sequence
<220> FEATURE:
<223> OTHER INFORMATION: Synthetic amino acid

<400> SEQUENCE: 20

Met Leu Leu Leu Val Thr Ser Leu Leu Leu Cys Glu Leu Pro His Pro
1               5                   10                  15

Ala Phe Leu Leu Ile Pro Asp Ile Val Leu Thr Gln Ser Pro Ala Ser
            20                  25                  30

Leu Ala Val Ser Leu Gly Gln Arg Ala Thr Ile Ser Cys Arg Ala Ser
        35                  40                  45

Glu Ser Val Asp Asn Tyr Gly Asn Thr Phe Met His Trp Tyr Gln Gln
    50                  55                  60

Lys Pro Gly Gln Pro Pro Lys Leu Leu Ile Tyr Arg Ala Ser Asn Leu
65                  70                  75                  80

Glu Ser Gly Ile Pro Ala Arg Phe Ser Gly Ser Gly Ser Arg Thr Asp
                85                  90                  95

Phe Thr Leu Thr Ile Asn Pro Val Glu Ala Asp Asp Val Ala Thr Tyr
            100                 105                 110

Tyr Cys Gln Gln Ser Asn Glu Asp Pro Pro Thr Phe Gly Ala Gly Thr
        115                 120                 125

Lys Leu Glu Leu Lys Gly Ser Thr Ser Gly Ser Gly Lys Pro Gly Ser
    130                 135                 140

Gly Glu Gly Ser Thr Lys Gly Gln Ile Gln Leu Val Gln Ser Gly Pro
145                 150                 155                 160

Glu Leu Lys Lys Pro Gly Glu Thr Val Lys Ile Ser Cys Lys Ala Ser
                165                 170                 175

Gly Tyr Ile Phe Thr Asn Tyr Gly Met Asn Trp Val Lys Gln Ala Pro
            180                 185                 190

Gly Lys Ser Phe Lys Trp Met Gly Trp Ile Asn Thr Tyr Thr Gly Glu
```

```
        195                 200                 205

Ser Thr Tyr Ser Ala Asp Phe Lys Gly Arg Phe Ala Phe Ser Leu Glu
    210                 215                 220

Thr Ser Ala Ser Thr Ala Tyr Leu His Ile Asn Asp Leu Lys Asn Glu
225                 230                 235                 240

Asp Thr Ala Thr Tyr Phe Cys Ala Arg Ser Gly Gly Tyr Asp Pro Met
                245                 250                 255

Asp Tyr Trp Gly Gln Gly Thr Ser Val Thr Val Ser Ser Lys Pro Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Asn His Arg Asn Arg Ser Lys Arg Ser Arg Gly Gly
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg


<210> SEQ ID NO 21
<211> LENGTH: 5
<212> TYPE: PRT
<213> ORGANISM: Artificial sequence
<220> FEATURE:
<223> OTHER INFORMATION: Synthetic amino acid

<400> SEQUENCE: 21

Ser Tyr Trp Met Asn
1               5


<210> SEQ ID NO 22
<211> LENGTH: 17
<212> TYPE: PRT
<213> ORGANISM: Artificial sequence
<220> FEATURE:
<223> OTHER INFORMATION: Synthetic amino acid
```

<400> SEQUENCE: 22

Arg Ile Asp Pro Tyr Asp Ser Glu Thr His Tyr Asn Gln Lys Phe Lys
1 5 10 15

Asp

<210> SEQ ID NO 23
<211> LENGTH: 6
<212> TYPE: PRT
<213> ORGANISM: Artificial sequence
<220> FEATURE:
<223> OTHER INFORMATION: Synthetic amino acid

<400> SEQUENCE: 23

Gly Asn Trp Asp Asp Tyr
1 5

<210> SEQ ID NO 24
<211> LENGTH: 11
<212> TYPE: PRT
<213> ORGANISM: Artificial sequence
<220> FEATURE:
<223> OTHER INFORMATION: Synthetic amino acid

<400> SEQUENCE: 24

Arg Ala Ser Lys Ser Ile Ser Lys Asp Leu Ala
1 5 10

<210> SEQ ID NO 25
<211> LENGTH: 7
<212> TYPE: PRT
<213> ORGANISM: Artificial sequence
<220> FEATURE:
<223> OTHER INFORMATION: Synthetic amino acid

<400> SEQUENCE: 25

Ser Gly Ser Thr Leu Gln Ser
1 5

<210> SEQ ID NO 26
<211> LENGTH: 9
<212> TYPE: PRT
<213> ORGANISM: Artificial sequence
<220> FEATURE:
<223> OTHER INFORMATION: Synthetic amino acid

<400> SEQUENCE: 26

Gln Gln His Asn Lys Tyr Pro Tyr Thr
1 5

<210> SEQ ID NO 27
<211> LENGTH: 5
<212> TYPE: PRT
<213> ORGANISM: Artificial sequence
<220> FEATURE:
<223> OTHER INFORMATION: Synthetic amino acid

<400> SEQUENCE: 27

Asn Tyr Trp Met Asn
1 5

<210> SEQ ID NO 28
<211> LENGTH: 17
<212> TYPE: PRT
<213> ORGANISM: Artificial sequence
<220> FEATURE:
<223> OTHER INFORMATION: Synthetic amino acid

<400> SEQUENCE: 28

```
Arg Ile Asp Pro Ser Asp Ser Glu Ser His Tyr Asn Gln Lys Phe Lys
1               5                   10                  15

Asp
```

<210> SEQ ID NO 29
<211> LENGTH: 9
<212> TYPE: PRT
<213> ORGANISM: Artificial sequence
<220> FEATURE:
<223> OTHER INFORMATION: Synthetic amino acid

<400> SEQUENCE: 29

```
Tyr Asp Tyr Asp Asp Thr Met Asp Tyr
1               5
```

<210> SEQ ID NO 30
<211> LENGTH: 16
<212> TYPE: PRT
<213> ORGANISM: Artificial sequence
<220> FEATURE:
<223> OTHER INFORMATION: Synthetic amino acid

<400> SEQUENCE: 30

```
Arg Ser Asn Lys Ser Leu Leu His Ser Asn Gly Asn Thr Tyr Leu Tyr
1               5                   10                  15
```

<210> SEQ ID NO 31
<211> LENGTH: 8
<212> TYPE: PRT
<213> ORGANISM: Artificial sequence
<220> FEATURE:
<223> OTHER INFORMATION: Synthetic amino acid

<400> SEQUENCE: 31

```
Arg Met Ser Asn Leu Ala Ser Gly
1               5
```

<210> SEQ ID NO 32
<211> LENGTH: 9
<212> TYPE: PRT
<213> ORGANISM: Artificial sequence
<220> FEATURE:
<223> OTHER INFORMATION: Synthetic amino acid

<400> SEQUENCE: 32

```
Met Gln His Leu Glu Tyr Pro Tyr Thr
1               5
```

<210> SEQ ID NO 33
<211> LENGTH: 5
<212> TYPE: PRT
<213> ORGANISM: Artificial sequence
<220> FEATURE:
<223> OTHER INFORMATION: Synthetic amino acid

<400> SEQUENCE: 33

```
Asn Tyr Gly Met Asn
1               5
```

<210> SEQ ID NO 34
<211> LENGTH: 17
<212> TYPE: PRT
<213> ORGANISM: Artificial sequence
<220> FEATURE:

<223> OTHER INFORMATION: Synthetic amino acid

<400> SEQUENCE: 34

Trp Met Asn Thr Asn Thr Gly Glu Pro Thr Ser Leu Glu Asp Phe Lys
1               5                   10                  15

Gly

<210> SEQ ID NO 35
<211> LENGTH: 9
<212> TYPE: PRT
<213> ORGANISM: Artificial sequence
<220> FEATURE:
<223> OTHER INFORMATION: Synthetic amino acid

<400> SEQUENCE: 35

Ser Gly Gly Tyr Asp Pro Met Asp Tyr
1               5

<210> SEQ ID NO 36
<211> LENGTH: 15
<212> TYPE: PRT
<213> ORGANISM: Artificial sequence
<220> FEATURE:
<223> OTHER INFORMATION: Synthetic amino acid

<400> SEQUENCE: 36

Arg Ala Ser Glu Ser Val Asp Asn Tyr Gly Asn Thr Phe Met His
1               5                   10                  15

<210> SEQ ID NO 37
<211> LENGTH: 7
<212> TYPE: PRT
<213> ORGANISM: Artificial sequence
<220> FEATURE:
<223> OTHER INFORMATION: Synthetic amino acid

<400> SEQUENCE: 37

Arg Ala Ser Asn Leu Glu Ser
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic amino acid

<400> SEQUENCE: 38

Gln Gln Ser Lys Glu Asp Pro Pro Thr
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic amino acid

<400> SEQUENCE: 39

Asn Tyr Gly Met Asn
1               5

<210> SEQ ID NO 40
<211> LENGTH: 17
<212> TYPE: PRT
<213> ORGANISM: Artificial sequence
<220> FEATURE:
<223> OTHER INFORMATION: Synthetic amino acid

<400> SEQUENCE: 40

Trp Ile Asn Thr Tyr Thr Gly Glu Ser Thr Tyr Ser Ala Asp Phe Lys
1 5 10 15

Gly

<210> SEQ ID NO 41
<211> LENGTH: 9
<212> TYPE: PRT
<213> ORGANISM: Artificial sequence
<220> FEATURE:
<223> OTHER INFORMATION: Synthetic amino acid

<400> SEQUENCE: 41

Ser Gly Gly Tyr Asp Pro Met Asp Tyr
1 5

<210> SEQ ID NO 42
<211> LENGTH: 15
<212> TYPE: PRT
<213> ORGANISM: Artificial sequence
<220> FEATURE:
<223> OTHER INFORMATION: Synthetic amino acid

<400> SEQUENCE: 42

Arg Ala Ser Glu Ser Val Asp Asn Tyr Gly Asn Thr Phe Met His
1 5 10 15

<210> SEQ ID NO 43
<211> LENGTH: 7
<212> TYPE: PRT
<213> ORGANISM: Artificial sequence
<220> FEATURE:
<223> OTHER INFORMATION: Synthetic amino acid

<400> SEQUENCE: 43

Arg Ala Ser Asn Leu Glu Ser
1 5

<210> SEQ ID NO 44
<211> LENGTH: 9
<212> TYPE: PRT
<213> ORGANISM: Artificial sequence
<220> FEATURE:
<223> OTHER INFORMATION: Synthetic amino acid

<400> SEQUENCE: 44

Gln Gln Ser Asn Glu Asp Pro Pro Thr
1 5

<210> SEQ ID NO 45
<211> LENGTH: 12
<212> TYPE: PRT
<213> ORGANISM: Artificial sequence
<220> FEATURE:
<223> OTHER INFORMATION: Synthetic amino acid

<400> SEQUENCE: 45

Glu Ser Lys Tyr Gly Pro Pro Cys Pro Pro Cys Pro
1 5 10

<210> SEQ ID NO 46
<211> LENGTH: 41
<212> TYPE: PRT

<213> ORGANISM: Artificial sequence
<220> FEATURE:
<223> OTHER INFORMATION: Synthetic amino acid

<400> SEQUENCE: 46

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 47
<211> LENGTH: 42
<212> TYPE: PRT
<213> ORGANISM: Artificial sequence
<220> FEATURE:
<223> OTHER INFORMATION: Synthetic amino acid

<400> SEQUENCE: 47

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 48
<211> LENGTH: 493
<212> TYPE: PRT
<213> ORGANISM: Artificial sequence
<220> FEATURE:
<223> OTHER INFORMATION: Synthetic amino acid

<400> SEQUENCE: 48

```
Met Leu Leu Leu Val Thr Ser Leu Leu Leu Cys Glu Leu Pro His Pro
1               5                   10                  15

Ala Phe Leu Leu Ile Pro Asp Val Gln Ile Thr Gln Ser Pro Ser Tyr
            20                  25                  30

Leu Ala Ala Ser Pro Gly Glu Thr Ile Thr Ile Asn Cys Arg Ala Ser
        35                  40                  45

Lys Ser Ile Ser Lys Asp Leu Ala Trp Tyr Gln Glu Lys Pro Gly Lys
    50                  55                  60

Thr Asn Lys Leu Leu Ile Tyr Ser Gly Ser Thr Leu Gln Ser Gly Ile
65                  70                  75                  80

Pro Ser Arg Phe Ser Gly Ser Gly Ser Gly Thr Asp Phe Thr Leu Thr
                85                  90                  95

Ile Ser Ser Leu Glu Pro Glu Asp Phe Ala Met Tyr Tyr Cys Gln Gln
            100                 105                 110

His Asn Lys Tyr Pro Tyr Thr Phe Gly Gly Gly Thr Lys Leu Glu Ile
        115                 120                 125

Lys Gly Ser Thr Ser Gly Ser Gly Lys Pro Gly Ser Gly Glu Gly Ser
    130                 135                 140

Thr Lys Gly Gln Ile Gln Leu Val Gln Ser Gly Pro Glu Leu Lys Lys
145                 150                 155                 160

Pro Gly Glu Thr Val Lys Ile Ser Cys Lys Thr Ser Gly Tyr Val Phe
                165                 170                 175

Thr Asn Tyr Gly Met Asn Trp Val Lys Gln Ala Pro Gly Lys Gly Phe
            180                 185                 190
```

```
Lys Trp Met Gly Trp Met Asn Thr Asn Thr Gly Glu Pro Thr Ser Leu
        195                 200                 205

Glu Asp Phe Lys Gly Arg Phe Ala Phe Ser Leu Glu Thr Ser Ala Ser
    210                 215                 220

Thr Ala Tyr Leu Gln Ile Asn Asn Leu Lys Asn Asp Asp Thr Ala Thr
225                 230                 235                 240

Tyr Phe Cys Ala Arg Ser Gly Gly Tyr Asp Pro Met Asp Tyr Trp Gly
                245                 250                 255

Gln Gly Thr Ser Val Thr Val Ser Ser Lys Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Asn His Arg Asn Arg Ser Lys Arg Ser Arg Gly Gly His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 49
<211> LENGTH: 493
<212> TYPE: PRT
<213> ORGANISM: Artificial sequence
<220> FEATURE:
<223> OTHER INFORMATION: Synthetic amino acid

<400> SEQUENCE: 49

Met Leu Leu Leu Val Thr Ser Leu Leu Leu Cys Glu Leu Pro His Pro
1               5                   10                  15

Ala Phe Leu Leu Ile Pro Asp Val Gln Ile Thr Gln Ser Pro Ser Tyr
            20                  25                  30

Leu Ala Ala Ser Pro Gly Glu Thr Ile Thr Ile Asn Cys Arg Ala Ser
        35                  40                  45

Lys Ser Ile Ser Lys Asp Leu Ala Trp Tyr Gln Glu Lys Pro Gly Lys
    50                  55                  60
```

```
Thr Asn Lys Leu Leu Ile Tyr Ser Gly Ser Thr Leu Gln Ser Gly Ile
65                  70                  75                  80

Pro Ser Arg Phe Ser Gly Ser Gly Ser Gly Thr Asp Phe Thr Leu Thr
                85                  90                  95

Ile Ser Ser Leu Glu Pro Glu Asp Phe Ala Met Tyr Tyr Cys Gln Gln
            100                 105                 110

His Asn Lys Tyr Pro Tyr Thr Phe Gly Gly Gly Thr Lys Leu Glu Ile
        115                 120                 125

Lys Gly Ser Thr Ser Gly Ser Gly Lys Pro Gly Ser Gly Glu Gly Ser
    130                 135                 140

Thr Lys Gly Gln Val Gln Leu Gln Gln Pro Gly Ala Glu Leu Val Lys
145                 150                 155                 160

Pro Gly Ala Pro Val Lys Leu Ser Cys Lys Ala Ser Gly Tyr Thr Phe
                165                 170                 175

Thr Asn Tyr Trp Met Asn Trp Ile Lys Gln Arg Pro Gly Arg Gly Leu
            180                 185                 190

Glu Trp Ile Gly Arg Ile Asp Pro Ser Asp Ser Glu Ser His Tyr Asn
        195                 200                 205

Gln Lys Phe Lys Asp Lys Ala Thr Leu Thr Val Asp Lys Ser Ser Asn
    210                 215                 220

Thr Ala Tyr Ile Gln Leu Ser Ser Leu Thr Ser Glu Asp Ser Ala Val
225                 230                 235                 240

Tyr Tyr Cys Ala Arg Tyr Asp Tyr Asp Asp Thr Met Asp Tyr Trp Gly
                245                 250                 255

Gln Gly Thr Ser Val Thr Val Ser Ser Lys Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Asn His Arg Asn Arg Ser Lys Arg Ser Arg Gly Gly His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480
```

```
Thr Tyr Asp Ala Leu His Met Gln Ala Leu Pro Pro Arg
                485                 490


<210> SEQ ID NO 50
<211> LENGTH: 493
<212> TYPE: PRT
<213> ORGANISM: Artificial sequence
<220> FEATURE:
<223> OTHER INFORMATION: Synthetic amino acid

<400> SEQUENCE: 50

Met Leu Leu Leu Val Thr Ser Leu Leu Leu Cys Glu Leu Pro His Pro
1               5                   10                  15

Ala Phe Leu Leu Ile Pro Asp Val Gln Ile Thr Gln Ser Pro Ser Tyr
            20                  25                  30

Leu Ala Ala Ser Pro Gly Glu Thr Ile Thr Ile Asn Cys Arg Ala Ser
        35                  40                  45

Lys Ser Ile Ser Lys Asp Leu Ala Trp Tyr Gln Glu Lys Pro Gly Lys
    50                  55                  60

Thr Asn Lys Leu Leu Ile Tyr Ser Gly Ser Thr Leu Gln Ser Gly Ile
65                  70                  75                  80

Pro Ser Arg Phe Ser Gly Ser Gly Ser Gly Thr Asp Phe Thr Leu Thr
                85                  90                  95

Ile Ser Ser Leu Glu Pro Glu Asp Phe Ala Met Tyr Tyr Cys Gln Gln
            100                 105                 110

His Asn Lys Tyr Pro Tyr Thr Phe Gly Gly Gly Thr Lys Leu Glu Ile
        115                 120                 125

Lys Gly Ser Thr Ser Gly Ser Gly Lys Pro Gly Ser Gly Glu Gly Ser
    130                 135                 140

Thr Lys Gly Gln Ile Gln Leu Val Gln Ser Gly Pro Glu Leu Lys Lys
145                 150                 155                 160

Pro Gly Glu Thr Val Lys Ile Ser Cys Lys Ala Ser Gly Tyr Ile Phe
                165                 170                 175

Thr Asn Tyr Gly Met Asn Trp Val Lys Gln Ala Pro Gly Lys Ser Phe
            180                 185                 190

Lys Trp Met Gly Trp Ile Asn Thr Tyr Thr Gly Glu Ser Thr Tyr Ser
        195                 200                 205

Ala Asp Phe Lys Gly Arg Phe Ala Phe Ser Leu Glu Thr Ser Ala Ser
    210                 215                 220

Thr Ala Tyr Leu His Ile Asn Asp Leu Lys Asn Glu Asp Thr Ala Thr
225                 230                 235                 240

Tyr Phe Cys Ala Arg Ser Gly Gly Tyr Asp Pro Met Asp Tyr Trp Gly
                245                 250                 255

Gln Gly Thr Ser Val Thr Val Ser Ser Lys Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Asn His Arg Asn Arg Ser Lys Arg Ser Arg Gly Gly His Ser Asp Tyr
            340                 345                 350
```

```
Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 51
<211> LENGTH: 497
<212> TYPE: PRT
<213> ORGANISM: Artificial sequence
<220> FEATURE:
<223> OTHER INFORMATION: Synthetic amino acid

<400> SEQUENCE: 51

Met Leu Leu Leu Val Thr Ser Leu Leu Leu Cys Glu Leu Pro His Pro
1               5                   10                  15

Ala Phe Leu Leu Ile Pro Asp Ile Val Leu Thr Gln Ser Pro Ala Ser
            20                  25                  30

Leu Ala Val Ser Pro Gly Gln Arg Ala Thr Ile Ser Cys Arg Ala Ser
        35                  40                  45

Glu Ser Val Asp Asn Tyr Gly Asn Thr Phe Met His Trp Tyr Gln Gln
    50                  55                  60

Lys Pro Gly Gln Pro Pro Lys Leu Leu Ile Tyr Arg Ala Ser Asn Leu
65                  70                  75                  80

Glu Ser Gly Ile Pro Ala Arg Phe Ser Gly Ser Asp Ser Arg Thr Asp
                85                  90                  95

Phe Thr Leu Thr Ile Asn Pro Val Glu Ala Asp Asp Val Ala Thr Tyr
            100                 105                 110

Tyr Cys Gln Gln Ser Lys Glu Asp Pro Pro Thr Phe Gly Ala Gly Thr
        115                 120                 125

Lys Leu Glu Leu Lys Gly Ser Thr Ser Gly Ser Gly Lys Pro Gly Ser
    130                 135                 140

Gly Glu Gly Ser Thr Lys Gly Gln Ile Gln Leu Val Gln Ser Gly Pro
145                 150                 155                 160

Glu Leu Lys Lys Pro Gly Glu Thr Val Lys Ile Ser Cys Lys Ala Ser
                165                 170                 175

Gly Tyr Ile Phe Thr Asn Tyr Gly Met Asn Trp Val Lys Gln Ala Pro
            180                 185                 190

Gly Lys Ser Phe Lys Trp Met Gly Trp Ile Asn Thr Tyr Thr Gly Glu
        195                 200                 205

Ser Thr Tyr Ser Ala Asp Phe Lys Gly Arg Phe Ala Phe Ser Leu Glu
    210                 215                 220
```

```
Thr Ser Ala Ser Thr Ala Tyr Leu His Ile Asn Asp Leu Lys Asn Glu
225                 230                 235                 240

Asp Thr Ala Thr Tyr Phe Cys Ala Arg Ser Gly Gly Tyr Asp Pro Met
                245                 250                 255

Asp Tyr Trp Gly Gln Gly Thr Ser Val Thr Val Ser Ser Lys Pro Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Asn His Arg Asn Arg Ser Lys Arg Ser Arg Gly Gly
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 52
<211> LENGTH: 498
<212> TYPE: PRT
<213> ORGANISM: Artificial sequence
<220> FEATURE:
<223> OTHER INFORMATION: Synthetic amino acid

<400> SEQUENCE: 52

```
Met Leu Leu Leu Val Thr Ser Leu Leu Leu Cys Glu Leu Pro His Pro
1               5                   10                  15

Ala Phe Leu Leu Ile Pro Asp Ile Val Met Thr Gln Ala Ala Pro Ser
            20                  25                  30

Val Pro Val Thr Pro Gly Glu Ser Val Ser Ile Ser Cys Arg Ser Asn
        35                  40                  45

Lys Ser Leu Leu His Ser Asn Gly Asn Thr Tyr Leu Tyr Trp Phe Leu
    50                  55                  60

Gln Arg Pro Gly Gln Ser Pro Gln Leu Leu Ile Tyr Arg Met Ser Asn
65                  70                  75                  80

Leu Ala Ser Gly Val Pro Asp Arg Phe Ser Gly Ser Gly Ser Gly Thr
```

```
                85                  90                  95

Ala Phe Thr Leu Arg Ile Ser Arg Val Glu Ala Glu Asp Val Gly Val
            100                 105                 110

Tyr Tyr Cys Met Gln His Leu Glu Tyr Pro Tyr Thr Phe Gly Gly Gly
        115                 120                 125

Thr Lys Leu Glu Ile Lys Gly Ser Thr Ser Gly Ser Gly Lys Pro Gly
    130                 135                 140

Ser Gly Glu Gly Ser Thr Lys Gly Gln Ile Gln Leu Val Gln Ser Gly
145                 150                 155                 160

Pro Glu Leu Lys Lys Pro Gly Glu Thr Val Lys Ile Ser Cys Lys Thr
                165                 170                 175

Ser Gly Tyr Val Phe Thr Asn Tyr Gly Met Asn Trp Val Lys Gln Ala
            180                 185                 190

Pro Gly Lys Gly Phe Lys Trp Met Gly Trp Met Asn Thr Asn Thr Gly
        195                 200                 205

Glu Pro Thr Ser Leu Glu Asp Phe Lys Gly Arg Phe Ala Phe Ser Leu
    210                 215                 220

Glu Thr Ser Ala Ser Thr Ala Tyr Leu Gln Ile Asn Asn Leu Lys Asn
225                 230                 235                 240

Asp Asp Thr Ala Thr Tyr Phe Cys Ala Arg Ser Gly Gly Tyr Asp Pro
                245                 250                 255

Met Asp Tyr Trp Gly Gln Gly Thr Ser Val Thr Val Ser Ser Lys Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Asn His Arg Asn Arg Ser Lys Arg Ser Arg Gly
            340                 345                 350

Gly His Ser Asp Tyr Met Asn Met Thr Pro Arg Arg Pro Gly Pro Thr
        355                 360                 365

Arg Lys His Tyr Gln Pro Tyr Ala Pro Pro Arg Asp Phe Ala Ala Tyr
    370                 375                 380

Arg Ser Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg
```

<210> SEQ ID NO 53
<211> LENGTH: 675
<212> TYPE: PRT
<213> ORGANISM: Artificial sequence
<220> FEATURE:
<223> OTHER INFORMATION: Synthetic amino acid

<400> SEQUENCE: 53

```
Met Leu Leu Leu Val Thr Ser Leu Leu Leu Cys Glu Leu Pro His Pro
1               5                   10                  15

Ala Phe Leu Leu Ile Pro Asp Val Gln Ile Thr Gln Ser Pro Ser Tyr
            20                  25                  30

Leu Ala Ala Ser Pro Gly Glu Thr Ile Thr Ile Asn Cys Arg Ala Ser
        35                  40                  45

Lys Ser Ile Ser Lys Asp Leu Ala Trp Tyr Gln Glu Lys Pro Gly Lys
    50                  55                  60

Thr Asn Lys Leu Leu Ile Tyr Ser Gly Ser Thr Leu Gln Ser Gly Ile
65                  70                  75                  80

Pro Ser Arg Phe Ser Gly Ser Gly Ser Gly Thr Asp Phe Thr Leu Thr
                85                  90                  95

Ile Ser Ser Leu Glu Pro Glu Asp Phe Ala Met Tyr Tyr Cys Gln Gln
            100                 105                 110

His Asn Lys Tyr Pro Tyr Thr Phe Gly Gly Gly Thr Lys Leu Glu Ile
        115                 120                 125

Lys Gly Ser Thr Ser Gly Ser Gly Lys Pro Gly Ser Gly Glu Gly Ser
    130                 135                 140

Thr Lys Gly Gln Val Gln Leu Gln Gln Pro Gly Ala Glu Leu Val Lys
145                 150                 155                 160

Pro Gly Ala Pro Val Lys Leu Ser Cys Lys Ala Ser Gly Tyr Thr Phe
                165                 170                 175

Thr Asn Tyr Trp Met Asn Trp Ile Lys Gln Arg Pro Gly Arg Gly Leu
            180                 185                 190

Glu Trp Ile Gly Arg Ile Asp Pro Ser Asp Ser Glu Ser His Tyr Asn
        195                 200                 205

Gln Lys Phe Lys Asp Lys Ala Thr Leu Thr Val Asp Lys Ser Ser Asn
    210                 215                 220

Thr Ala Tyr Ile Gln Leu Ser Ser Leu Thr Ser Glu Asp Ser Ala Val
225                 230                 235                 240

Tyr Tyr Cys Ala Arg Tyr Asp Tyr Asp Asp Thr Met Asp Tyr Trp Gly
                245                 250                 255

Gln Gly Thr Ser Val Thr Val Ser Ser Glu Ser Lys Tyr Gly Pro Pro
            260                 265                 270

Cys Pro Pro Cys Pro Ala Pro Glu Phe Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser Gln Glu Asp Pro Glu Val
305                 310                 315                 320

Gln Phe Asn Trp Tyr Val Asp Gly Val Glu Val His Asn Ala Lys Thr
                325                 330                 335

Lys Pro Arg Glu Glu Gln Phe Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365
```

-continued

```
Lys Val Ser Asn Lys Gly Leu Pro Ser Ser Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Arg Leu Thr Val Asp Lys Ser Arg Trp
    450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Met Phe
                485                 490                 495

Trp Val Leu Val Val Val Gly Gly Val Leu Ala Cys Tyr Ser Leu Leu
            500                 505                 510

Val Thr Val Ala Phe Ile Ile Phe Trp Val Arg Ser Lys Arg Ser Arg
        515                 520                 525

Gly Gly His Ser Asp Tyr Met Asn Met Thr Pro Arg Arg Pro Gly Pro
    530                 535                 540

Thr Arg Lys His Tyr Gln Pro Tyr Ala Pro Pro Arg Asp Phe Ala Ala
545                 550                 555                 560

Tyr Arg Ser Arg Val Lys Phe Ser Arg Ser Ala Asp Ala Pro Ala Tyr
                565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
        595                 600                 605

Gly Gly Lys Pro Arg Arg Lys Asn Pro Gln Glu Gly Leu Tyr Asn Glu
    610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
                645                 650                 655

Ser Thr Ala Thr Lys Asp Thr Tyr Asp Ala Leu His Met Gln Ala Leu
            660                 665                 670

Pro Pro Arg
        675
```

UNITED STATES PATENT AND TRADEMARK OFFICE
CERTIFICATE OF CORRECTION

PATENT NO. : 11,059,879 B2
APPLICATION NO. : 15/771128
DATED : July 13, 2021
INVENTOR(S) : Thokala et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 284 days.

Signed and Sealed this
Thirty-first Day of January, 2023

Katherine Kelly Vidal
*Director of the United States Patent and Trademark Office*